US011267853B2

(12) United States Patent
Reshetnyak et al.

(10) Patent No.: US 11,267,853 B2
(45) Date of Patent: Mar. 8, 2022

(54) CARBOHYDRATE TETHERING AT CELL SURFACES TO INDUCE IMMUNE RESPONSE

(71) Applicants: University of Rhode Island Board of Trustees, Kingston, RI (US); Yale University, New Haven, CT (US)

(72) Inventors: Yana K. Reshetnyak, Saunderstown, RI (US); Oleg A. Andreev, Saunderstown, RI (US); Anna Moshnikova, Warwick, RI (US); Donald M. Engelman, New Haven, CT (US)

(73) Assignees: University of Rhode Island Board of Trustees, Kingston, RI (US); Yale University, New Haven, CT (US)

( * ) Notice: Subject to any disclaimer, the term of this patent is extended or adjusted under 35 U.S.C. 154(b) by 0 days.

(21) Appl. No.: 16/775,046

(22) Filed: Jan. 28, 2020

(65) Prior Publication Data

US 2020/0262881 A1    Aug. 20, 2020

Related U.S. Application Data

(60) Provisional application No. 62/797,919, filed on Jan. 28, 2019.

(51) Int. Cl.
| | |
|---|---|
| *A61K 38/00* | (2006.01) |
| *C07K 14/47* | (2006.01) |
| *A61K 47/65* | (2017.01) |
| *A61K 9/00* | (2006.01) |
| *A61P 35/00* | (2006.01) |
| *A61K 47/64* | (2017.01) |

(52) U.S. Cl.
CPC ........ *C07K 14/4725* (2013.01); *A61K 9/0019* (2013.01); *A61K 47/646* (2017.08); *A61K 47/65* (2017.08); *A61P 35/00* (2018.01)

(58) Field of Classification Search
CPC ...... A61K 47/65; A61K 9/0019; A61K 47/64; A61K 47/646; A61P 35/00; C07K 14/4725; C07K 14/705; C07K 2319/03
See application file for complete search history.

(56) References Cited

U.S. PATENT DOCUMENTS

| | | | |
|---|---|---|---|
| 9,289,508 B2 | 3/2016 | Reshetnyak et al. | |
| 9,814,781 B2 | 11/2017 | Reshetnyak et al. | |
| 2008/0233107 A1 | 9/2008 | Reshetnyak et al. | |
| 2012/0039990 A1 | 2/2012 | Reshetnyak et al. | |
| 2012/0064108 A1* | 3/2012 | Avci ................. | A61K 47/61 424/193.1 |
| 2012/0142042 A1 | 6/2012 | Reshetnyak et al. | |
| 2015/0051153 A1 | 2/2015 | Reshetnyak et al. | |
| 2015/0191508 A1 | 7/2015 | Reshetnyak et al. | |
| 2016/0053292 A1* | 2/2016 | Bosques .............. | C12P 21/005 435/68.1 |
| 2016/0256560 A1 | 9/2016 | Reshetnyak et al. | |
| 2018/0064648 A1 | 3/2018 | Reshetnyak et al. | |
| 2018/0117183 A1 | 5/2018 | Reshetnyak et al. | |
| 2018/0221500 A1 | 8/2018 | Reshetnyak et al. | |
| 2018/0369425 A1 | 12/2018 | Reshetnyak et al. | |

FOREIGN PATENT DOCUMENTS

| | | | | |
|---|---|---|---|---|
| WO | WO-2012047354 A2 * | 4/2012 | ............. | A61K 38/04 |
| WO | 2017/165452 A1 | 9/2017 | | |
| WO | 2018/057912 A1 | 3/2018 | | |

OTHER PUBLICATIONS

Altschul et al. (1990) "Basic Local Alignment Search Tool", Journal of Molecular Biology, 215:403-410.
Altschul et al. (1997) "Gapped BLAST and PSI-BLAST: A New Generation of Protein Database Search Programs", Nucleic Acids Research, 25(17):3389-3402.
Dean (2005) "Blood Groups and Red Cell Antigens", National Center for Biotechnology Information, 98 pages.
Godzisz (Sep. 1979) "Synthesis of Natural Allohemagglutinins of the ABO System in Healthy Children Aged 3 Months to 3 Years", Rev. Fr. Tranfus. Immunohematol, 22(4): 399-412 (English abstract).
Henikoff et al. (Nov. 15, 1992) "Amino Acid Substitution Matrices from Protein Blocks", Proceedings of the National Academy of Sciences of the United States of America, 89(22):10915-10919.
Liu et al. (Jul./Aug. 1996) "The Development of ABO Isohemagglutinins in Taiwanese", Hum Hered, 46(4):181-184.
Needleman et al. (Mar. 28, 1970) "A General Method Applicable to the Search for Similarities in the Amino Acid Sequence of Two Proteins", Journal of Molecular Biology, 48(3):443-453.
Pearson et al. (Apr. 1988) "Improved Tools for Biological Sequence Comparison", Proceedings of the National Academy of Sciences, 85:2444-2448.
Porubsky et al. (Apr. 3, 2007) "Normal Development and Function of Invariant Natural Killer T Cells in Mice with Ioglobotrihexosylceramide (iGb3) Deficiency", PNAS, 104(14):5977-5982.
Smith et al. (Dec. 1981) "Comparison of Biosequences", Advances in Applied Mathematics, 2(4):482-489.
Wang et al. (Aug. 19, 2008) "Glycan Microarray of Globo H and Related Structures for Quantitative Analysis of Breast Cancer", PNAS, 105(33):11661-11666.

* cited by examiner

*Primary Examiner* — Aradhana Sasan
*Assistant Examiner* — Mercy H Sabila
(74) *Attorney, Agent, or Firm* — Mintz Levin Cohn Ferris Glovsky and Popeo, P.C.; Ingrid A. Beattie

(57) ABSTRACT

The invention features a compositions and methods for inducing an immune response to targeted cells. The compositions induce targeting of a cell by positioning carbohydrate epitopes on the surface of the cell by conjugation of the epitope to a pH-triggered membrane peptide (pHLIP®).

24 Claims, 15 Drawing Sheets

Specification includes a Sequence Listing.

N-linked Glycoproteins – High Man

N-linked Glycoproteins – Complex

N-linked Glycoproteins – Mixed (Hybrid)

CARBOHYDRATE TETHERING AT CELL SURFACES TO INDUCE IMMUNE RESPONSE

RELATED APPLICATIONS

This application claims the benefit of priority under 35 U.S.C. § 119(e) to U.S. Provisional Application No. 62/797,919, filed Jan. 28, 2019, the entire contents of which is incorporated herein by reference in its entirety.

STATEMENT AS TO FEDERALLY SPONSORED RESEARCH

This invention was made with government support under R01 GM073857 awarded by the National Institute of General Medical Sciences of the National Institutes of Health. The government has certain rights in the invention.

INCORPORATION BY REFERENCE OF SEQUENCE LISTING

The contents of the sequence listing text file named "040984-513001US_SL.txt", which was created on Nov. 18, 2020 and is 159,999 bytes in size, is hereby incorporated by reference in its entirety.

FIELD OF THE INVENTION

The present invention relates to immunotherapy.

BACKGROUND

Conventional methods of cancer treatment are toxic and do not distinguish between normal and tumor tissues very well. As a result, such treatments often come with harmful side effects for patients. Recent studies in cancer immunotherapy have shown that boosting the immune system of patients with cancer can have a beneficial effect on the outcomes of cancer treatments, alone or in combination with conventional treatments.

Thus, a current challenge in the field of immunotherapy is to search for compositions and methods to activate the immune response in diseased tissues while avoiding deleterious side effects.

SUMMARY OF THE INVENTION

The invention provides a solution to the problem of activating the immune response toward cells in diseased tissues, e.g., tumors, and guiding the immune reaction away from normal tissues and thus providing therapy while avoiding side effects.

Provided herein are compositions and methods for the decoration of target cells with carbohydrate epitopes (on the cell surface) that can recruit endogenous antibodies, e.g., antibodies present in the body of the subject prior to the treatment, or developed in the course of immunization or immune boost, leading to initiation of antibody-dependent cell-mediated cytotoxicity (ADCC) and/or activation of the classical complement cascade to assemble a membrane attack complex that results in cell death. The decorated cell-surface target cells are the more effectively killed compared to such cells without modification using pHLIP® mediated carbohydrate tethering. The activation of the complement cascade can further amplify immune responses through the release of cytokines and inflammatory mediators. These signaling molecules attract immune cells such as neutrophils, macrophages, cytotoxic T and natural killer (NK) cells. Immune effector cells, recognizing surface-bound antibodies, initiate antibody-dependent cell-mediated cytotoxicity (ADCC) through activating Fc receptors.

Tumors are characterized by a tumor micro environment (TME) of a lower pH than the surrounding tissues, and because of the metabolism accompanying their rapid and uncontrolled cell proliferation, a flux of acidity emerging from the cancer cells results. Moreover, due to the flux and the membrane potential, the extracellular pH is lowest at the surfaces of cancer cells and is significantly lower than the bulk extracellular pH in tumors. The low pH region persists at the cancer cell surfaces even in well-perfused tumor areas.

A pH Low Insertion Peptide (pHLIP®) is a water-soluble membrane peptide that interacts weakly with a cell membrane at neutral pH, without insertion into the lipid bilayer; however, at slightly acidic pH (<7.0), a pHLIP® inserts into the cell membrane and, if it is long enough and non-cyclic, can form a stable transmembrane alpha-helix. In addition to tumor cells characterized by low pH (<7.0), immune cells within a tumor mass are also characterized by low pH (<7.0). For example, the cells within the environment of a tumor mass, e.g., macrophages, are also characterized by a low surface pH. By binding a pHLIP®, or pHLIP® equivalent, to a carbohydrate epitope, it is possible to specifically target the cell to recognize or recruit endogenous (natural) antibodies circulating in the blood and thereby initiate an immune response. A significant advantage of this approach is that the augmented immune response stimulated by the pHLIP® constructs described herein are associated with few to no side effects for the patient.

Accordingly, the invention features a composition comprising a carbohydrate epitope conjugated to a pH-triggered membrane peptide (pHLIP®) comprising at least 4 amino acids. For example, the pHLIP® peptide may be a linear peptide or a cyclic peptide, e.g., as described in PCT Application No. PCT/US2017/023458. The carbohydrate epitope is selectively positioned on the surface of the cell in targeted diseased tissue by pHLIP® to induce an immune reaction predominantly in diseased tissue (tumor) or, e.g., induce "tumor rejection". The composition is a carbohydrate epitope conjugated to pHLIP®, and pHLIP® targets epitope to the cell surface.

In examples, the carbohydrate epitope can include an N-linked glycan, an O-linked glycan, or any combination thereof. An epitope is a molecular region of an antigen capable of eliciting an immune response and of combining with a specific antibody or immune cell produced by such a response. An epitope is also known as an antigenic determinant. For example, an epitope is a part of an antigen molecule to which an antibody attaches or to which an immune cell attaches.

As described herein, the compositions can include at least two carbohydrate epitopes which are conjugated to the pHLIP®. Alternatively, the carbohydrate epitope may be conjugated to at least two pHLIP® peptides. In other examples, at least two carbohydrate epitopes may be conjugated to at least two pHLIP® peptides.

In some examples, the composition comprises 2 or more pHLIP® peptides, or alternatively, two or more carbohydrate epitopes. An epitope is a molecular region of an antigen capable of eliciting an immune response and of combining with a specific antibody or immune cell produced by such a response. An epitope is also known as an antigenic determinant. For example, an epitope is a part of an antigen molecule to which an antibody attaches or to which an immune cell attaches. Exemplary constructs comprise the following structure: Carb-Linker, Peptide, in which:

Carb includes a carbohydrate epitope to induce an immune response by attracting of endogenous, natural, antibodies.

Peptide is a pHLIP® peptide (e.g., a first pHLIP peptide®) comprising the sequence: xXDDQNPWRAYLDLL-FPTDTLLLDLLWA (SEQ ID NO: 1) or xXDQDNPWRAY-LDLLFPTDTLLLDLLWA (SEQ ID NO: 2), wherein an upper case "X" indicates any amino acid residue, including, for example a lysine (Lys), a cysteine (Cys), a serine (Ser), a theranine (Thr), or an Azido-containing amino acid, e.g., for conjugation to another moiety. A lower case "x" indicates any amino acid residue, e.g., including but not limited to alanine, serine, asparagine, or threonine. In some examples, an Ala is used as first residue to reduce degradation of peptide. These considerations relate to peptide stability rather than functionality. The linker is attached to upper case X.

Linker is a linker, wherein the linker is a polyethylene glycol or an extension of the membrane non-inserting flanking region of pHLIP® peptide. Non-limiting examples of linker is a polyethylene glycol (PEG) polymer in size from 200 Da to 20 kDa. Non-limiting example of an extension is a poly-Glycine polypeptide. Carbohydrates are also linked to pHLIP® peptide(s) via non-cleavable link(s).

Each "-" may be a covalent bond.

Exemplary constructs comprise the following structure: Carb$_2$-Linker$_2$-Peptide, to position 2 epitopes for binding of both heads of the same antibody molecule, in which:

Carb includes a carbohydrate epitope to induce an immune response by attracting of endogenous, natural, antibodies.

Peptide is a pHLIP® peptide comprising the sequence: AX(Z)$_n$XPWRAYLDLLFPTDTLLLDLLWA (SEQ ID NO: 473), wherein an upper case "X" indicates any amino acid residue, e.g., including a lysine (Lys), a cysteine (Cys), or an Azido-containing amino acid, e.g., for conjugation to another moiety, "Z" indicates any amino acid residue, and n represents any integer between, and including 1-10 (e.g., 1≤n≤10). For example, (Z)$_n$ may be QDNDQN (SEQ ID NO: 6) or any combination of polar residues, e.g., D, E, N or Q.

A compound is characterized as polar if it has a log P of less than −0.4. The carbohydrate may be moderately hydrophobic. Polar: Log P<−0.4; Moderately hydrophobic: 2.5<Log P<−0.4; and Hydrophobic: Log P>2.5. The polarity and/or hydrophobicity of a carbohydrate is measured using methods known in the art, e.g., by determining Log P, in which P is the octanol-water partition coefficient. A substance is dissolved into an octanol-water mixture, mixed, and allowed to come to equilibration. The amount of substance in each (or one) phases is then measured. The measurements itself could be in a number of ways known in the art, e.g., by measuring absorbance, or determining the amount using NMR, HPLC, or other known methods. As described herein, moderately hydrophobic, for example, is defined as molecule with Log P value in the range of 2.5 to −0.4, there are a lot of examples.

Linker is a linker, wherein the linker is a polyethylene glycol. For example, the linker may include PEG$_m$, wherein m is an integer between and including 12-24 (e.g., 12≤m≤24), and each "-" may be a covalent bond.

Furthermore, the carbohydrate epitope may be conjugated to the pHLIP® peptide via a linker. In examples, the linker may be a covalent bond or a chemical linker. The chemical linker may include a poly(ethylene glycol) (PEG) polymer of a range of sizes, or an extension of the N-terminal membrane non-inserting flanking region of pHLIP® peptide. In some examples, the linker may be from about 200 Da to about 20 kDa in size. In some examples, the extension of the pHLIP® peptide may be poly Glycine (poly-Gly).

When the epitope is conjugated to a pHLIP® peptide via a PEG12-24 linker and peptide an additional 6-8 residues are positioned between epitope-PEG attachment to the pHLIP® peptide, the distance between epitopes can be in the range of 5-25 nm. Alternatively, the distance may be about 10 nm, or 10-15 nm, which corresponds to a typical distance between the two antigen binding sites binding sites of an antibody (FIG. 5B).

In examples, and as described herein, the pHLIP® comprises the sequence AXDDQNPWRAYLDLL-FPTDTLLLDLLWA (SEQ ID NO: 3) or AXDQDNP-WRAYLDLLFPTDTLLLDLLWA (SEQ ID NO: 4) or AX(Z)$_n$XPWRAYLDLLFPTDTLLLDLLWA (SEQ ID NO: 5), wherein X is selected from the group consisting of lysine (Lys), cysteine (Cys), or an Azido-containing amino acid, and, Z is any residue, and n is any integer between 1-10, and including 1 and 10 (e.g., 1≤n≤10).

Carbohydrates may be linked (e.g., directly and covalently) to a pHLIP® at, e.g., a serine or threonine residue. The carbohydrate epitope, as described herein can include an N-linked glycan, an O-linked glycan, or any combination thereof. In examples, the N-linked glycan and the O-linked glycan include Mannose-N-acetylgalactosamine [(Man)$_3$(GlcNAc)$_2$] (shown below):

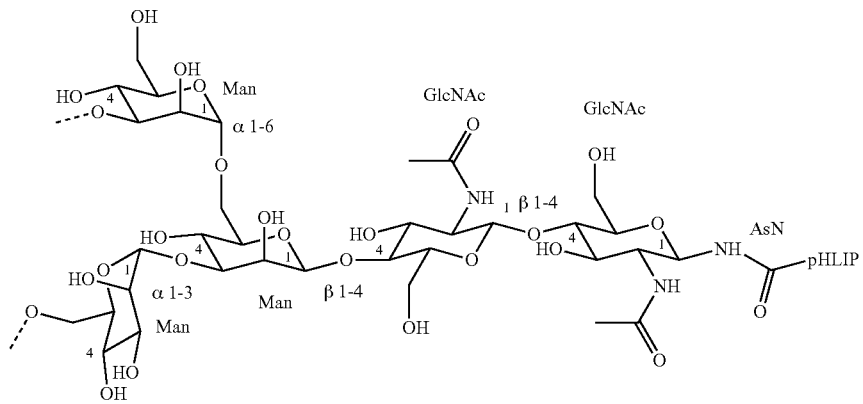

Additional specific examples may include high mannose, complex and hybrid glycans as depicted in FIG. 7A-7C.

Additionally, the glycan may include Galactose-α-1,3-Galactose or Gal-α-1,3-Gal (αGal) (shown below; also Galactose-α-1,3-Galactose or Gal-α-1,3-Gal (αGal) are used interchangeably). Gal-α-1,4-Gal; Gal-α-1,6-Gal; Gal-α-1,3-Glc; Fuc-α-1,2-Gal; Gal-β-1,2-Gal and their derivatives:

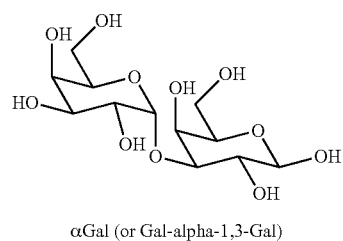 [SMILES: OCC1OC(OC2C(O)C(O)OC(CO)C2O)C(O)C(O)C1O]

αGal (or Gal-alpha-1,3-Gal)

In humans, a Gal-α-1,3-Gal link is recognized as foreign and a significant immune response against it is developed. Thus, αGal (di-Gal or tri-Gal) and its derivatives are linked to the membrane non-inserting part of pHLIP® (e.g., as shown in FIG. 5A as "carbohydrate") to position αGal at surface of targeted cell and induce immune response predominantly within diseased tissues.

The glycan (carbohydrate epitope) may also include sulfur (SH) derivatives of di-Gal and tri-Gal. An example of SH derivatives of di- and tri-Gal are depicted below:

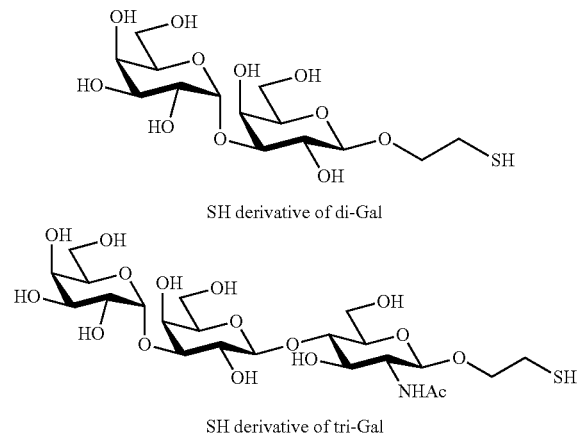

SH derivative of di-Gal

SH derivative of tri-Gal

Also, the glycan may include α-rhamnose, an unusual bacterial sugar occurring the L-form, (depicted below), for which natural antibodies are produced in human body.

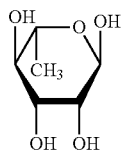

A non-limiting example of rhmanose a derivative is rhamnose-PEG12-malemide (shown below) ready for conjugation with pHLIP peptide:

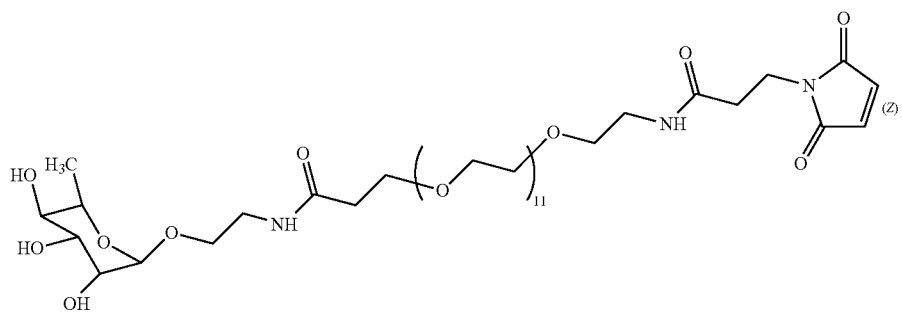

Furthermore, the glycan may include sialic acid (shown below) and its derivatives, e.g., for binding hemagglutinin (an antigenic glycoprotein on the surface of influenza viruses).

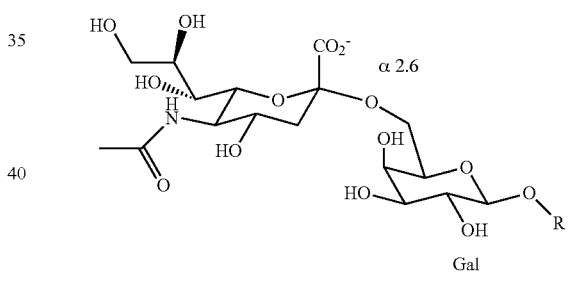

Sia a(2,6) Gal

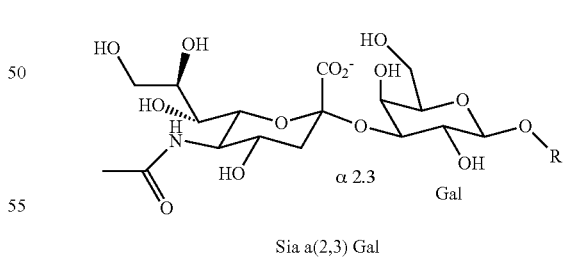

Sia a(2,3) Gal

Furthermore, the carbohydrate epitope, as described herein may include a hexasaccharide, e.g., the Globo H epitope or its derivatives. Globo H epitopes are antigenic carbohydrates that are highly expressed in various cancers, including breast, prostate and lung (see, e.g., Wang et al. PNAS Aug. 19, 2008 vol. 105(33) pages 11661-11666, incorporated herein by reference in its entirety).

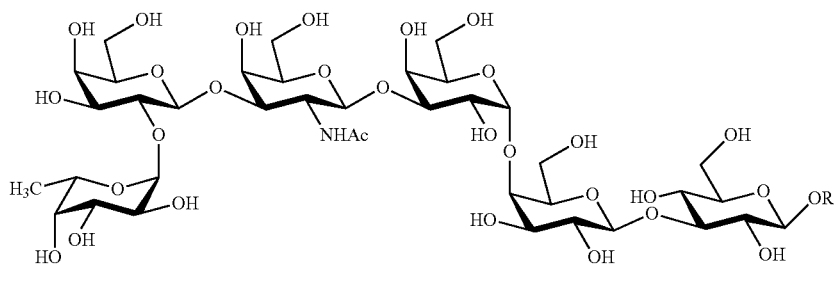

Globo H

Furthermore, the carbohydrate epitope, as described herein may include a blood group antigen or its derivatives. For example, the blood antigen may include an O antigen or its derivatives, an A antigen or its derivatives, or a B antigen or its derivatives. Patients with blood group A have B antibodies in their blood, whereas patients with blood group B have A antibodies in their blood, patients with blood group AB have no antibodies against A or B antigens in their blood, and patients with blood group O have both A and B antibodies in their blood. The core saccharide of O (or H), A and B antigens are depicted:

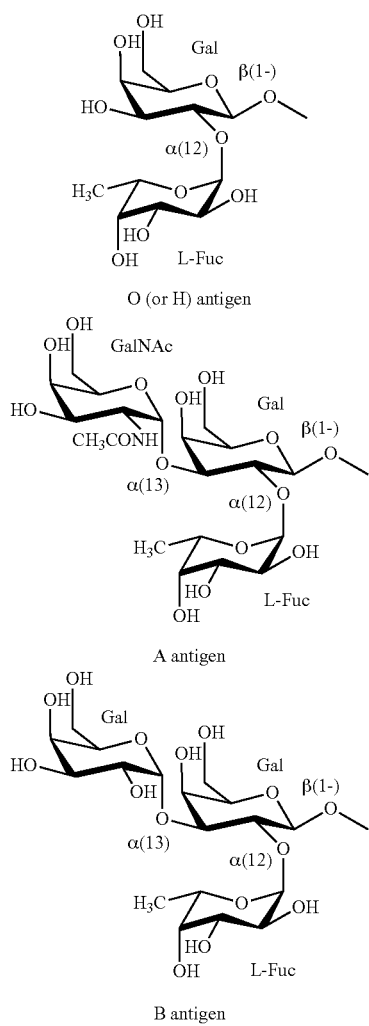

These blood antigens can be further divided into subtypes based on linkage arrangement. Other blood group subtypes include blood group antigens that are expressed on different core saccharide chain types. Core saccharides chain types can include type 1, type 2, type 3 and type 4 glycan precursors. Exemplary blood group antigen oligosaccharides include the following:

Blood group A antigens on types 1-4 include:

A type 1 GalNAcα1,3(Fucα1,2)Galβ1,3GlcNAcβ1

A type 2 GalNAcα1,3(Fucα1,2)Galβ1,4GlcNAcβ1

A type 3 GalNAcα1,3(Fucα1,2)Galβ1,3GalNAcα1

A type 4 GalNAcα1,3(Fucα1,2)Galβ1,3GalNAcβ1.

Blood group B antigens on types 1-4 include:

B type 1 Galα1,3(Fucα1,2)Galβ1,3GlcNAcβ1

B type 2 Galα1,3(Fucα1,2)Galβ1,4GlcNAcβ1

B type 3 Galα1,3(Fucα1,2)Galβ1,3GalNAcα1

B type 4 Galα1,3(Fucα1,2)Galβ1,3GalNAcβ1.

Carbohydrates are attached to pHLIP® such that the carbohydrate is positioned outside of the cell in the extracellular space, i.e., the carbohydrate is attached to the membrane non-inserted portion of pHLIP® (FIGS. 5A and 5B). Preferably, the carbohydrate is not delivered into the cytoplasm of the target cell, e.g., tumor or otherwise diseased cell. In some examples, the carbohydrate is attached to the N-terminal part of the pHLIP®. In other examples, e.g., reverse linear pHLIP® sequences (see tables below), the C-terminus of pHLIP® stays outside of the cell and N-terminus will insert into the membrane; thus, in such an example, the carbohydrate is attached to the C-terminal part of the pHLIP®. Cyclic pHLIPs, which have no N-terminus can also be used, provided that the carbohydrate moiety remains outside of the cell, e.g., exposed to the extracellular space. In preferred embodiments, the carbohydrate is not attached to the membrane-inserting end of the pHLIP® peptide.

For example, an A antigen (or its part, e.g., epitope portion thereof) conjugated with membrane non-inserting part of pHLIP® could be used in patients with blood groups B and O; or a B antigen (or its part) conjugated with membrane non-inserting part of pHLIP® could be used in patients with blood groups A and O; patients with blood group AB need infusion of antibodies (isohemagglutinins). Exemplary structures below are examples of derivatives of synthetic type 2 A antigen epitope, B antigen epitope and O antigen epitope ready for conjugation with membrane non-inserting part of pHLIP®:

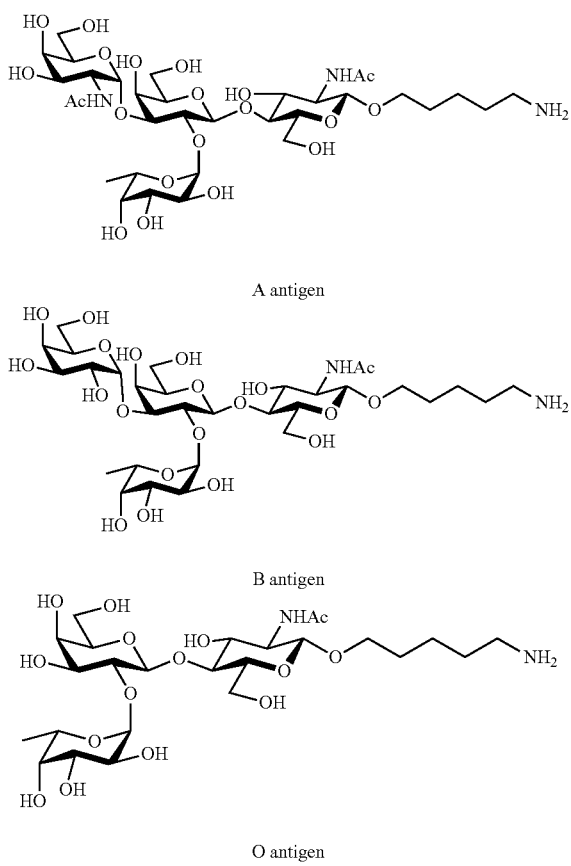

A antigen

B antigen

O antigen

As described herein, the blood antigen may be conjugated with the membrane non-inserting part of the pHLIP® peptide, i.e., a portion of pHLIP® peptide that is exposed on the outside of the cell.

Also provided herein are methods for promoting an immune response. For example, the method comprises administering a composition comprising a carbohydrate epitope conjugated to a pHLIP® peptide comprising at least 4 amino acids. The pHLIP® peptide positions a carbohydrate epitope, or two carbohydrate epitopes or multiple carbohydrate epitopes on the surfaces of the targeted cells in a diseased tissue to induce an immune response predominantly targeting diseased tissue. Furthermore, the carbohydrate epitope interacts with endogenous antibodies and proteins, e.g., pre-existing antibodies and proteins in the subject's body or antibodies activated by immunization or a boost, which then induce an immune response. An epitope is a molecular region of an antigen capable of eliciting an immune response and of combining with a specific antibody or immune cell produced by such a response. An epitope is also known as an antigenic determinant. For example, an epitope is a part of an antigen molecule to which an antibody attaches or to which an immune cell attaches.

Furthermore, provided herein are methods of treating a diseased tissue with a naturally acidic extracellular environment or a tissue with an artificially induced acidic extracellular environment relative to normal physiological pH in a subject. For example, the diseased tissue includes a cancerous tissue or a tumor. As described above, the composition recruits the subject's endogenous antibodies and proteins to induce an immune response, and thereby treats the diseased tissue in the subject. The immune response can include, for example, initiation of complement-dependent cytotoxicity (CDC), antibody-dependent cell-mediated cytotoxicity (ADCC), or the release of cytokines or inflammatory mediators to promote T-cell or NK-cell responses.

Also within the invention is a method of augmenting an immune response, comprising administering to a subject a composition comprising a carbohydrate epitope and a pHLIP® peptide as described above. In some examples, the composition is administered using methods well known in the art; e.g., the composition is injected directly into a tumor mass. Alternatively, the composition is systemically administered. Formulations comprising a Carb-linker-pHLIP® (where Carb is a carbohydrate epitope) for intravenous, subcutaneous, intraarterial, intraperitoneal, intracerebral, intracerebroventricular, intrathecal, intracardiac, intracavernous, intraosseous, intraocular, or intravitreal administration are also provided. In some examples, a formulation comprises a Carb-linker-pHLIP® for intramuscular, intradermal, transdermal, transmucosal, intralesional, subcutaneous, topical, epicutaneous, extra-amniotic, intravaginal, intravesical, nasal, or oral administration.

The present subject matter also includes a formulation for intravesical instillation comprising a Carb-linker-pHLIP® as disclosed herein. In some embodiments, the formulation is used for the treatment of cancer (e.g., solid tumors) or autoimmune diseases.

Also provided herein is a formulation comprising a Carb-linker-pHLIP® that comprises multiple pHLIP® peptides (see, e.g., FIGS. 3 and 4) for systemic administration. In certain embodiments, the formulation is used for the treatment of cancer or inflammation.

Provided herein is a method of treating cancer or inflammation in a subject, comprising administering to the subject an effective amount of a pH-triggered compound, wherein the compound comprises a carbohydrate epitope, which is delivered by pHLIP® to the surface of the cell. For example, the cancer includes a solid tumor. Non-limiting examples of cancer include colon cancer, prostate cancer, breast cancer, bladder cancer, lung cancer, skin cancer, liver cancer, bone cancer, ovarian cancer, stomach cancer, pancreatic cancer, testicular cancer, and brain cancer. Systemic or blood-borne tumor cells, e.g., cancers of the circulatory system, may also be treated using the carbohydrate-pHLIP® peptide constructs.

The composition preferentially targets a diseased tissue compared to a healthy tissue, thereby minimizing damage to the healthy tissue. For example, the composition selectively promotes an immune response to cells in diseased tissue, e.g., the tumor cell.

Included herein are pharmaceutical compositions comprising a pH-triggered peptide and a pharmaceutically acceptable carrier or excipient (inactive vehicle).

As used herein, "effective" when referring to an amount of a compound refers to the quantity of the compound that is sufficient to yield a desired response without undue adverse side effects (such as toxicity, irritation, or allergic response) commensurate with a reasonable benefit/risk ratio when used in the manner of this disclosure.

In some embodiments, a subject is a mammal. In certain embodiments, the mammal is a rodent (e.g., a mouse or a rat), a primate (e.g., a chimpanzee, a gorilla, a monkey, a gibbon, a baboon), a cow, a camel, a dog, a cat, a horse, a llama, a sheep, a goat, or a pig. In preferred embodiments, the subject is a human.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

DETAILED DESCRIPTION

Figure 1:
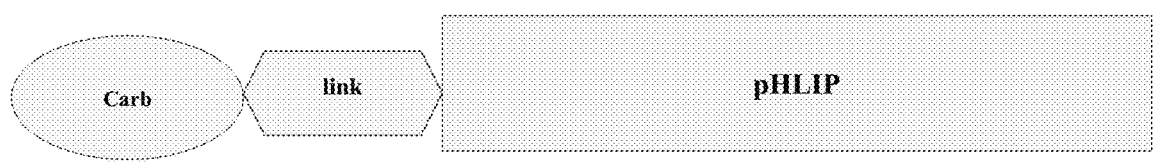
FIG. 1 is a diagram of a pHLIP® construct linked to a carbohydrate epitope via a linker molecule.

Using the immune system to combat disease is a therapeutic strategy that is finding increasingly wide applications, including in the treatment of cancers. Endogenous antibodies circulate in serum of healthy humans naturally, without previous immunization. These antibodies can be directed against the individual's own antigens as well as against foreign antigens. Endogenous antibodies are polyreactive and mostly react with low affinity but high avidity. For example, when a cancer cell is decorated with multiple carb epitopes, then the affinity for the antibody binding to the cell will. Moreover, pHLIP® (as well as other proteins) has free lateral movement in the membrane bilayer, and the affinity of a single epitope-pHLIP to antibody in blood is low. They target cells by recognizing specific signaling molecules (antigens) found on a cell surface. Carbohydrate (saccharide) antigens recruit endogenous (natural) antibodies to initiate CDC (humoral immunity) and ADCC (cellular immunity). In human serum, endogenous (natural) antibodies in total constitute approximately 10% of total serum and about 1% of circulating B lymphocytes in adults are capable of producing these antibodies.

Decoration of target cells with carbohydrate epitopes that can recruit endogenous (natural) antibodies and proteins lead to activation of antibody-dependent cellular cytotoxicity and/or activation of the classical complement cascade to assemble a membrane attack complex that promoted the formation of pores in the target cell membrane and resulted in cell death.

To enhance the abundance of natural antibodies, an immune boost may be performed and the titer can be established by ELISA prior to treatment to ensure the presence of a sufficient amount of specific antibodies in the blood. Also, if needed, immunization followed by a boost is performed to produce sufficient amounts of antibodies against specific carbohydrate epitopes.

Decoration of target cells comprises the addition of purified epitopes, e.g., purified carbohydrates, to the target cell, e.g., to the surface of the target cell. The target cells, e.g., tumor cells or other diseased cells, are modified by the pHLIP®-mediated delivery of such purified carbohydrate epitopes to the cells such that the cells are characterized by the presence of a purified carbohydrate moiety on the cell surface, e.g., decorated. The carbohydrate moiety may be different from those carbohydrate moieties that are present on the target cell prior to modification of the cells as described herein. By virtue of the presence of the delivery mediated by pHLIP®, a heterologous carbohydrate is put/displayed at the surface of the target cell.

A heterologous carbohydrate is one that the target cell did not display on its cell surface prior to treatment using the methods and compositions described herein. For example, the target cell does not make, express, or present on its surface in a naturally-occurring state. Alternatively, the target cell makes, expresses, or displays/presents the carbohydrate prior to intervention/modification and/ir treatment; however, the expression or presence on the cell surface is low or undetectable. Treatment according to the invention renders the cell with at least 10%, 20%, 50%, 75%, 2-fold, 5-fold, 10-fold or more of the carbohydrate moiety (purified epitope or antigen) on the surface of the treated (tumor or otherwise diseased) cell. Exemplary carbohydrates are those to which the subject/patient comprises antibodies, e.g., IgG or IgM isotype antibodies, which could are identified by an antibody titer test before administration of the construct.

Decoration of Diseased Cells with Carbohydrate Antigens

Specific decoration of target cells (diseased cells characterized by acidic cell surface microenvironment) with carbohydrate epitopes to recruit endogenous (natural) antibodies and proteins, to induce an immune response is a useful approach in the treatment of tumors and other diseased tissues. However, the importance for successful treatment (and an advantage of the system described herein) is in the ability to activate an immune response predominantly in diseased tissue (tumors) and guiding the immune reaction away from normal tissues, thereby avoiding adverse/undesirable side effects.

A selected carbohydrate epitope is delivered to and positioned on cell surfaces (decoration) predominantly in targeted diseased tissues, such as tumors. The delivery to and addition of the carbohydrate epitopes to tumor cells and other diseased (acidic) cells and tissues is a great advantage, because the system selectively induces immune responses predominantly within the diseased tissues. The carbohydrate antigens are preferentially inserted into the cell membranes of diseased, e.g., tumor cells compared to surrounding or bordering normal, e.g., non-tumor, cells. pHLIP® peptides conjugated to carbohydrate molecules reliably and effectively accomplish this task.

Acidic diseased cells (tumor cells) are decorated, e.g., modified, using carbohydrate (saccharide) epitopes conjugated to the pHLIP®, so that the pHLIP® will target tumors by responding to cell surface acidity, insert into tumor cell membranes, and locate enough amount of specified carbohydrate epitopes on the cell surface for efficient recruitment of natural antibodies and proteins, and induction of immune response predominantly in the diseased tissue.

pHLIP® conjugated to polar carbohydrate molecules are typically cleared by the kidney, where there is minimal or no risk of developing an immune reaction since antibodies (large molecules like IgM and IgG antibodies) are excluded from the kidney by their size.

Carbohydrate-pHLIP® Constructs

Figure 3:
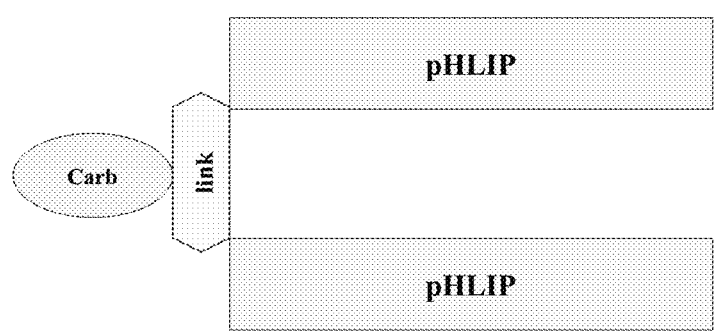
FIG. 3 is a diagram of a pHLIP® construct with 2 (or more) pHLIP peptides linked together via a linker molecule.
Figure 4:
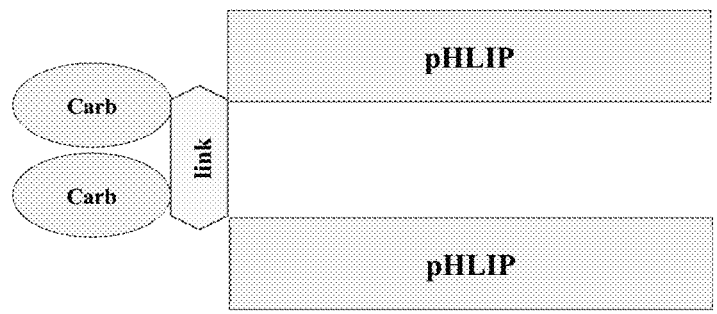
FIG. 4 is a diagram of a pHLIP® construct with 2 (or more) carbohydrate epitopes and 2 (or more) pHLIP® peptides linked together via a linker molecule.
Figure 5A:
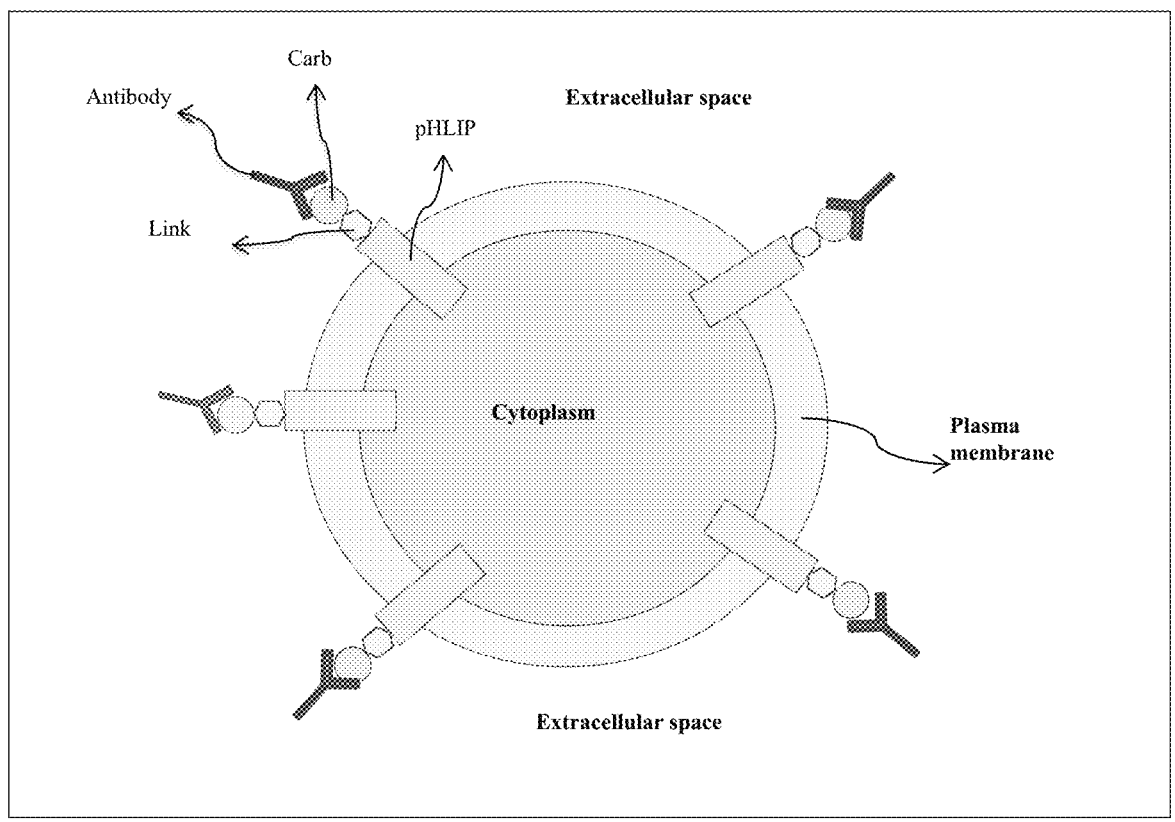
FIG. 5A is a schematic presentation of carbohydrate epitope tethered/attached to the surface of cell by pHLIP®. For example, the carbohydrate will be located close to the cell surface. As a result, the targeted cell becomes decorated with carbohydrate epitopes and endogenous antibodies recognize and bind to the epitope to promote an immune reaction. The immune reaction mediates rejection or destruction of the diseased tissue, e.g., tumor cell.
Figure 5B:
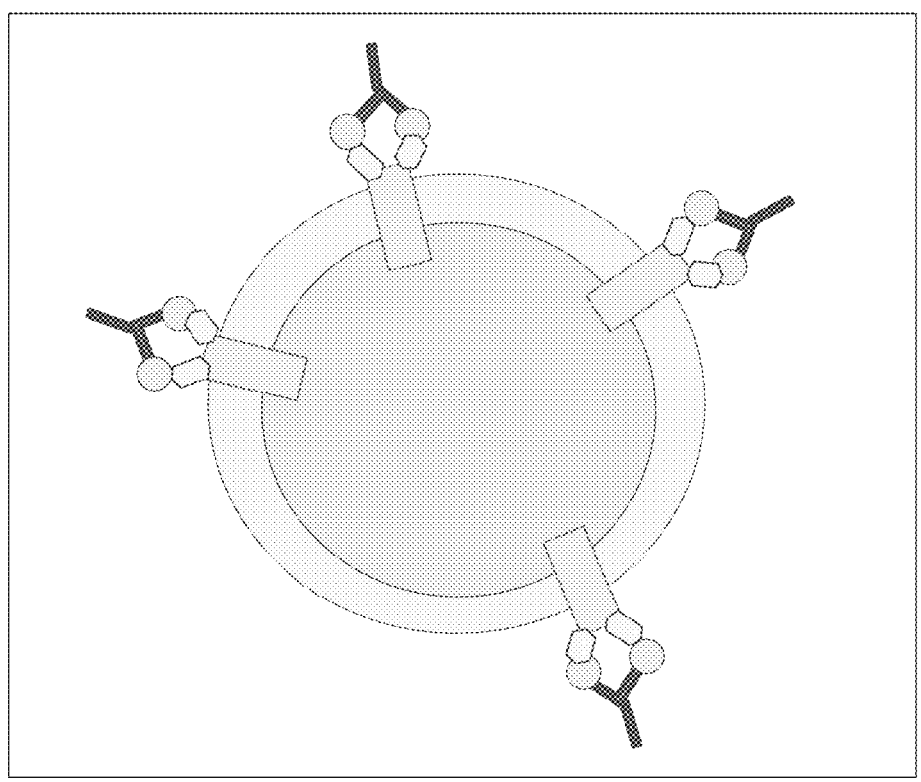
FIG. 5B is a schematic presentation of two carbohydrate epitopes tethered to the surface of a cell by pHLIP®. As a result, the targeted cell becomes decorated with carbohydrate epitopes and the two heads of an endogenous antibody can recognize and bind to either or both epitope(s) to promote an immune reaction. The immune reaction mediates rejection or destruction of the diseased tissue, e.g., tumor cell (targeted cell). The distance between the two carbohydrate epitopes (e.g., ~10 nm) is such that the two heads of an antibody can each bind to an epitope.
Figure 6:
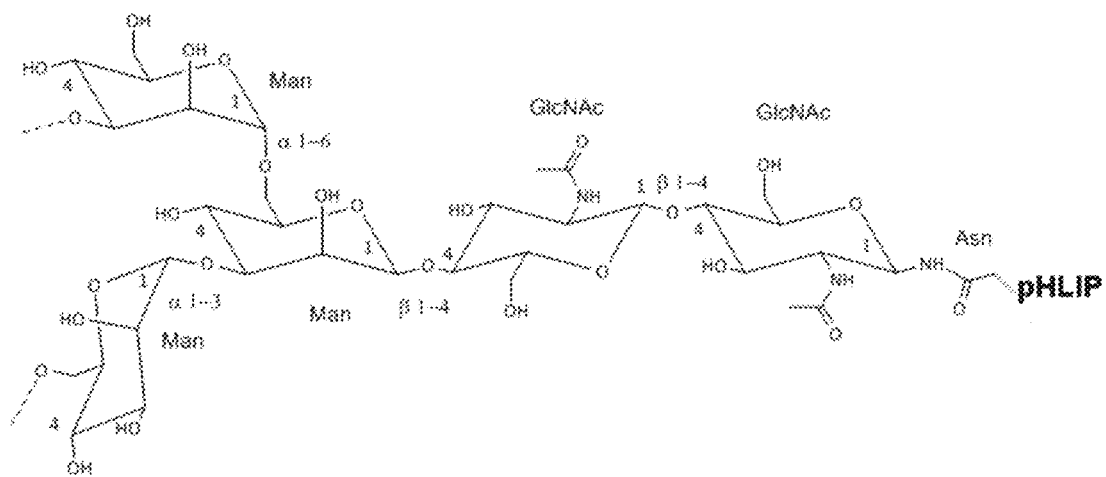
FIG. 6 is a diagram of Mannose-N-acetylgalactosamine [(Man)$_3$(GlcNAc)$_2$] covalently attached to a pHLIP® peptide.
Figure 7A:
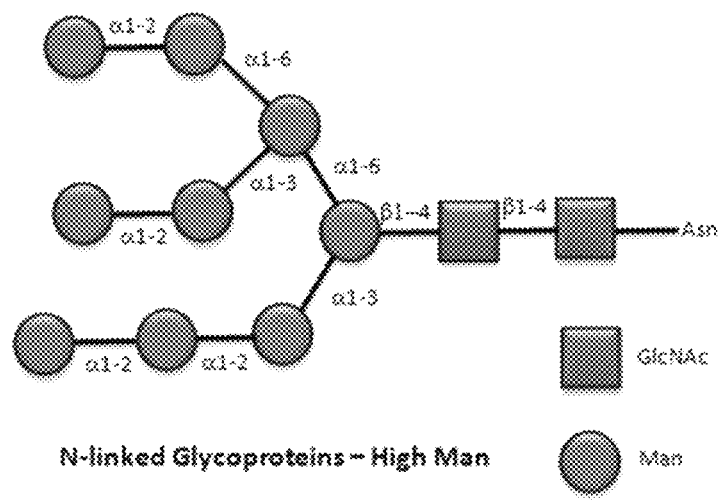
FIG. 7A is a diagram of a high mannose N-linked glycoprotein.
Figure 7B:
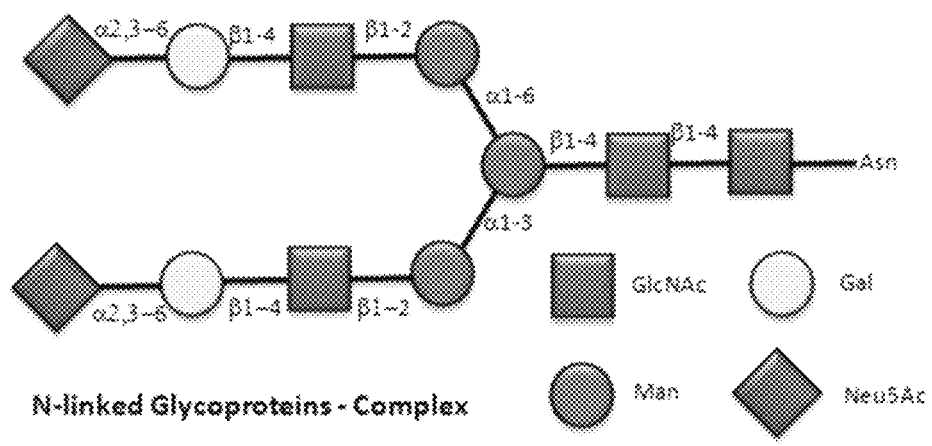
FIG. 7B is a diagram of a complex N-linked glycoprotein.
Figure 7C:
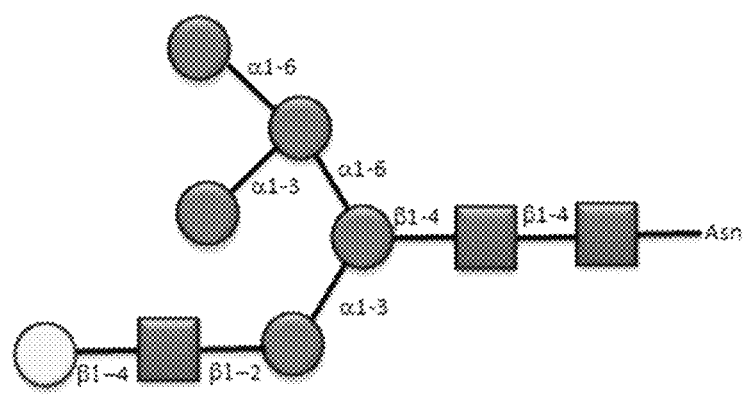
FIG. 7C is a diagram of a mixed (hybrid) N-linked glycoprotein.
Figure 8:
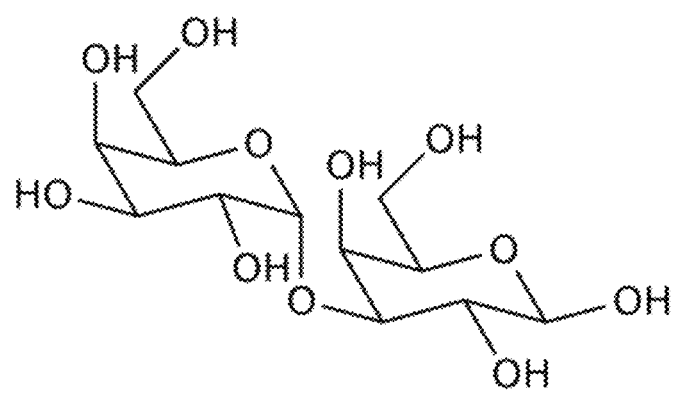
FIG. 8 is a diagram of Galactose-α-1,3-Galactose (αGal).
Figure 9A:
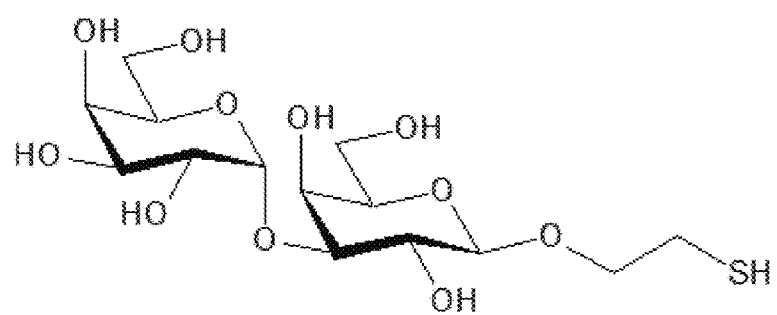
FIG. 9A is a diagram of Galactose-α-1,3-Galactose (αGal) di-Gal derivative with a free sulfur (SH) group for conjugation (e.g., covalently attached) with a pHLIP® peptide.
Figure 9B:
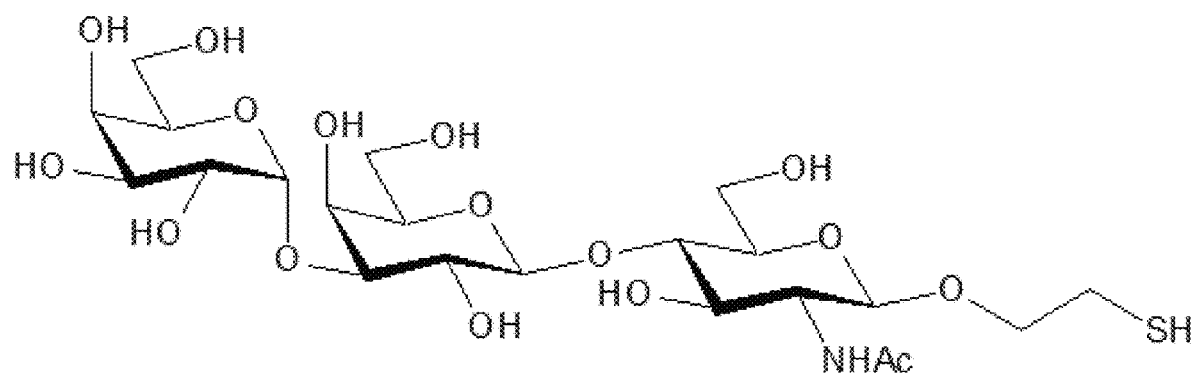
FIG. 9B is a diagram of Galactose-α-1,3-Galactose (αGal) tri-Gal (3 Gal units) derivative with free sulfur (SH) group for conjugation with a pHLIP® peptide.
Figure 10:
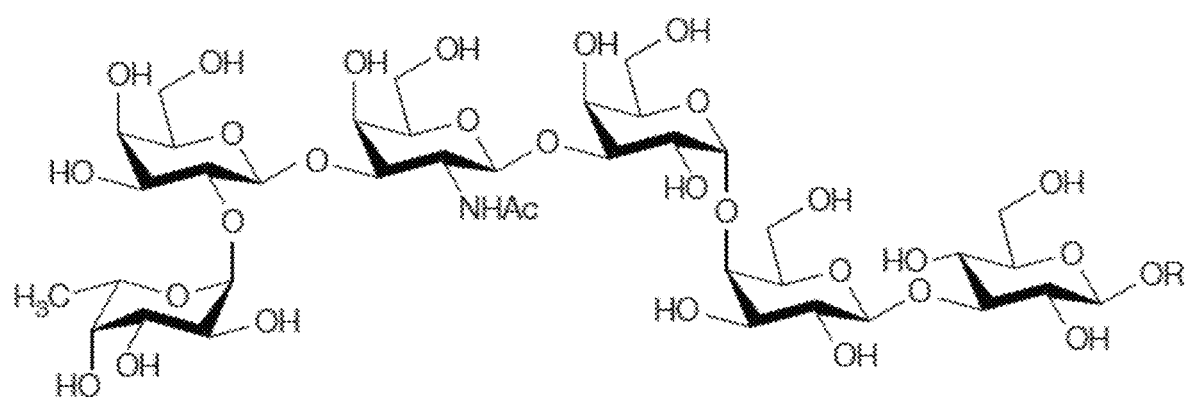
FIG. 10 is a diagram of the Globo H hexasaccharide epitope. For example, the "R" group may be a point of attachment.
Figure 11:
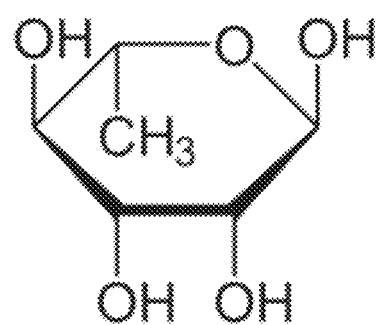
FIG. 11 is a diagram of the L-form, α-rhamnose (see FIG. 15 for site of conjugation).
Figure 12:
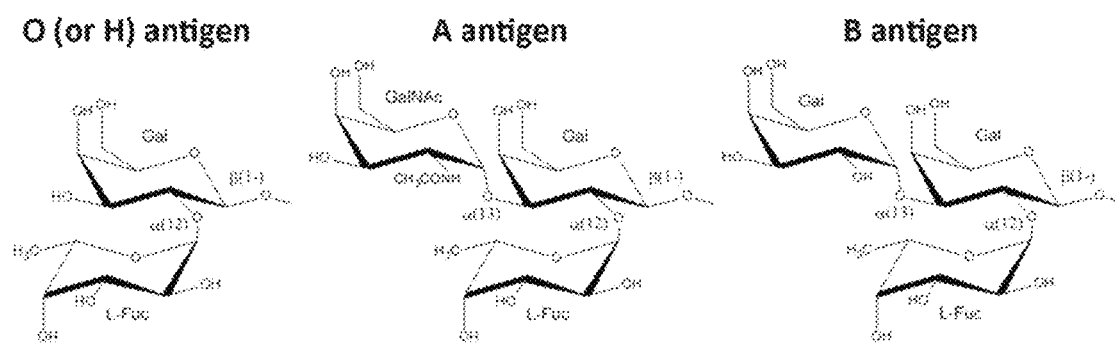
FIG. 12 is a diagram of core saccharide parts of O (or H) antigen, an A antigen, and a B antigen
Figure 13:
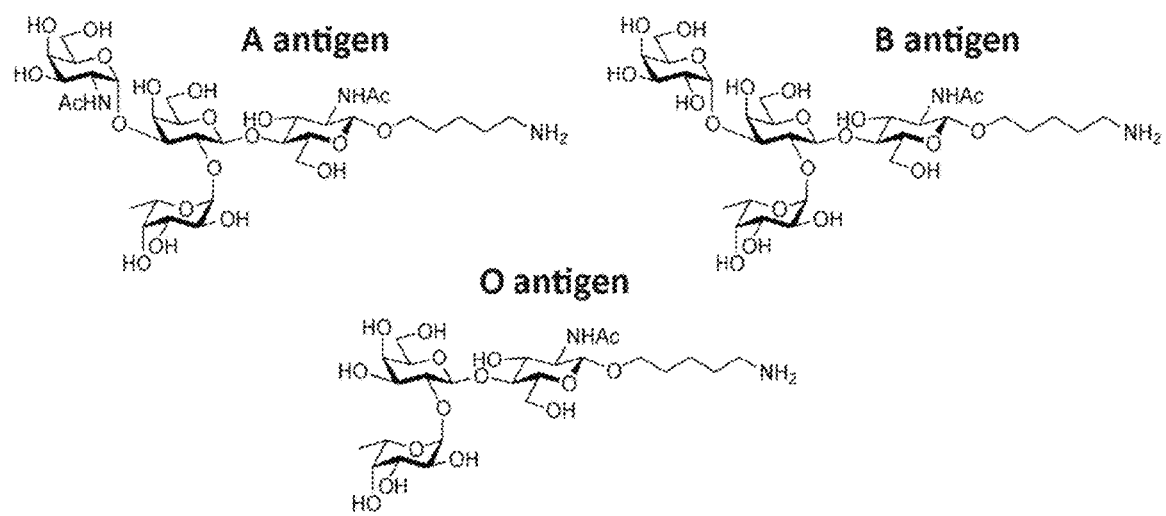
FIG. 13 is a diagram of exemplary structures of derivatives of a synthetic type 2 A antigen, a B antigen and an O antigen ready for conjugation with pHLIP® peptide, for example, antigens have a free amine, meaning that a NHS-malimide linker may be used to lin to the Cys of pHLIP (e.g., not the N-terminus).
Figure 14:
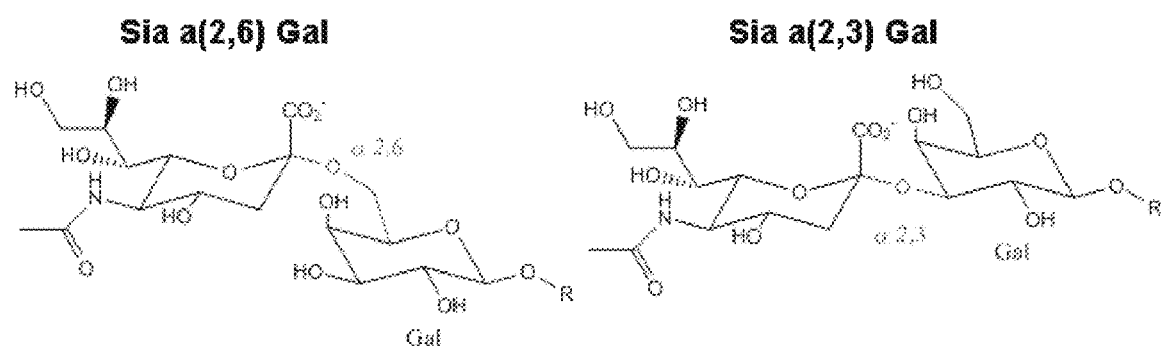
FIG. 14 is a diagram of an exemplary sialic acid antigen for binding with hemagglutinin.
Figure 15:
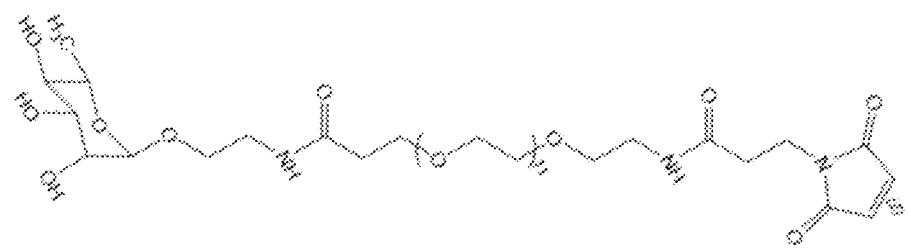
FIG. 15 is a diagram of the chemical structure of L-rhamnose coupled with PEG12-malimide for conjugation with pHLIP containing single Cys residue.
Figure 16:
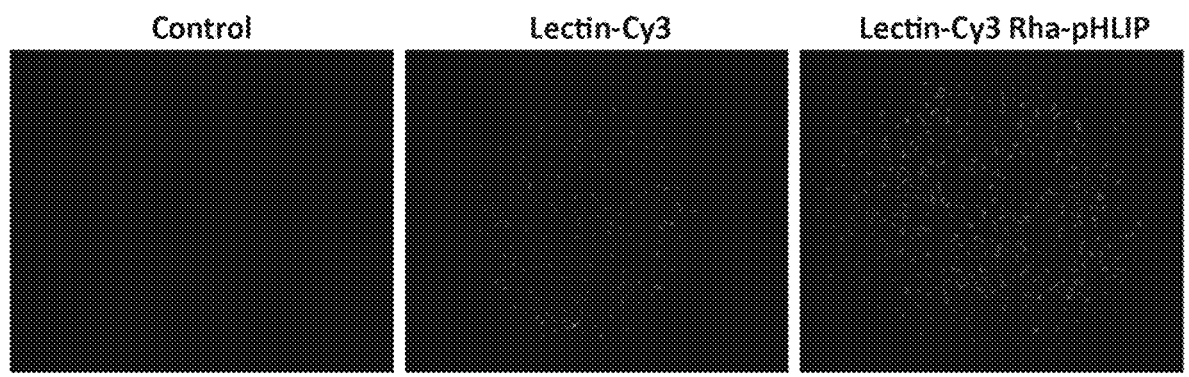
FIG. 16 depicts fluorescent (Cy3) images obtained from tumor spheroids: left—non-treated (control), middle—treated with lectin-Cy3 followed by washing (Lectin-Cy3) or right—treated with Rha-pHLIP® (e.g., with L-rhamnose) followed by washing and treatment with Lectin-Cy3 followed again by washing (Lectin-Cy3 Rha-pHLIP®).

General representations of pHLIP® compositions/constructs comprising pHLIP® peptide and a carbohydrate antigen/epitope for cell surface delivery of the carbohydrate antigen/epitope is shown in FIGS. 1, 2A-2B, 3 and 4. FIG. 5A and FIG. 5B are schematic presentations of carbohydrate epitope(s) tethered (positioned close to the cell membrane) to the surface of cell by pHLIP®, as a result, the targeted cell becoming decorated with carbohydrate epitopes and endogenous (natural) antibodies can recognize and bind epitope to promote immune reaction.

Compositions include those with the following general structure:

Carb-Linker-Peptide

"Carb" comprises a carbohydrate epitope to induce immune response by attracting of endogenous antibodies, which then mediate an immune response that leads to killing of the tumor or otherwise diseased cell. Non-limiting examples of carbohydrate epitopes are described below. "Peptide" is a pHLIP® peptide (a non-limiting example is a pHLIP® comprising the sequence AXDDQNPWRAYLDLLFPTDTLLLDLLWA (SEQ ID NO: 3), or AXDQDNPWRAYLDLLFPTDTLLLDLLWA (SEQ ID NO: 475), or AX(Z)$_n$XPWRAYLDLLFPTDTLLLDLLWA (SEQ ID NO: 5), where "X" is a functional group (e.g., for conjugation purposes), selected from lysine (Lys), cysteine (Cys), serine (Ser), threonine (Thr) an Azido-containing amino acid, and "Z" indicates any amino acid residue and n is any integer between 1 and 10 and including 1 and 10 (e.g., $1 \leq n \leq 10$).

For example, $(Z)_n$ could be QDNDQN (SEQ ID NO: 6) or any combination of polar residues, e.g., D, E, N or Q. In some cases, "Peptide" is a pHLIP® conjugate, where a pHLIP peptide is linked with a therapeutic or drug molecule for intracellular delivery. In some cases, "Peptide" is a linear or cyclic pH-sensitive peptide.

"Linker" comprises a covalent bond or a chemical linker. A non-limiting example of linker is a PEG polymer or a flexible extension of the pHLIP® peptide membrane non-inserting end ranging in size from 200 Da to 20 kDa. In some examples, the pHLIP® peptide membrane non-inserting end can comprise of, for example from 3 to about 20-30 glycine residues (a poly-Gly). The purpose of a polymer or a polypeptide extension is to position epitope at surface of cells and enhance access of antibodies or proteins for binding with the epitope. The size and hydrophobicity of the linker ensures renal clearance of the construct and does not promote hepatic clearance. Linkers include non-cleavable linkers that are stable in the blood. The carbohydrate epitope(s) is preferably linked to pHLIP® peptide(s) via non-cleavable link(s), e.g., covalent bond. In examples, the linker is preferably polar or moderately hydrophobic.

A compound is characterized as polar if it has a measured log P of less than about 1. For example, polarity and hydrophobicity are characterized as follows. Polar: Log P<−0.4; Moderately hydrophobic: 2.5<Log P<−0.4; and Hydrophobic: Log P>2.5. The polarity and/or hydrophobicity of a drug or compound to be delivered is measured using methods known in the art, e.g., by determining Log P, in which P is octanol-water partition coefficient. A substance is dissolved into octanol-water mixture, mixed and allowed to come to equilibration. The amount of substance in each (or one) phases is then measured. The measurements themselves can be made in a number of ways known in the art, e.g., by measuring absorbance, or determining the amount using NMR, HPLC, isotopic labeling or other known methods.

Figure 2A:
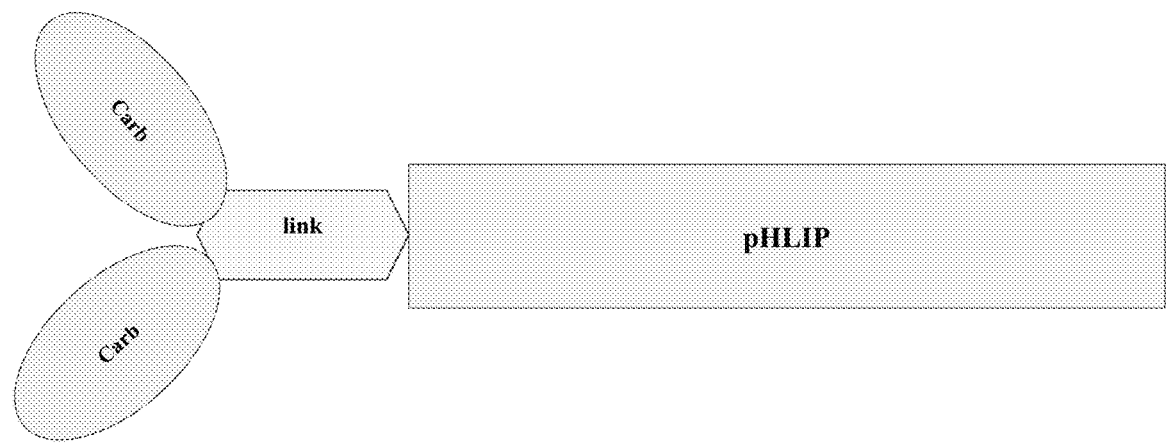
FIG. 2A is a diagram of a pHLIP® construct linked to 2 (or more) carbohydrate epitopes via linker molecules.
Figure 2B:
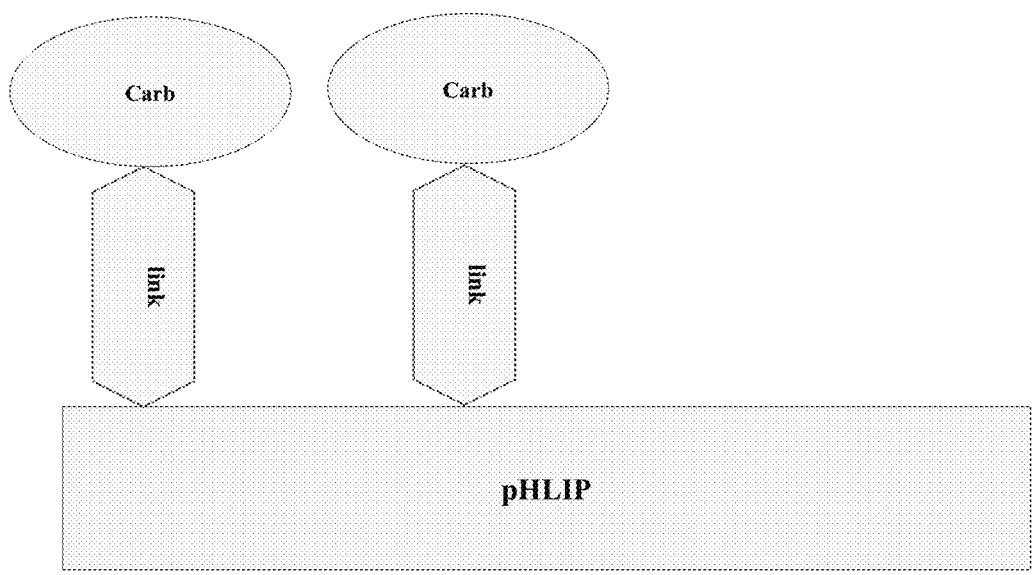
FIG. 2B is a diagram of a pHLIP® construct with 2 carbohydrate epitopes linked to pHLIP® peptide via linker molecules.

An exemplary construct with a carbohydrate epitope linked to a pHLIP® is shown in FIG. 1. An exemplary construct with multiple carbohydrate epitopes linked to a single pHLIP® is shown in FIGS. 2A and 2B. FIG. 2B shows two carbohydrate epitopes positioned on the pHLIP® peptide in such a way that the two heads of a single antibody molecule bind to the two epitopes. An exemplary construct with a carbohydrate epitope linked to multiple pHLIP®s are shown in FIG. 3, and an exemplary construct with carbohydrate epitopes linked to multiple pHLIP®s are shown in FIG. 4.

Aspects of the present subject matter relate to the surprising discovery that pH-triggered peptides specifically interact with the lipid bilayer of liposomal and cellular membranes and, as such, when conjugated to a carbohydrate epitope, can decorate the liposome or cell with these carbohydrate epitopes. Moreover, pH-triggered peptides can target acidic tissue, and as such, when conjugated to a carbohydrate epitope, can target it to the surface of cells in acidic diseased tissue. The carbohydrate epitopes can recruit endogenous (natural) antibodies and proteins, and induce an immune response.

The compositions and methods described herein are a very attractive approach in the treatment of tumors and other diseased tissues. The importance for successful treatment rests in the ability to activate an immune response predominantly in diseased tissue (tumors) and guiding the immune reaction away from normal tissues and avoiding side effects.

The compositions and methods described herein provide a solution and strategy in which selected carbohydrate (saccharide) epitopes are positioned on cell surfaces predominantly in targeted diseased tissues, such as tumors. The invention provides decoration of targeted acidic diseased cells (tumor cells) using carbohydrate (saccharide) epitopes conjugated to the pHLIP®, so that the pHLIP® targets tumors by responding to cell surface acidity, inserting into tumor cell membranes, and locating enough of the specified carbohydrate epitopes on the cell surface for efficient recruitment of endogenous or natural antibodies and proteins, and induction of immune response predominantly in the diseased tissue. This can provide a great advantage to selectively induce immune responses predominantly within the diseased tissues.

The pHLIP® peptide conjugated to carbohydrate epitopes (e.g., polar carbohydrate molecules) are typically cleared by kidney, where there is little to no risk of developing an immune reaction since antibodies (e.g., large molecules like IgM and IgG) are excluded from the kidney by their size.

Cellular Immune Responses

Humoral immunity is an aspect of immunity that is mediated by macromolecules found in extracellular fluids, such as secreted antibodies and complement proteins. The immune system is divided into a more primitive innate immune system and an acquired or adaptive immune system of vertebrates, each of which contains humoral and cellular components. Humoral immunity refers to antibody production and the accessory processes that accompany it, including: Th2 activation and cytokine production, germinal center formation and isotype switching, affinity maturation and memory cell generation. It also refers to the effector functions of antibodies, which include pathogen and toxin neutralization, classical complement activation, and promotion of phagocytosis and pathogen elimination.

The complement system is a biochemical cascade of the innate immune system that helps clear pathogens from an organism. It is derived from many small blood plasma proteins that work together to disrupt the target cell's plasma membrane leading to cytolysis of the cell. The complement system is involved in the activities of both innate immunity and acquired immunity.

Activation of this system leads to cytolysis, chemotaxis, immune clearance, and inflammation, as well as the marking of pathogens for phagocytosis. The proteins account for 10% of the serum globulin fraction.

Three biochemical pathways activate the complement system: the classical complement pathway, the alternate complement pathway, and the mannose-binding lectin pathway. The classical complement pathway typically requires antibodies for activation and is a specific immune response, while the alternate pathway can be activated without the presence of antibodies and is considered a non-specific immune response.

Immunoglobulins are glycoproteins in the immunoglobulin superfamily that function as antibodies. The terms antibody and immunoglobulin are often used interchangeably. They are found in the blood and tissue fluids, as well as many secretions. In structure, they are large Y shaped globular proteins. In mammals there are five types of antibody: IgA, IgD, IgE, IgG, and IgM. Each immunoglobulin class differs in its biological properties and has evolved to deal with different antigens. Antibodies are synthesized and secreted by plasma cells that are derived from the B cells of the immune system.

An antibody is used by the acquired immune system to identify and neutralize foreign objects like bacteria and viruses. Each antibody recognizes a specific antigen unique to its target. By binding their specific antigens, antibodies can cause agglutination and precipitation of antibody-antigen products, prime for phagocytosis by macrophages and other cells, block viral receptors, and stimulate other immune responses, such as the complement pathway.

An incompatible blood transfusion causes a transfusion reaction, which is mediated by the humoral immune response. This type of reaction, called an acute hemolytic reaction, results in the rapid destruction (hemolysis) of the donor red blood cells by host antibodies. The cause is usually a clerical error, such as the wrong unit of blood being given to the wrong patient. The symptoms are fever and chills, sometimes with back pain and pink or red urine (hemoglobinuria). The major complication is that hemoglobin released by the destruction of red blood cells can cause acute renal failure.

Another example is organ transplant rejection. The major problem of xenotransplantation (transplantation of organs between different species, such as, for example, pigs to humans) is strong reaction of natural antibodies, predominantly IgG and IgM, to a terminal carbohydrate ($\alpha$Gal) on glycolipids or glycoproteins, which appears to be ubiquitously expressed in most tissues in all species except man, the great apes and old world monkeys. Hyperacute rejection of an organ is mediated by antibody and complement, and results in rapid destruction of the organ.

The compositions and methods described herein (e.g., the pHLIP® peptide conjugated to a carbohydrate epitope on the surface of target cells) can recruit endogenous (natural) antibodies to initiate complement-dependent cytotoxicity.

This can lead to the activation of the classical complement cascade to assemble a membrane attack complex that promotes the formation of pores in the target cell membrane and results in cell death. The activation of the complement cascade can further amplify immune response through the release of cytokines and inflammatory mediates. These signaling molecules attract immune cells involved in antibody-dependent cell-mediated toxicity, described below.

Cellular Immunity

The antibody-dependent cellular cytotoxicity (ADCC), also referred to as antibody-dependent cell-mediated cytotoxicity, is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection.

ADCC is independent of the immune complement system that also lyses targets but does not require any other cell. ADCC requires an effector cell which classically is known to be natural killer (NK) cells that typically interact with IgG antibodies. However, macrophages, neutrophils and eosinophils can also mediate ADCC, such as eosinophils killing certain parasitic worms known as helminths via IgE antibodies. ADCC is part of the adaptive immune response due to its dependence on a prior antibody response.

The compositions and methods described herein (e.g., the pHLIP® peptide conjugated to a carbohydrate epitope on the surface of target cells) can recruit natural antibodies to initiate ADCC. This recruitment of antibodies leads to the activation of the classical complement cascade to assemble a membrane attack complex that promotes the formation of pores in the target cell membrane and results in cell death. The activation of the complement cascade can further amplify immune responses through the release of cytokines and inflammatory mediators. These signaling molecules attract immune cells involved in ADCC such as neutrophils, macrophages, and NK cells. Immune effector cells, recognizing surface-bound antibodies, initiate ADCC through activating Fc receptors. In human serum, natural antibodies in total constitute approximately 10% of total serum and about 1% of circulating B lymphocytes in adults is capable of producing these antibodies.

Blood Group Antigens

Blood is classified into different groups according to the presence or absence of molecules called antigens. As described by Dean L., an antigen is any substance to which the immune system can respond (Dean L "Blood Groups and Red Cell Antigens: Chapter 2-Blood group antigens are surface markers on the red blood cell membrane; National Center for Biotechnology Information; 2005). If the immune system encounters an antigen that is not found on the body's own cells, it will launch an attack against that antigen. Conversely, antigens that are found on the body's own cells are known as "self-antigens", and the immune system does not normally attack these. When patients receive blood transfusions, their immune systems will attack any donor red blood cells that contain antigens that differ from their self-antigens. Therefore, ensuring that the antigens of transfused red blood cells match those of the patient's red blood cells is essential for a safe blood transfusion.

Blood group antigens are either sugars or proteins, and they are attached to various components in the red blood cell membrane. In examples, the antigens of the ABO blood group are sugars. The ABO blood type is controlled by a single gene (the ABO gene) with three types of alleles. The gene encodes a glycosyltransferase—that is, an enzyme that modifies the carbohydrate content of the red blood cell antigens. The antigens of the ABO blood group are produced by a series of reactions in which enzymes catalyze the transfer of sugar units. A person's DNA determines the type of enzymes they have, and, therefore, the type of sugar antigens that end up on their red blood cells.

Blood group antigens include (A, B, and O (H)). The blood group antigens are specific for all the blood group subtypes. Patients with blood group A have B antibodies in their blood, patients with blood group B have A antibodies in their blood, patients with blood group AB have no antibodies against A and B antigens in their blood, and patients with blood group O have both A and B antibodies in their blood.

The human ABO blood group system is defined by the presence or absence of specific antigens at blood cell surface. These unique carbohydrate or carbohydrate combinations found on the membrane of red blood cells (RBCs) define a person's blood type. The RBCs of a blood type O individual have on their surface the O-antigen, the sugar fucose, arranged in a long repeating chain. The RBCs of a blood type A individual have on their surface the base sugar fucose plus the carbohydrate N-acetyl galactosamine, the A antigen. The RBCs of a blood type B individual have on their surface the base sugar fucose plus the carbohydrate galactose (also called D-galactosamine), the B antigen. The RBCs of a blood type AB individual have on their surface the base sugar fucose plus both the A and B antigens, i.e. both N-acetyl galactosamine and galactose. These RBC antigens are called isoantigens, a term for proteins or other substances that are present in only some members of a species and therefore able to stimulate antibody production in other members of the same species who lack the antigen. Humans who are exposed to foreign isoantigens, and antigens very similar thereto, produce antibodies that respond to the A and/or B antigens absent from their own RBCs. These are termed isoantibodies, and more specifically, isoagglutinins, the term for antibodies normally present in the sera of individuals that cause agglutination of the RBCs of another individual of the same species.

The immune system of a person of blood type A recognizes as foreign and will react to exposure to the B antigen, galactose, and produce anti-galactose antibody, called anti-B antibody or anti-B isoagglutinin. Likewise, the immune system if a person of blood type B will react to exposure to the A antigen, n-acetyl galactosamine, and will produce anti-N-acetyl galactosamine antibody, called anti-A antibody or anti-A isoagglutinin. The immune system of a person of blood type AB will not react to exposure to either the A or B antigens, galactose or n-acetyl galactosamine, and produces no antibodies to them. In contrast, a person of blood type O recognizes both the A or B antigens, galactose or n-acetyl galactosamine, as foreign, and will produce both anti-A and anti-B antibodies/isoagglutinins.

The A and B antigens found in the molecules of human RBCs also exist in other biological entities, notably, bacterial cell walls, plants, and other foodstuffs. Bacteria are widespread in the environment, are present in intestinal flora, dust, food and other widely distributed agents, ensuring a constant exposure of individuals to A and B antigens and antigens that are extremely similar to each of these antigens. Many antigens or proteins in foods, such as lectins, have A-like or B-like characteristics and may likewise trigger an immune response and isoagglutinin production. This may explain why individuals who have not been otherwise exposed to antigen, for instance to incompatible blood via transfusion, will have a detectable isoagglutinin level in the blood stream. Isoagglutinin production may be a reaction to environmental provocations of antigens. Small amounts of A and B antigens may enter the body in food, bacteria, or by other means, and these substances initiate the development of isoagglutinins, e.g. the anti-A antibodies and/or anti-B antibodies. See, e.g., Guyton, A. C., Textbook of Medical Physiology 8th ed., W.B. Saunders Co., 1990.

Isoagglutinin production is generally seen after the first few months of life and continues throughout an individual's life, remaining fairly constant until late in adult life. See, e.g., Liu, Y J et. al., The development of ABO isohemagglutinins in Tawanese. Hum. Hered. July/August, 1996, 46(4):181-4. In the elderly, isoagglutinin production has been found to diminish and it is believed that this is due to the gradual reduction in efficiency of the immune defenses as the cells age. Recent studies measuring isoagglutinin levels suggest that the baseline isoagglutinin levels in children have risen over time. See, e.g., Godzisz, J., Synthesis of natural allohemagglutinins of the ABO blood system in healthy children aged 3 months to 3 years, Rev. Fr. *Tranfus. Immunohematol*, September, 1979, 22(4): 399-412.

In addition to sugars (carbohydrate antigens), the antigens of the Rh blood group are proteins. The Rh blood group system consists of 49 defined blood group antigens, among which the five antigens D, C, c, E, and e are the most important. Rh(D) status of an individual is normally described with a positive or negative suffix after the ABO type (e.g., someone who is A Positive has the A antigen and the Rh(D) antigen, whereas someone who is A Negative lacks the Rh(D) antigen). The terms Rh factor, Rh positive, and Rh negative refer to the Rh(D) antigen only. Antibodies to Rh antigens can be involved in hemolytic transfusion reactions and antibodies to the Rh(D) and Rh(c) antigens confer significant risk of hemolytic disease of the fetus and newborn. Rh antibodies are IgG antibodies which are acquired through exposure to Rh-positive blood (generally either through pregnancy or transfusion of blood products). The D antigen is the most immunogenic of all the non-ABO antigens. Approximately 80% of individuals who are D-negative and exposed to a single D-positive unit will produce an anti-D antibody. The percentage of alloimmunization is significantly reduced in patients who are actively exsanguinating. All Rh antibodies except D display dosage (antibody reacts more strongly with red cells homozygous for an antigen than cells heterozygous for the antigen (EE stronger reaction vs Ee). If anti-E is detected, the presence of anti-c should be strongly suspected (due to combined genetic inheritance). It is therefore common to select c-negative and E-negative blood for transfusion patients who have an anti-E. Anti-c is a common cause of delayed hemolytic transfusion reactions.

Galactose-α-1,3-galactose (α-Gal)

Galactose-α-1,3-galactose (α-Gal) is an oligosaccharide, which, if present on the transplanted organ, can induce hyperacute (immediate), acute vascular (delayed) and cellular (chronic) xenograft transplant rejection. α-Gal moiety (di-Gal—to Gal moieties connected or Tri-Gal—three Gal moieties connected and has a higher affinity to an antibody) is added to cell-surface sugars in animals (e.g., swine) by α-1,3-galactosyltransferase (GalT). Due to a frame shift mutation, this enzyme is not functional in humans or Old World monkeys, and these species make anti-Gal antibodies likely as a response to Gal-positive bacteria that inhabit the gastrointestinal tract. IgM, $IgG_2$, and IgA are antibodies specific to α-Gal presented as both glycoprotein and glycolipid. Glycoconjugates range from a single terminal α-Gal epitope up to eight branches with terminal α-Gal epitopes.

Hyperacute xenograft rejection is a response mediated by human natural IgM antibodies that cross-react with α-Gal expressed on the animal endothelial cells and activates the recipient's complement system and destroying the graft.

Acute vascular rejection results in the loss of the xenograft in a few days or weeks after transplantation. The antibody induces constant activation of the vascular endothelium, which leads to elevated expression of procoagulant proteins, cell adhesion molecules, and cytokines. Clinically, microvascular thrombosis results in focal ischemia (local loss of blood supply) and xenograft rejection.

Cellular xenograft rejection is due to the vigorous attack of human cytotoxic T-cells and natural killer (NK) cells such that the graft is lost several weeks after transplantation. In addition, human NK cells have activatory receptors that recognize α-Gal epitope.

The compositions (e.g., Carb-pHLIP® peptide constructs) and methods described herein utilize one or a plurality of α-Gal epitope(s) selectively tethered via a pHLIP® peptide to the surface of cells within diseased tissues (tumors) and induce immune activation and "tumor rejection".

Glycosylation

Glycosylation is the reaction in which a carbohydrate is attached to a hydroxyl or other functional group of another molecule (a glycosyl acceptor). Glycosylation refers in particular to the enzymatic process that attaches glycans to proteins, or other organic molecules. This enzymatic process produces one of the fundamental biopolymers found in cells (along with DNA, RNA, and proteins). Glycosylation is a form of co-translational and post-translational modification. Glycans serve a variety of structural and functional roles in membrane and secreted proteins. The majority of proteins synthesized in the rough endoplasmic reticulum undergo glycosylation. It is an enzyme-directed site-specific process, as opposed to the non-enzymatic chemical reaction of glycation. Glycosylation is also present in the cytoplasm and nucleus as the O-GlcNAc modification. Five classes of glycans are produced:

N-linked glycans attached to a nitrogen of asparagine or arginine side-chains. N-linked glycosylation requires participation of a special lipid called dolichol phosphate.

O-linked glycans attached to the hydroxyl oxygen of serine, threonine, tyrosine, hydroxylysine, or hydroxyproline side-chains, or to oxygens on lipids such as ceramide phosphoglycans linked through the phosphate of a phosphoserine;

C-linked glycans, a rare form of glycosylation where a sugar is added to a carbon on a tryptophan side-chain glypiation, which is the addition of a GPI anchor that links proteins to lipids through glycan linkages.

N-Linked Carbohydrate Antigens or Epitopes Thereof

N-linked glycosylation, is the attachment of the sugar molecule oligosaccharide known as glycan to a nitrogen atom (the amide nitrogen of an asparagine (Asn) residue of a protein), in a process called N-glycosylation. This type of linkage is important for both the structure and function of some eukaryotic proteins. The N-linked glycosylation process occurs in eukaryotes and widely in archaea, but very rarely in bacteria. The nature of N-linked glycans attached to a glycoprotein is determined by the protein and the cell in which it is expressed.

All N-linked glycans are based on the common core pentasaccharide, $Man_3GlcNAc_2$. Further processing in the Golgi results in three main classes of N-linked glycan classes: 1) High-mannose, 2), and Hybrid 3) Complex. High-mannose glycans contain unsubstituted terminal mannose sugars. These glycans typically contain between five and nine mannose residues attached to the chitobiose (GlcNAc$_2$) core. Hybrid glycans are characterized as containing both unsubstituted terminal mannose residues (as are present in high-mannose glycans) and substituted mannose residues with an N-acetylglucosamine linkage (as are present in complex glycans). These GlcNAc sequences added to the N-linked glycan core in hybrid and complex N-glycans are called "antennae". A biantennary glycan comprises two GlcNAc branches linked to the core, whereas a triantennary glycan comprises with three GlcNAc branches. Complex N-linked glycans differ from the high-mannose and hybrid glycans by having added GlcNAc residues at both the α-3 and α-6 mannose sites. Unlike the high-mannose glycans, complex glycans do not contain mannose residues apart from the core structure. Additional monosaccharides may occur in repeating lactosamine (GlcNAc-β(1→4)Gal) units. Complex glycans exist in bi-, tri- and tetraantennary forms and make up the majority of cell surface and secreted N-glycans. Complex glycans commonly terminate with sialic acid residues. Additional modifications such as the addition of a bisecting GlcNAc at the mannosyl core and/or a fucosyl residue on the innermost GlcNAc are also possible.

O-Linked Glycosylation

O-linked glycosylation is the attachment of a sugar molecule to an oxygen atom in an amino acid residue in a protein. O-linked glycosylation is a form of glycosylation that occurs in the Golgi apparatus in eukaryotes. It also occurs in archaea and a number pathogenic bacteria including *Burkholderia cenocepacia, Neisseria gonorrhoeae* and *Acinetobacter baumannii*.

O—N-acetylgalactosamine (O-GalNAc)

O-linked glycosylation occurs at a later stage during protein processing, probably in the Golgi apparatus. This is the addition of N-acetyl-galactosamine to serine or threonine residues by the enzyme UDP-N-acetyl-D-galactosamine: polypeptide N-acetylgalactosaminyltransferase (EC number 2.4.1.41), followed by other carbohydrates (such as galactose and sialic acid). This process is important for certain types of proteins such as proteoglycans, which involves the addition of glycosaminoglycan chains to an initially unglycosylated "proteoglycan core protein." These additions are usually serine O-linked glycoproteins, which seem to have one of two main functions. One function involves secretion to form components of the extracellular matrix, adhering one cell to another by interactions between the large sugar complexes of proteoglycans. GlcNAc-β-Ser/Thr, which are found in nuclear and cytoskeletal proteins, were the first reported example of glycosylated proteins found in a location other than secretory channels.

O-Fucose

O-fucose is added between the second and third conserved cysteines of EGF-like repeats in the Notch protein, and other substrates by GDP-fucose protein O-fucosyltransferase 1, and to Thrombospondin repeats by GDP-fucose protein O-fucosyltransferase 2 (commonly referred to as POFUT2). In the case of EGF-like repeats, the O-fucose may be further elongated to a tetrasaccharide by sequential addition of N-acetylglucosamine (GlcNAc), galactose, and sialic acid, and for Thrombospondin repeats, may be elongated to a disaccharide by the addition of glucose. Both of these fucosyltransferases have been localized to the endoplasmic reticulum, which is unusual for glycosyltransferases, most of which function in the Golgi apparatus.

O-Glucose

O-glucose is added between the first and second conserved cysteines of EGF-like repeats in the Notch protein, and possibly other substrates by protein:O-glucosyltransferase. This enzyme is localized to the ER like the O-fucosyltransferases. The O-glucose modification appears to be necessary for proper folding of the EGF-like repeats of the Notch protein, and increases secretion of this receptor.

O-Mannose

During O-mannosylation, a mannose residue is transferred from mannose-p-dolichol to a serine/threonine residue in secretory pathway proteins. O-mannosylation is common to both prokaryotes and eukaryotes.

Sialic Acid

Sialic acid is a generic term for the N- or O-substituted derivatives of neuraminic acid, a monosaccharide with a nine-carbon backbone. It is also the name for the most common member of this group, N-acetylneuraminic acid (Neu5Ac or NANA). Sialic acids are found widely distributed in animal tissues and to a lesser extent in other organisms, ranging from fungi to yeasts and bacteria, mostly in glycoproteins and gangliosides (they occur at the end of sugar chains connected to the surfaces of cells and soluble proteins).

The sialic acid family includes 43 derivatives of the nine-carbon sugar neuraminic acid, but these acids rarely appear free in nature. Normally they can be found as components of oligosaccharide chains of mucins, glycoproteins and glycolipids occupying terminal, non-reducing positions of complex carbohydrates on both external and internal membrane areas where they are very exposed and develop important functions.

Exemplary sialic acid derivatives include:

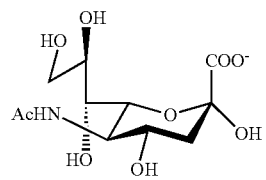

N-Acetylneuraminic acid
Neu5Ac

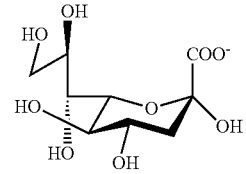

2-Keto-3-deoxynonic acid
Kdn

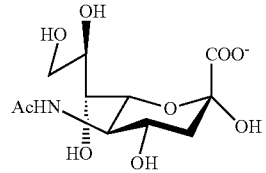

N-Acetylneuraminic acid
Neu5Ac

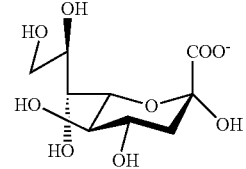

2-Keto-3-deoxynonic acid
Kdn

Sialic acids are found at all cell surfaces of vertebrates and some invertebrates, and also at certain bacteria that interact with vertebrates. Many viruses such as some adenoviruses (Adenoviridae), rotaviruses (Reoviridae) and influenza viruses (Orthomyxoviridae) can use host-sialylated structures for binding to their target host cell. Sialic acids provide a good target for these viruses since they are highly conserved and are abundant in large numbers in virtually all cells. Unsurprisingly, sialic acids also play an important role in several human viral infections. The influenza viruses have hemagglutinin (HA) glycoproteins on their surfaces that bind to sialic acids found on the surface of human erythrocytes and on the cell membranes of the upper respiratory tract.

In hemagglutination, viruses are mixed with blood cells, and the virus enters into cells of the upper respiratory tract. Widely used anti-influenza drugs (oseltamivir and zanamivir) are sialic acid analogs that interfere with release of newly generated viruses from infected cells by inhibiting the viral enzyme neuraminidase.

Some bacteria also use host-sialylated structures for binding and recognition. For example, free sialic acid can behave as a signal to some specific bacteria, like Pneumococcus, and can help the bacterium recognize that it has reached a vertebrate environment suitable for its colonization. Modifications of sialic acids, such as the N-glycolyl group at the 5 position or O-acetyl groups on the side chain, may reduce the action of bacterial sialidases.

pHLIP® Peptides

In the schematic, Carb-Linker-Peptide, Peptide is a pHLIP® peptide (a non-limiting example is pHLIP® comprising the Var3 sequence AXDDQNPWRAYLDLLFPTDTLLLDLLWA (SEQ ID NO: 3), or AXDQDNPWRAYLDLLFPTDTLLLDLLWA (SEQ ID NO: 4) or AX(Z)$_n$XPWRAYLDLLFPTDTLLLDLLWA (SEQ ID NO: 5), where "X" is a functional group for conjugation purposes, selected from lysine (Lys), cysteine (Cys), Azido-containing amino acid or other modified amino acids, and "Z" indicates any amino acid residue and n is any integer between (and including) 1-10 (e.g., 1≤n≤10).

For example, (Z)$_n$ could be QDNDQN (SEQ ID NO: 6) or any combination of polar residues, e.g., D, E, N or Q. The membrane non-inserting N-terminal flanking sequence of pHLIP® peptide can optionally be extended. For example, the N terminus of any of these sequences can be extended by the addition of amino acids to space the epitope away from the cell surface, e.g. by including a (glycine) extension. Non-limiting examples of such an extension include a peptide sequence with a poly-Gly motif.

An example of a wild type (WT) pHLIP® peptide is AEQNPIYWARYADWLFTTPLLLLDLALLVDADEGT (SEQ ID NO: 7) in which AEQNPIY (SEQ ID NO: 8) represents a flanking sequence, WARYADWLFTTPLLLLDLALLV (SEQ ID NO: 9) represents a membrane-inserting sequence, and DADEGT (SEQ ID NO: 10) represents a flanking sequence.

Other exemplary pHLIP® peptides are shown in the Tables below.

TABLE 1

Exemplary pHLIP® peptides

| Name | Sequence | SEQ ID No. |
| --- | --- | --- |
| Var3-1a | ACDQDNPWRAYLDLLFPTDTLLLDLLWA | SEQ. ID NO. 11 |
| Var3-1b | AKDQDNPWRAYLDLLFPTDTLLLDLLWA | SEQ. ID NO. 12 |
| Var3-2a | ACQDNDQNCPWRAYLDLLFPTDTLLLDLLWA | SEQ. ID NO. 13 |
| Var3-2b | AKQDNDQNKPWRAYLDLLFPTDTLLLDLLWA | SEQ. ID NO. 14 |
| WT-1 | GGEQNPIYWARYADWLFTTPLLLLDLALLVDADEGT | SEQ. ID NO. 15 |
| WT-2 | AEQNPIYWARYADWLFTTPLLLLDLALLVDADEGT | SEQ. ID NO. 16 |
| Var3-WT-Cys | ADDQNPWRAYLDLLFPTDTLLLDLLWDADECG | SEQ. ID NO. 17 |
| Cys-Var3-WT | ACDDQNPWRAYLDLLFPTDTLLLDLLWDADEG | SEQ. ID NO. 18 |
| Lys-Var3-WT | AKDDQNPWRAYLDLLFPTDTLLLDLLWDADEG | SEQ. ID NO. 19 |
| WT-Cys1 | AAEQNPIYWARYADWLFTTPLLLLDLALLVDADEGTCG | SEQ. ID NO. 20 |
| WT-Cys2 | Ac-AEQNPIYWARYADWLFTTPLLLLDLALLVDADEGCT | SEQ. ID NO. 21 |
| WT-Cys3 | GGEQNPIYWARYADWLFTTPLLLLDLALLVDADEGTCG | SEQ. ID NO. 22 |
| Cys-WT1 | Ac-ACEQNPIYWARYADWLFTTPLLLLDLALLVDADEGTG | SEQ. ID NO. 23 |
| Var0-NT | ACEQNPIYWARYADWLFTTPLLLLDLALLVDADEGT | SEQ. ID NO. 24 |
| Lys-WT1 | AKEQNPIYWARYADWLFTTPLLLLDLALLVDADEGT | SEQ. ID NO. 25 |
| Lys-WT2 | Ac-AKEQNPIYWARYADWLFTTPLLLLDLALLVDADEGTG | SEQ. ID NO. 26 |
| WT-KC | AAEQNPIYWARYADWLFTTPLLLLDLALLVDADEGTKCG | SEQ. ID NO. 27 |
| K-WT-C | AKEQNPIYWARYADWLFTTPLLLLDLALLVDADECT | SEQ. ID NO. 28 |
| N-pHLIP | ACEQNPIYWARYANWLFTTPLLLLNLALLVDADEGTG | SEQ. ID NO. 29 |
| N-pHLIP-b | ACEQNPIYWARYANWLFTTPLLLLNLALLVDADEGT | SEQ. ID NO. 30 |

TABLE 1-continued

Exemplary pHLIP® peptides

| Name | Sequence | SEQ ID No. |
|---|---|---|
| K-pHLIP | ACEQNPIYWARYAKWLFTTPLLLLKLALLVDADEGTG | SEQ. ID NO. 31 |
| NNQ | GGEQNPIYWARYADWLFTTPLLLLDLALLVNANQGT | SEQ. ID NO. 32 |
| D25A | AAEQNPIYWARYADWLFTTPLLLLALALLVDADEGT | SEQ. ID NO. 33 |
| D25A-KC | Ac-AAEQNPIYWARYADWLFTTPLLLLELALLVDADEGTKCG | SEQ. ID NO. 34 |
| D14A | AAEQNPIYWARYAAWLFTTPLLLLDLALLVDADEGT | SEQ. ID NO. 35 |
| P20A | AAEQNPIYWARYADWLFTTALLLLDLALLVDADEGT | SEQ. ID NO. 36 |
| D25E | AAEQNPIYWARYADWLFTTPLLLLELALLVDADEGT | SEQ. ID NO. 37 |
| D14E | AAEQNPIYWARYAEWLFTTPLLLLDLALLVDADEGT | SEQ. ID NO. 38 |
| 3D | AAEQNPIIYWARYADWLFTDLPLLLLDLLALLVDADEGT | SEQ. ID NO. 39 |
| R11Q | GEQNPIYWAQYADWLFTTPLLLLDLALLVDADEGTCG | SEQ. ID NO. 40 |
| D25Up | GGEQNPIYWARYADWLFTTPLLLDLLALLVDADEGTCG | SEQ. ID NO. 41 |
| D25Down | GGEQNPIYWARYADWLFTTPLLLLLDALLVDADEGTCG | SEQ. ID NO. 42 |
| D14Up | GGEQNPIYWARYDAWLFTTPLLLLDLALLVDADEGTCG | SEQ. ID NO. 43 |
| D14Down | GGEQNPIYWARYAWDLFTTPLLLLDLALLVDADEGTCG | SEQ. ID NO. 44 |
| P20G | AAEQNPIYWARYADWLFTTGLLLLDLALLVDADEGT | SEQ. ID NO. 45 |
| H1-Cys | DDDEDNPIYWARYADWLFTTPLLLLHGALLVDADECT | SEQ. ID NO. 46 |
| H1 | DDDEDNPIYWARYADWLFTTPLLLLHGALLVDADET | SEQ. ID NO: 47 |
| H2-Cys | DDDEDNPIYWARYAHWLFTTPLLLLHGALLVDADEGCT | SEQ. ID NO. 48 |
| Cys-H2 | CDDDEDNPIYWARYAHWLFTTPLLLLHGALLVDADET | SEQ ID NO: 49 |
| H2 | DDDEDNPIYWARYAHWLFTTPLLLLHGALLVDADEGT | SEQ. ID NO: 50 |
| H2N-Cys | DDDEDNPIYWARYAHWLFTTPLLLLHGALLVNADECT | SEQ. ID NO. 51 |
| H2N | DDDEDNPIYWARYAHWLFTTPLLLLHGALLVNADEGT | SEQ ID NO: 52 |
| H2N2-Cys | DDDEDNPIYWARYAHWLFTTPLLLLHGALLVNANECT | SEQ. ID NO. 53 |
| H2N2 | DDDEDNPIYWARYAHWLFTTPLLLLHGALLVNANEGT | SEQ ID NO: 54 |
| 1a-Trp | AEQNPIYWARYADFLFTTPLLLLDLALLVDADET | SEQ. ID NO. 55 |
| 1b-Trp | AEQNPIYFARYADWLFTTPLLLLDLALLVDADEGT | SEQ. ID NO. 56 |
| 1c-Trp | AEQNPIYFARYADFLFTTPLLLLDLALLWDADET | SEQ. ID NO. 57 |
| Fast-1 or Var1 | AKEDQNPYWARYADWLFTTPLLLLLDLALLVDG | SEQ. ID NO. 58 |
| Var1-2D1D | ACEDQNPYWARYADWLFTTPLLLLDLALLVDG | SEQ. ID NO. 59 |
| Fast1-Cys or Var1-2D1D-Cys | AEDQNPYWARYADWLFTTPLLLLDLALLVDCG | SEQ. ID NO. 60 |
| Fast1-E-Cys or Var1E | AEDQNPYWARYADWLFTTPLLLLELALLVECG | SEQ. ID NO. 61 |
| Fast1-E-Lys | AKEDQNDPYWARYADWLFTTPLLLLLDLALLVG | SEQ ID NO: 62 |
| Fast2 or Var2 | AKEDQNPYWRAYADLFTPLTLLDLLALWDG | SEQ. ID NO. 63 |
| Fast2-E-Cys or Var2E | AEDQNPYWARYADWLFTTPLLLLELALLVCG | SEQ ID NO: 64 |
| Var2-2D1D | ACEDQNPYWRAYADLFTPLTLLDLLALWDG | SEQ. ID NO. 65 |
| Var3-3D | ACDDQNPWRAYLDLLFPTDTLLLDLLW | SEQ. ID NO. 66 |
| Var3-3D-cys | AKDDQNPWRAYLDLLFPTDTLLLDLLWC | SEQ ID NO: 67 |

TABLE 1-continued

Exemplary pHLIP® peptides

| Name | Sequence | SEQ ID No. |
|---|---|---|
| Var4-3E | ACEEQNPWRAYLELLFPTETLLLELLW | SEQ. ID NO: 68 |
| Var5-3Da | ACDDQNPWARYLDWLFPTDTLLLDL | SEQ. ID NO: 69 |
| Var6-3Db | CDNNNPWRAYLDLLFPTDTLLLDW | SEQ. ID NO: 70 |
| Var8-3Eb | CEEQQPWAQYLELLFPTETLLLEW | SEQ. ID NO: 71 |
| Var9-3Ec | CEEQQPWRAYLELLFPTETLLLEW | SEQ. ID NO: 72 |
| Var15-2N | CDDDDDNPNYWARYANWLFTTPLLLLNGALLVEAEET | SEQ. ID NO: 73 |
| Var16-2P | CDDDDDNPNYWARYAPWLFTTPLLLLPGALLVEAEE | SEQ. ID NO: 74 |

TABLE 2

Exemplary pHLIP® peptides

| Name | Sequence | SEQ ID No. |
|---|---|---|
| Var14-Rev | Ac-TEDADVLLALDLLLLPTTFLWDAYRAWYPNQECA-Am | SEQ. ID NO. 75 |
| Sh | AEQNPIYWARYADWLFTTPL | SEQ. ID NO. 76 |
| Sh-Cys | AEQNPIYWARYADWLFTTPCL | SEQ. ID NO. 77 |
| Cys-Sh | ACEQNPIYWARYADWLFTTPL | SEQ. ID NO. 78 |
| Sh-1Trp | AEQNPIYFARYADWLFTTPL | SEQ. ID NO. 79 |
| Sh-W2 | AEQNPIYFARYADLLFPTTLAW | SEQ ID NO. 80 |
| Sh-W1 | AEQNPIYWARYADLLFPTTLAF | SEQ. ID NO. 81 |
| Sh-2W | AEQNPIYWARYADLLFPTTLAW | SEQ. ID NO. 82 |
| Sh-1D | KEDQNPWARYADLLFPTTLAW | SEQ. ID NO. 83 |
| Sh-1Db | KEDQNPWARYADLLFPTTLW | SEQ. ID NO. 84 |
| Var12-1D | ACEDQNPWARYADLLFPTTLAW | SEQ. ID NO. 85 |
| Var10-2D | ACEDQNPWARYADWLFPTTLLLD | SEQ. ID NO. 86 |
| Var13-1E | ACEEQNPWARYAELLFPTTLAW | SEQ. ID NO. 87 |
| Var11-2E | ACEEQNPWARYAEWLFPTTLLLLE | SEQ. ID NO. 88 |
| Var7-3E | ACEEQNPWARYLEWLFPTETLLLEL | SEQ. ID NO. 89 |
| Var7-3Eb | ACEEQNPQAEYAEWLFPTTLLLLE | SEQ. ID NO. 90 |

"Ac" means Acetylated N-terminus
"Am" means Amidated C-terminus

TABLE 3

Coded and exemplary non-coded amino acids including L-isomers, D-isomers, alpha-isomers, beta-isomers, glycol-, and methyl- modifications.

| No. | Abbrev | Name |
|---|---|---|
| 1 | Ala | Alanine |
| 2 | Arg | Arginine |
| 3 | Asn | Asparagine |
| 4 | Asp | Aspartic acid |
| 5 | Cys | Cysteine |
| 6 | Gln | Glutamine |
| 7 | Glu | Glutamic acid |
| 8 | Gly | Glycine |
| 9 | His | Histidine |
| 10 | Ile | Isoleucine |
| 11 | Leu | Leucine |
| 12 | Lys | Lysine |
| 13 | Met | Methionine |
| 14 | Phe | Phenylalanine |
| 15 | Pro | Proline |
| 16 | Ser | Serine |
| 17 | Thr | Threonine |
| 18 | Trp | Tryptophan |
| 19 | Tyr | Tyrosine |
| 20 | Val | Valine |
| 21 | Sec | Selenocysteine |
| 22 | Sem | Selenomethionine |
| 23 | Pyl | Pyrrolysine |
| 24 | Aad | Alpha-aminoadipic acid |
| 25 | Acpa | Amino-caprylic acid |
| 26 | Aecys | Aminoethyl cysteine |
| 27 | Afa | Aminophenyl acetate |
| 28 | Gaba | Gamma-aminobutyric acid |
| 29 | Aiba | Aminoisobutyric acid |
| 30 | Aile | Alloisoleucine |
| 31 | Alg | Allylglycine |
| 32 | Aba | Amino-butyric acid |
| 33 | Aphe | Amino-phenylalanine |
| 34 | Brphe | Bromo-phenylalanine |
| 35 | Cha | Cyclo-hexylalanine |
| 36 | Cit | Citrulline |
| 37 | Clala | Chloroalanine |
| 38 | Cie | Cycloleucine |
| 39 | Clphe | Fenclonine (or chlorophenylalanine) |
| 40 | Cya | Cysteic acid |
| 41 | Dab | Diaminobutyric acid |
| 42 | Dap | Diaminopropionic acid |
| 43 | Dap | Diaminopimelic acid |
| 44 | Dhp | Dehydro-proline |
| 45 | Dhphe | DOPA (or 3,4-dihydroxyphenylalanine) |
| 46 | Fphe | Fluorophenylalanine |
| 47 | Gaa | Glucosaminic acid |
| 48 | Gla | Gamma-carboxyglutamic acid |
| 49 | Hag | Homoarginine |
| 50 | Hlys | Hydroxylysine |
| 51 | Hnvl | Hydroxynorvaline |
| 52 | Hog | Homoglutamine |
| 53 | Hoph | Homophenylalanine |
| 54 | Has | Homoserine |
| 55 | Hse | Homocysteine |
| 56 | Hpr | Hydroxyproline |
| 57 | Iphe | Iodo-phenylalanine |
| 58 | Ise | Isoserine |

TABLE 3-continued

Coded and exemplary non-coded amino acids including L-isomers, D-isomers, alpha-isomers, beta-isomers, glycol-, and methyl- modifications.

| No. | Abbrev | Name |
|---|---|---|
| 59 | Mle | Methyl-leucine |
| 60 | Msmet | Methionine-methylsulfonium chloride |
| 61 | Nala | Naphthyl-alanine |
| 62 | Nle | Norleucine (or 2-aminohexanoic acid) |
| 63 | Nmala | N-methyl-alanine |
| 64 | Nva | Norvaline (or 2-aminopentanoic acid) |
| 65 | Obser | O-benzyl-serine |
| 66 | Obtyr | O-benzyl-tyrosine |
| 67 | Oetyr | O-ethyl-tyrosine |
| 68 | Omser | O-methyl-serine |
| 69 | Omthr | O-methy-threonine |
| 70 | Omtyr | O-methyl-tyrosine |
| 71 | Orn | Ornithine |
| 72 | Pen | Penicillamine |
| 73 | Pga | Pyroglutamic acid |
| 74 | Pip | Pipecolic acid |
| 75 | Sar | Sarcosine |
| 76 | Tfa | Trifluoro-alanine |
| 77 | Thphe | Hydroxy-Dopa |
| 78 | Vig | Vinylglycine |
| 79 | Aaspa | Amino-aminoethylsulfanylpropanoic acid |
| 80 | Ahdna | Amino-hydroxy-dioxanonanolic acid |
| 81 | Ahoha | Amino-hydroxy-oxahexanoic acid |
| 82 | Ahsopa | Amino-hydroxyethylsulfanylpropanoic acid |
| 83 | Tyr(Me) | Methoxyphenyl-methylpropanyl oxycarbonylamino propanoic acid |
| 84 | MTrp | Methyl-tryptophan |
| 85 | pTyr | Phosphorylated Tyr |
| 86 | pSer | Phosphorylated Ser |
| 87 | pThr | Phosphorylated Thr |
| 88 | BLys | BiotinLys |
| 89 | Hyp | Hydroproline |
| 90 | Phg | Phenylglycine |
| 91 | Cha | Cyclohexyl-alanine |
| 92 | Chg | Cyclohexylglycine |
| 93 | Nal | Naphthylalanine |
| 94 | Pal | Pyridyl-alanine |
| 95 | Pra | Propargylglycine |
| 96 | Gly(allyl) | Pentenoic acid |
| 97 | Pen | Penicillamine |
| 98 | MetO | Methionine sulfoxide |
| 99 | Pca | Pyroglutamic acid |
| 100 | Ac-Lys | Acetylation of Lys |

TABLE 5

Examples of coded amino acid substitutions

| Original Residue | Substitution |
|---|---|
| Ala (A) | Gly; Ile; Leu; Met; Phe; Pro; Trp; Tyr; Val |
| Arg (R) | Lys |
| Asn (N) | Gln; His |
| Asp (D) | Glu |
| Cys (C) | Ser; Met |
| Gln (Q) | Asn; His |
| Glu (E) | Asp |
| Gly (G) | Ala; Ile; Leu; Met; Phe; Pro; Trp; Tyr; Val |
| His (H) | Asn; Gln |
| Ile (I) | Ala; Gly; Leu; Met; Phe; Pro; Trp; Tyr; Val |
| Leu (L) | Ala; Gly; Ile; Met; Phe; Pro; Trp; Tyr; Val |
| Lys (K) | Arg |
| Met (M) | Ala; Gly; Leu; Ile; Phe; Pro; Trp; Tyr; Val |
| Phe (F) | Ala; Gly; Leu; Ile; Met; Pro; Trp; Tyr; Val |
| Pro (P) | Ala; Gly; Leu; Ile; Met; Phe; Trp; Tyr; Val |
| Ser (S) | Thr |
| Thr (T) | Ser |
| Trp (W) | Ala; Gly; Leu; Ile; Met; Pro; Phe; Tyr; Val |
| Tyr (Y) | Ala; Gly; Leu; Ile; Met; Pro; Phe; Trp; Val |
| Val (V) | Ala; Gly; Leu; Ile; Met; Pro; Phe; Trp; Tyr |

TABLE 4

Non-limiting examples of protonatable residues and their substitutions including L-isomers, D- isomers, alpha-isomers, and beta-isomers.

| Original Residue | Exemplary amino acids substitution |
|---|---|
| Asp (D) | Glu (E); Gla (Gla); Aad (Aad) |
| Glu (E) | Asp (D); Gla (Gla); Aad (Aad) |

TABLE 6

Non-limiting examples of membrane-inserting sequences belonging to different groups of pHLIP® peptides. Each protonatable residue (shown in bold) could be replaced by its substitution from Table 4. Each non-polar residue could be replaced by its coded amino acid substitution from Table 5, and/or non-coded amino acid substitutions from Table 3.

| Groups | Sequences | SEQ ID NO: |
|---|---|---|
| WT BRC | WARYADWLFTTPLLLLDLALL | 91 |
|  | YARYADWLFTTPLLLLDLALL | 92 |
|  | WARYSDWLFTTPLLLYDLGLL | 93 |
|  | WARYTDWFTTPLLLYDLALLA | 94 |
|  | WARYTDWLFTTPLLLYDLGLL | 95 |
|  | WARYADWLFTTPLLLLDLSLL | 96 |
| WT-BRC Reverse | LLALDLLLLPTTFLWDAYRAW | 97 |
|  | LLALDLLLLPTTFLWDAYRAY | 98 |
|  | LLGLDYLLLPTTFLWDSYRAW | 99 |
|  | ALLALDYLLLPTTFWDTYRAW | 100 |
|  | LLGLDYLLLPTTFLWDTYRAW | 101 |
|  | LLSLDLLLLPTTFLWDAYRAW | 102 |
| ATRAM | GLAGLLGLEGLLGLPLGLLEGLWLGL | 103 |
| ATRAM Reverse | LGLWLGELLGLPLGLLGELGLLGALG | 104 |
| Var3 | WRAYLDLLFPTDTLLLDLLW | 105 |
| Var3 Reverse | WLLDLLLTDTPFLLDLYARW | 106 |
| Var7 | WARYLEWLFPTETLLLEL | 107 |
|  | WAQYLELLFPTETLLLEW | 108 |
| Var7 Reverse | LELLLTETPFLWELYRAW | 109 |
|  | WELLLTETPFLLELYQAW | 110 |
| Single D/E | WLFTTPLLLLNGALLVE | 111 |
|  | WLFTTPLLLLPGALLVE | 112 |
|  | WARYADLLFPTTLAW | 113 |
| Single D/E Reverse | EVLLAGNLLLLPTTFLW | 114 |
|  | EVLLAGPLLLLPTTFLW | 115 |
|  | WALTTPFLLDAYRAW | 116 |
| pHLIP®-Rho | NLEGFFATLGGEIALWSLVVLAIE | 117 |
|  | EGFFATLGGEIALWSDVVLAIE | 118 |
|  | EGFFATLGGEIPLWSDVVLAIE | 119 |
| pHLIP®-Rho Reverse | EIALVVLSWLAIEGGLTAFFGELN | 120 |
|  | EIALVVDSWLAIEGGLTAFFGE | 121 |
|  | EIALVVDSWLPIEGGLTAFFGE | 122 |
| pHLIP®-CA9 | ILDLVFGLLFAVTSVDFLVQW | 123 |
| pHLIP®-CA9 Reverse | WQVLFDVSTVAFLLGFVLDLI | 124 |

TABLE 7

Non-limiting examples of pHLIP® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
| --- | --- | --- |
| SEQ ID NO: 125 | WT-2D | AEQNPIYWARYADWLFTTPLLLLDLALLVDADET |
| SEQ ID NO: 126 | WT-6E | AEQNPIYWARYAEWLFTTPLLLLELALLVEAEET |
| SEQ ID NO: 127 | WT-3D | ADDQNPWRAYLDLLFPDTTDLLLLDLLWDADET |
| SEQ ID NO: 128 | WT-9E | AEEQNPWRAYLELLFPETTELLLLELLWEAEET |
| SEQ ID NO: 129 | WT-GlaD | AEQNPIYWARYA*Gla*WLFTTPLLLLDLALLVDADET |
| SEQ ID NO: 130 | WT-DGla | AEQNPIYWARYADWLFTTPLLLL*Gla*LALLVDADET |
| SEQ ID NO: 131 | WT-2Gla | AEQNPIYWARYA*Gla*WLFTTPLLLL*Gla*LALLVDADET |
| SEQ ID NO: 132 | WT-AadD | AEQNPIYWARYA*Aad*WLFTTPLLLLDLALLVDADET |
| SEQ ID NO: 133 | WT-DAad | AEQNPIYWARYADWLFTTPLLLL*Aad*LALLVDADET |
| SEQ ID NO: 134 | WT-2Aad | AEQNPIYWARYA*Aad*WLFTTPLLLL*Aad*LALLVDADET |
| SEQ ID NO: 135 | WT-GlaAad | AEQNPIYWARYA*Gla*WLFTTPLLLL*Aad*LALLVDADET |
| SEQ ID NO: 136 | WT-AadGla | AEQNPIYWARYA*Aad*WLFTTPLLLL*Gla*LALLVDADET |
| SEQ ID NO: 137 | WT-1 | GGEQNPIYWARYADWLFTTPLLLLDLALLVDADEGT |
| SEQ ID NO: 138 | WT-2 | GGEQNPIYWARYADWLFTTPLLLLDLALLVDADEGT |
| SEQ ID NO: 139 | WT-3 | AAEQNPIYWARYADWLFTTPLLLLDLALLVDADEGT |
| SEQ ID NO: 140 | WT-4 | AEQNPIYWARYADWLFTTPLLLLDLALLVDADEGT |
| SEQ ID NO: 141 | WT-2N | AEQNPIYWARYANWLFTTPLLLLNLALLVDADEGT |
| SEQ ID NO: 142 | WT-2K | AEQNPIYWARYAKWLFTTPLLLLKLALLVDADEGT |
| SEQ ID NO: 143 | WT-2DNANQ | GGEQNPIYWARYADWLFTTPLLLLDLALLVNANQGT |
| SEQ ID NO: 144 | WT-D25A | AAEQNPIYWARYADWLFTTPLLLLALALLVDADEGT |
| SEQ ID NO: 145 | WT-D14A | AAEQNPIYWARYAAWLFTTPLLLLDLALLVDADEGT |
| SEQ ID NO: 146 | WT-P20A | AAEQNPIYWARYADWLFTTALLLLDLALLVDADEGT |
| SEQ ID NO: 147 | WT-D25E | AAEQNPIYWARYADWLFTTPLLLLELALLVDADEGT |
| SEQ ID NO: 148 | WT-D14E | AAEQNPIYWARYAEWLFTTPLLLLDLALLVDADEGT |
| SEQ ID NO: 149 | WT-3D-2 | AAEQNPIIYWARYADWLFTDLPLLLLDLLALLVDADEGT |
| SEQ ID NO: 150 | WT-R11Q | GEQNPIYWAQYADWLFTTPLLLLDLALLVDADEG |
| SEQ ID NO: 151 | WT-D25Up | GGEQNPIYWARYADWLFTTPLLLLDLLALLVDADEG |
| SEQ ID NO: 152 | WT-D25Down | GGEQNPIYWARYADWLFTTPLLLLLDLALLVDADEG |
| SEQ ID NO: 153 | WT-D14Up | GGEQNPIYWARYDAWLFTTPLLLLDLALLVDADEGT |
| SEQ ID NO: 154 | WT-D14Down | GGEQNPIYWARYAWDLFTTPLLLLDLALLVDADEG |
| SEQ ID NO: 155 | WT-P20G | AAEQNPIYWARYADWLFTTGLLLLDLALLVDADEGT |
| SEQ ID NO: 156 | WT-DH | DDDEDNPIYWARYADWLFTTPLLLLHGALLVDAD |
| SEQ ID NO: 476 | WT-2H | DDDEDNPIYWARYAHWLFTTPLLLLHGALLVDADE |
| SEQ ID NO: 157 | WT-L16H | CEQNPIYWARYADWHFTTPLLLLDLALLVDADE |
| SEQ ID NO: 158 | WT-1Wa | AEQNPIYWARYADFLFTTPLLLLDLALLVDADET |
| SEQ ID NO: 159 | WT-1Wb | AEQNPIYFARYADWLFTTPLLLLDLALLVDADE |
| SEQ ID NO: 160 | WT-1Wc | AEQNPIYFARYADFLFTTPLLLLDLALLWDADET |

TABLE 7-continued

Non-limiting examples of pHLIP® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
|---|---|---|
| SEQ ID NO: 161 | WT-W6 | ADNNPWIYARYADLTTFPLLLLDLALLVDFDD |
| SEQ ID NO: 162 | WT-W17 | ADNNPFIYARYADLTTWPLLLLDLALLVDFDD |
| SEQ ID NO: 163 | WT-W30 | ADNNPFIYARYADLTTFPLLLLDLALLVDWDD |
| SEQ ID NO: 164 | WT-W17-P7 | ADNNPFPYARYADLTTWILLLLDLALLVDFDD |
| SEQ ID NO: 165 | WT-W39-R11 | ADNNPFIYAYRADLTTFPLLLLDLALLVDWDD |
| SEQ ID NO: 166 | WT-W30-R15 | ADNNPFIYATYADLRTFPLLLLDLALLVDWDD |
| SEQ ID NO: 167 | WT-Rev | Ac-TEDADVLLALDLLLLPTTFLWDAYRAWYPNQEA-Am |
| SEQ ID NO: 168 | Var1-3D | AEDQNPYWARYADWLFTTPLLLLDLALLVD |
| SEQ ID NO: 169 | Var1-1D2E | AEDQNPYWARYADWLFTTPLLLLELALLVE |
| SEQ ID NO: 170 | Var2-3D | AEDQNPYWRAYADLFTPLTLLDLLALWD |
| SEQ ID NO: 171 | Var3-3D | ADDQNPWRAYLDLLFPTDTLLLLDLLW |
| SEQ ID NO: 172 | Var3-WT | ADDQNPWRAYLDLLFPTDTLLLLDLLWDADE |
| SEQ ID NO: 173 | Var3-Gla2D | ADDQNPWRAYL*Gla*LLFPTDTLLLLDLLW |
| SEQ ID NO: 174 | Var3-DGlaD | ADDQNPWRAYLDLLFPT*Gla*TLLLLDLLW |
| SEQ ID NO: 175 | Var3-2DGla | ADDQNPWRAYLDLLFPTDTLLL*Gla*LLW |
| SEQ ID NO: 176 | Var3-2GlaD | ADDQNPWRAYL*Gla*LLFPT*Gla*TLLLLDLLW |
| SEQ ID NO: 177 | Var3-GlaDGla | ADDQNPWRAYL*Gla*LLFPTDTLLL*Gla*LLW |
| SEQ ID NO: 178 | Var3-D2Gla | ADDQNPWRAYLDLLFPT*Gla*TLLL*Gla*LLW |
| SEQ ID NO: 179 | Var3-3Gla | ADDQNPWRAYL*Gla*LLFPT*Gla*TLLL*Gla*LLW |
| SEQ ID NO: 180 | Var3-Aad2D | ADDQNPWRAYL*Aad*LLFPTDTLLLLDLLW |
| SEQ ID NO: 181 | Var3-DAadD | ADDQNPWRAYLDLLFPT*Aad*TLLLLDLLW |
| SEQ ID NO: 182 | Var3-2DAad | ADDQNPWRAYLDLLFPTDTLLL*Aad*LLW |
| SEQ ID NO: 183 | Var3-2AadD | ADDQNPWRAYL*Aad*LLFPT*Aad*TLLLLDLLW |
| SEQ ID NO: 184 | Var3-AadDAad | ADDQNPWRAYL*Aad*LLFPTDTLLL*Aad*LLW |
| SEQ ID NO: 185 | Var3-D2Aad | ADDQNPWRAYLDLLFPT*Aad*TLLL*Aad*LLW |
| SEQ ID NO: 186 | Var3-3Aad | ADDQNPWRAYL*Aad*LLFPT*Aad*TLLL*Aad*LLW |
| SEQ ID NO: 187 | Var3-GlaAadD | ADDQNPWRAYL*Gla*LLFPT*Aad*TLLLLDLLW |
| SEQ ID NO: 188 | Var3-GlaDAad | ADDQNPWRAYL*Gla*LLFPTDTLLL*Aad*LLW |
| SEQ ID NO: 189 | Var3-2GlaAad | **ADDQNPWRAYL*Gla*LLFPT*Gla*TLLL*Aad*LLW** |
| SEQ ID NO: 190 | Var3-AadGlaD | **ADDQNPWRAYL*Aad*LLFPT*Gla*TLLLLDLLW** |
| SEQ ID NO: 191 | Var3-AadDGla | **ADDQNPWRAYL*Aad*LLFPTDTLLL*Gla*LLW** |
| SEQ ID NO: 192 | Var3-GlaAadGla | **ADDQNPWRAYL*Gla*LLFPT*Aad*TLLL*Gla*LLW** |
| SEQ ID NO: 193 | Var3-GLL | GEEQNPWLGAYLDLLFPLELLGLLELGLW |
| SEQ ID NO: 194 | Var3-M | ADDDDDDPWQAYLDLLFPTDTLLLLDLLW |
| SEQ ID NO: 195 | Var4-3E | AEEQNPWRAYLELLFPTETLLLLELLW |
| SEQ ID NO: 196 | Var5-3Da | ADDQNPWARYLDWLFPTDTLLLLDL |
| SEQ ID NO: 197 | Var6-3Db | DNNNPWRAYLDLLFPTDTLLLLDW |

TABLE 7-continued

Non-limiting examples of pHLIP® sequences. A cysteine, a lysine, an azido-modified amino acid, or an alkynyl modified amino acid can be incorporated at the N-terminal (first 6 residues) or C-terminal (last 6 residues) parts of the peptides for conjugation with a cargo, and a linker.

| SEQ ID NO | Name | Sequence |
|---|---|---|
| SEQ ID NO: 198 | Var7-3E | AEEQNPWARYLEWLFPTETLLLEL |
| SEQ ID NO: 199 | Var7-M | DDDDDDPWQAYLDLFPTDTLALDLW |
| SEQ ID NO: 200 | Var8-3E | EEQQPWAQYLELLFPTETLLLEW |
| SEQ ID NO: 201 | Var9-3E | EEQQPWRAYLELLFPTETLLLEW |
| SEQ ID NO: 202 | Var10-2D | AEDQNPWARYADWLFPTTLLLLD |
| SEQ ID NO: 203 | Var11-2E | AEEQNPWARYAEWLFPTTLLLLE |
| SEQ ID NO: 204 | Var12-1D | AEDQNPWARYADLLFPTTLAW |
| SEQ ID NO: 205 | Var13-1E | AEEQNPWARYAELLFPTTLAW |
| SEQ ID NO: 206 | Var15-2N | DDDDDNPNYWARYANWLFTTPLLLLNGALLVEAEET |
| SEQ ID NO: 207 | Var16-2P | DDDDDNPNYWARYAPWLFTTPLLLLPGALLVEAEET |
| SEQ ID NO: 208 | Var17 | AEQNPIYFARYADFLFTTPLLLLDLALLWDADET |
| SEQ ID NO: 209 | Var18 | AEQNPIYWARYADFLFTTPLLLLDLALLVDADET |
| SEQ ID NO: 210 | Var19a | AEQNPIYWARYADWLFTTPL |
| SEQ ID NO: 211 | Var20 | AEQNPIYFARYADLLFPTTLAW |
| SEQ ID NO: 212 | Var21 | AEQNPIYWARYADLLFPTTLAF |
| SEQ ID NO: 213 | Var22 | AEQNPIYWARYADLLFPTTLAW |
| SEQ ID NO: 214 | Var23 | AEQNPIYFARYADWLFTTPL |
| SEQ ID NO: 215 | Var24 | EDQNPWARYADLLFPTTLAW |
| SEQ ID NO: 216 | ATRAM | GLAGLAGLLGLEGLLGLPLGLLEGLWLGLELEGN |
| SEQ ID NO: 217 | pHLIP-CA9 | EQNPIYILDLVFGLLFAVTSVDFLVQWDDAGD |
| SEQ ID NO: 218 | pHLIP-Rho | NLEGFFATLGGEIALWSLVVLAIE |
| SEQ ID NO: 219 | pHLIP-RhoM1 | NNEGFFATLGGEIALWSDVVLAIE |
| SEQ ID NO: 220 | pHLIP-RhoM2 | DNNEGFFATLGGEIPLWSDVVLAIE |

Carbohydrate epitopes may also be delivered to the cell surface of target cells (tumor cells and other diseased tissues/cells) using cyclic pHLIP® peptides. A cyclic peptide is one that comprises a circle geometry or structure. For example, the entire structure of the peptide is circular or a portion of the structure is circular. For example, in the latter case the peptide comprises a cyclic portion and a linear (or tail) portion. In various embodiments, a pH triggered peptide comprises at least 4 amino acids, where (a) at least 2 of the at least 4 amino acids of the peptide are non-polar amino acids, (b) at least 1 of the at least 4 amino acids of the peptide is a protonatable amino acid, and (c) the peptide has a higher affinity to a membrane lipid bilayer at pH 5.0 compared to at pH 8.0. Such pHLIP® peptides are described in International Patent Application No. PCT/US2017/023458 (PCT publication no. WO2017/165452A1, hereby incorporated by reference.

Exemplary cyclic pHLIP® peptides are described and shown below. A lowercase "c" at the beginning of a sequence herein denotes a cyclic peptide (e.g., as in c[(WE)$_3$WC]) (Peptide 1), and a lowercase "l" denotes a linear peptide (e.g., as in l(CW(EW)$_4$)) (Peptide 188). In the case of cyclic structures that comprise a tail, the cyclic portion of the compound is within brackets, and the tail portion follows (is to the right of) the brackets. For example, in the compound c[E$_5$K]W$_5$C, c[E$_5$K] is the cyclic peptide portion, and W$_5$C (SEQ ID NO: 477) is the peptide tail portion. As another example, in c[E$_5$K]W$_4$C, the cyclic peptide portion is c[E$_5$K] and the peptide tail portion is W$_4$C (SEQ ID NO: 478).

With respect to cyclic peptides, the amino acids within brackets may be present in the order listed in brackets from left to right, or in any order. For example, a cyclic peptide c[X$_2$Y$_2$] may have the corresponding linear sequence: XXYY, XYXY, YXXY, XYYX, or YXYX. In some cases, multiple examples of corresponding linear sequences for an exemplary cyclic peptide are listed in Table 3.

TABLE 8 provides a summary of peptide sequences

| Peptide | Sequence | Linear Sequence | SEQ ID NO |
|---|---|---|---|
| 1 | c[(WE)$_3$WC] | WEWEWEWC | 221 |
| 2 | c[(WE)$_4$WC] | WEWEWEWEWC | 222 |

TABLE 8-continued provides a summary of peptide sequences

| Peptide | Sequence | Linear Sequence | SEQ ID NO |
|---|---|---|---|
| 3 | c[(WE)$_5$WC] | WEWEWEWEWEWC | 223 |
| 4 | c[(LE)$_4$WC] | LELELELEWC | 224 |
| 5 | c[E$_4$W$_5$C] | EEEEWWWWWC | 225 |
| 6 | l(CW(EW)$_4$) | CWEWEWEWEW | 226 |
| 7 | c[R$_4$W$_5$C] | RRRRWWWWWC | 227 |

TABLE 9 provides additional non-limiting examples of peptide sequences.

| Cyclic Peptide | Circular Sequence | Linear Sequence | SEQ ID NO |
|---|---|---|---|
| 1 | c[E$_3$W$_5$C] | EEEWWWWWC | 228 |
| 2 | c[E$_3$W$_5$C] | EWEWWWWEC | 229 |
| 3 | c[E$_3$W$_5$C] | EWWEWWWEC | 230 |
| 4 | c[E$_3$W$_5$C] | EWWWEWWEC | 231 |
| 5 | c[E$_3$W$_5$C] | EWWWWEWEC | 232 |
| 6 | c[E$_3$W$_5$C] | EWWWWWEEC | 233 |
| 7 | c[E$_3$W$_5$C] | EWEEWWWWC | 234 |
| 8 | c[E$_3$W$_5$C] | EWWEEWWWC | 235 |
| 9 | c[E$_3$W$_5$C] | EWWWEEWWC | 236 |
| 10 | c[E$_3$W$_5$C] | EWWWWEEWC | 237 |
| 11 | c[E$_3$W$_5$C] | WEEEWWWWC | 238 |
| 12 | c[E$_3$W$_5$C] | WWEEEWWWC | 239 |
| 13 | c[E$_3$W$_5$C] | WWWEEEWWC | 240 |
| 14 | c[E$_3$W$_5$C] | WWWWEEEWC | 241 |
| 15 | c[E$_3$W$_5$C] | WEWEEWWWC | 242 |
| 16 | c[E$_3$W$_5$C] | WEWWEEWWC | 243 |
| 17 | c[E$_3$W$_5$C] | WEWWWEEWC | 244 |
| 18 | c[E$_3$W$_5$C] | WEWWWWEEC | 245 |
| 19 | c[E$_3$W$_5$] | EEEWWWWW | 246 |
| 20 | c[E$_3$W$_5$] | EWEWWWWE | 247 |
| 21 | c[E$_3$W$_5$] | EWWEWWWE | 248 |
| 22 | c[E$_3$W$_5$] | EWWWEWWE | 249 |
| 23 | c[E$_3$W$_5$] | EWWWWEWE | 250 |
| 24 | c[E$_3$W$_5$] | EWWWWWEE | 251 |
| 25 | c[E$_3$W$_5$] | EWEEWWWW | 252 |
| 26 | c[E$_3$W$_5$] | EWWEEWWW | 253 |
| 27 | c[E$_3$W$_5$] | EWWWEEWW | 254 |
| 28 | c[E$_3$W$_5$] | EWWWWEEW | 255 |
| 29 | c[E$_3$W$_5$] | WEEEWWWW | 256 |
| 30 | c[E$_3$W$_5$] | WWEEEWWW | 257 |
| 31 | c[E$_3$W$_5$] | WWWEEEWW | 258 |

TABLE 9-continued provides additional non-limiting examples of peptide sequences.

| Cyclic Peptide | Circular Sequence | Linear Sequence | SEQ ID NO |
|---|---|---|---|
| 32 | c[$E_3W_5$] | WWWWEEEW | 259 |
| 33 | c[$E_3W_5$] | WEWEEWWW | 260 |
| 34 | c[$E_3W_5$] | WEWWEEWW | 261 |
| 35 | c[$E_3W_5$] | WEWWWEEW | 262 |
| 36 | c[$E_3W_5$] | WEWWWWEE | 263 |
| 37 | c[$D_3W_5C$] | DDDWWWWWC | 264 |
| 38 | c[$D_3W_5C$] | DWDWWWWDC | 265 |
| 39 | c[$D_3W_5C$] | DWWDWWWDC | 266 |
| 40 | c[$D_3W_5C$] | DWWWDWWDC | 267 |
| 41 | c[$D_3W_5C$] | DWWWWDWDC | 268 |
| 42 | c[$D_3W_5C$] | DWWWWWDDC | 269 |
| 43 | c[$D_3W_5C$] | DWDDWWWWC | 270 |
| 44 | c[$D_3W_5C$] | DWWDDWWWC | 271 |
| 45 | c[$D_3W_5C$] | DWWWDDWWC | 272 |
| 46 | c[$D_3W_5C$] | DWWWWDDWC | 273 |
| 47 | c[$D_3W_5C$] | WDDDWWWWC | 274 |
| 48 | c[$D_3W_5C$] | WWDDDWWWC | 275 |
| 49 | c[$D_3W_5C$] | WWWDDDWWC | 276 |
| 50 | c[$D_3W_5C$] | WWWWDDDWC | 277 |
| 51 | c[$D_3W_5C$] | WDWDDWWWC | 278 |
| 52 | c[$D_3W_5C$] | WDWWDDWWC | 279 |
| 53 | c[$D_3W_5C$] | WDWWWDDWC | 280 |
| 54 | c[$D_3W_5C$] | WDWWWWDDC | 281 |
| 55 | c[$D_3W_5$] | DDDWWWWW | 282 |
| 56 | c[$D_3W_5$] | DWDWWWWD | 283 |
| 57 | c[$D_3W_5$] | DWWDWWWD | 284 |
| 58 | c[$D_3W_5$] | DWWWDWWD | 285 |
| 59 | c[$D_3W_5$] | DWWWWDWD | 286 |
| 60 | c[$D_3W_5$] | DWWWWWDD | 287 |
| 61 | c[$D_3W_5$] | DWDDWWWW | 288 |
| 62 | c[$D_3W_5$] | DWWDDWWW | 289 |
| 63 | c[$D_3W_5$] | DWWWDDWW | 290 |
| 64 | c[$D_3W_5$] | DWWWWDDW | 291 |
| 65 | c[$D_3W_5$] | WDDDWWWW | 292 |
| 66 | c[$D_3W_5$] | WWDDDWWW | 293 |
| 67 | c[$D_3W_5$] | WWWDDDWW | 294 |
| 68 | c[$D_3W_5$] | WWWWDDDW | 295 |
| 69 | c[$D_3W_5$] | WDWDDWWW | 296 |

TABLE 9-continued provides additional non-limiting examples of peptide sequences.

| Cyclic Peptide | Circular Sequence | Linear Sequence | SEQ ID NO |
|---|---|---|---|
| 70 | c[$D_3W_5$] | WDWWDDWW | 297 |
| 71 | c[$D_3W_5$] | WDWWWDDW | 298 |
| 72 | c[$D_3W_5$] | WDWWWWDD | 299 |
| 73 | c[$Gla_3W_5$] | GlaGlaGlaWWWWW | 300 |
| 74 | c[$Gla_3W_5$] | GlaWGlaWWWWGla | 301 |
| 75 | c[$Gla_3W_5$] | GlaWWGlaWWWGla | 302 |
| 76 | c[$Gla_3W_5$] | GlaWWWGlaWWGla | 303 |
| 77 | c[$Gla_3W_5$] | GlaWWWWGlaWGla | 304 |
| 78 | c[$Gla_3W_5$] | GlaWWWWWGlaGla | 305 |
| 79 | c[$Gla_3W_5$] | GlaWGlaGlaWWWW | 306 |
| 80 | c[$Gla_3W_5$] | GlaWWGlaGlaWWW | 307 |
| 81 | c[$Gla_3W_5$] | GlaWWWGlaGlaWW | 308 |
| 82 | c[$Gla_3W_5$] | GlaWWWWGlaGlaW | 309 |
| 83 | c[$Gla_3W_5$] | WGlaGlaGlaWWWW | 310 |
| 84 | c[$Gla_3W_5$] | WWGlaGlaGlaWWW | 311 |
| 85 | c[$Gla_3W_5$] | WWWGlaGlaGlaWW | 312 |
| 86 | c[$Gla_3W_5$] | WWWWGlaGlaGlaW | 313 |
| 87 | c[$Gla_3W_5$] | WGlaWGlaGlaWWW | 314 |
| 88 | c[$Gla_3W_5$] | WGlaWWGlaGlaWW | 315 |
| 89 | c[$Gla_3W_5$] | WGlaWWWGlaGlaW | 316 |
| 90 | c[$Gla_3W_5$] | WGlaWWWWGlaGla | 317 |
| 91 | c[$E_3W_4C$] | EEEWWWWC | 318 |
| 92 | c[$E_3W_4C$] | EWEWWWEC | 319 |
| 93 | c[$E_3W_4C$] | EWWEWWEC | 320 |
| 94 | c[$E_3W_4C$] | EWWWEWEC | 321 |
| 95 | c[$E_3W_4C$] | EWWWWEEC | 322 |
| 96 | c[$E_3W_4C$] | EWEEWWWC | 323 |
| 97 | c[$E_3W_4C$] | EWWEEWWC | 324 |
| 98 | c[$E_3W_4C$] | EWWWEEWC | 325 |
| 99 | c[$E_3W_4C$] | EWWWWEEC | 326 |
| 100 | c[$E_3W_4C$] | WEEEWWWC | 327 |
| 101 | c[$E_3W_4C$] | WWEEEWWC | 328 |
| 102 | c[$E_3W_4C$] | WWWEEEWC | 329 |
| 103 | c[$E_3W_4C$] | WWWWEEEC | 330 |
| 104 | c[$E_3W_4C$] | WEWEEWWC | 331 |
| 105 | c[$E_3W_4C$] | WEWWEEWC | 332 |
| 106 | c[$E_3W_4C$] | WEWWWEEC | 333 |
| 107 | c[$E_3W_4$] | EEEWWWW | 334 |

TABLE 9-continued provides additional non-limiting examples of peptide sequences.

| Cyclic Peptide | Circular Sequence | Linear Sequence | SEQ ID NO |
|---|---|---|---|
| 108 | c[$E_3W_4$] | EWEWWWE | 335 |
| 119 | c[$E_3W_4$] | EWWEWWE | 336 |
| 110 | c[$E_3W_4$] | EWWWEWE | 337 |
| 111 | c[$E_3W_4$] | EWWWWEE | 338 |
| 112 | c[$E_3W_4$] | EWEEWWW | 339 |
| 113 | c[$E_3W_4$] | EWWEEWW | 340 |
| 114 | c[$E_3W_4$] | EWWWEEW | 341 |
| 115 | c[$E_3W_4$] | EWWWWEE | 342 |
| 116 | c[$E_3W_4$] | WEEEWWW | 343 |
| 117 | c[$E_3W_4$] | WWEEEWW | 344 |
| 118 | c[$E_3W_4$] | WWWEEEW | 345 |
| 119 | c[$E_3W_4$] | WWWWEEE | 346 |
| 120 | c[$E_3W_4$] | WEWEEWW | 347 |
| 121 | c[$E_3W_4$] | WEWWEEW | 348 |
| 122 | c[$E_3W_4$] | WEWWWEE | 349 |
| 123 | c[$D_3W_4C$] | DDDWWWWC | 350 |
| 124 | c[$D_3W_4C$] | DWDWWWDC | 351 |
| 125 | c[$D_3W_4C$] | DWWDWWDC | 352 |
| 126 | c[$D_3W_4C$] | DWWWDWDC | 353 |
| 127 | c[$D_3W_4C$] | DWWWWDDC | 354 |
| 128 | c[$D_3W_4C$] | DWDDWWWC | 355 |
| 129 | c[$D_3W_4C$] | DWWDDWWC | 356 |
| 130 | c[$D_3W_4C$] | DWWWDDWC | 357 |
| 131 | c[$D_3W_4C$] | DWWWWDDC | 358 |
| 132 | c[$D_3W_4C$] | WDDDWWWC | 359 |
| 133 | c[$D_3W_4C$] | WWDDDWWC | 360 |
| 134 | c[$D_3W_4C$] | WWWDDDWC | 361 |
| 135 | c[$D_3W_4C$] | WWWWDDDC | 362 |
| 136 | c[$D_3W_4C$] | WDWDDWWC | 363 |
| 137 | c[$D_3W_4C$] | WDWWDDWC | 364 |
| 138 | c[$D_3W_4C$] | WDWWWDDC | 365 |
| 139 | c[$D_3W_4$] | DDDWWWW | 366 |
| 140 | c[$D_3W_4$] | DWDWWWD | 367 |
| 141 | c[$D_3W_4$] | DWWDWWD | 368 |
| 142 | c[$D_3W_4$] | DWWWDWD | 369 |
| 143 | c[$D_3W_4$] | DWWWWDD | 370 |
| 144 | c[$D_3W_4$] | DWDDWWW | 371 |
| 145 | c[$D_3W_4$] | DWWDDWW | 372 |

TABLE 9-continued provides additional non-limiting examples of peptide sequences.

| Cyclic Peptide | Circular Sequence | Linear Sequence | SEQ ID NO |
|---|---|---|---|
| 146 | c[$D_3W_4$] | DWWWDDW | 373 |
| 147 | c[$D_3W_4$] | DWWWWDD | 374 |
| 148 | c[$D_3W_4$] | WDDDWWW | 375 |
| 149 | c[$D_3W_4$] | WWDDDWW | 376 |
| 150 | c[$D_3W_4$] | WWWDDDW | 377 |
| 151 | c[$D_3W_4$] | WWWWDDD | 378 |
| 152 | c[$D_3W_4$] | WDWDDWW | 379 |
| 153 | c[$D_3W_4$] | WDWDDW | 380 |
| 154 | c[$D_3W_4$] | WDWWWDD | 381 |
| 155 | c[$Gla_3W_4$] | GlaGlaGlaWWWW | 382 |
| 156 | c[$Gla_3W_4$] | GlaWGlaWWWGla | 383 |
| 157 | c[$Gla_3W_4$] | GlaWWGlaWWGla | 384 |
| 158 | c[$Gla_3W_4$] | GlaWWWGlaWGla | 385 |
| 159 | c[$Gla_3W_4$] | GlaWWWWGlaGla | 386 |
| 160 | c[$Gla_3W_4$] | GlaWGlaGlaWWW | 387 |
| 161 | c[$Gla_3W_4$] | GlaWWGlaGlaWW | 388 |
| 162 | c[$Gla_3W_4$] | GlaWWWGlaGlaW | 389 |
| 163 | c[$Gla_3W_4$] | GlaWWWWGlaGla | 390 |
| 164 | c[$Gla_3W_4$] | WGlaGlaGlaWWW | 391 |
| 165 | c[$Gla_3W_4$] | WWGlaGlaGlaWW | 392 |
| 166 | c[$Gla_3W_4$] | WWWGlaGlaGlaW | 393 |
| 167 | c[$Gla_3W_4$] | WWWWGlaGlaGla | 394 |
| 168 | c[$Gla_3W_4$] | WGlaWGlaGlaWW | 395 |
| 169 | c[$Gla_3W_4$] | WGlaWWGlaGlaW | 396 |
| 170 | c[$Gla_3W_4$] | WGlaWWWGlaGla | 397 |
| 171 | c[(WE)$_3$WC] | WEWEWEWC | 398 |
| 172 | c[(EW)$_3$WC] | EWEWEWWC | 399 |
| 173 | c[(WD)$_3$WC] | WDWDWDWC | 400 |
| 174 | c[(DW)$_3$WC] | DWDWDWWC | 401 |
| 175 | c[(WGla)$_3$WC] | WGlaWGlaWDWC | 402 |
| 176 | c[(GlaW)$_3$WC] | DWDWDWDC | 403 |
| 177 | c[(WE)$_4$] | WEWEWEWE | 404 |
| 178 | c[(EW)$_4$] | EWEWEWEW | 405 |
| 179 | c[(WD)$_4$] | WDWDWDWD | 406 |
| 180 | c[(DW)$_4$] | DWDWDWDW | 407 |
| 181 | c[(WGla)$_4$] | WGlaWGlaWGlaWGla | 408 |
| 182 | c[(GlaW)$_4$] | GlaWGlaWGlaWGlaW | 409 |
| 183 | c[CW(EW)$_4$] | CWEWEWEWEW | 410 |

TABLE 9-continued provides additional non-limiting examples of peptide sequences.

| Cyclic Peptide | Circular Sequence | Linear Sequence | SEQ ID NO |
|---|---|---|---|
| 184 | c[(WGla)$_2$WDWC] | WGlaWGlaWDWC | 411 |
| 185 | c[(EW)$_3$EC] | EWEWEWEC | 412 |
| 186 | c[(DW)$_3$DC] | DWDWDWDC | 413 |
| 187 | c[E$_5$K]W$_5$C | Cyclic: EEEEEK<br>Tail: WWWWWC | 414 (cyclic portion),<br>415 (Tail) |
| 188 | c[E$_4$K]W$_5$C | Cyclic: EEEEK<br>Tail: WWWWWC | 416 (cyclic portion),<br>417 (Tail) |
| 189 | c[E$_5$K]W$_4$C | Cyclic: EEEEEK<br>Tail: WWWWC | 418 (cyclic portion),<br>419 (Tail) |
| 190 | c[E$_4$K]W$_4$C | Cyclic: EEEEK<br>Tail: WWWWC | 420 (cyclic portion),<br>421 (Tail) |
| 191 | c[E$_5$K]W$_5$ | Cyclic: EEEEEK<br>Tail: WWWWW | 422 (cyclic portion),<br>423 (Tail) |
| 192 | c[E$_4$K]W$_5$ | Cyclic: EEEEK<br>Tail: WWWWW | 424 (cyclic portion),<br>425 (Tail) |
| 193 | c[E$_5$K]W$_4$ | Cyclic: EEEEEK<br>Tail: WWWW | 426 (cyclic portion),<br>427 (Tail) |
| 194 | c[E$_4$K]W$_4$ | Cyclic: EEEEK<br>Tail: WWWW | 428 (cyclic portion),<br>429 (Tail) |
| 195 | c[D$_5$K]W$_5$C | Cyclic: DDDDDK<br>Tail: WWWWWC | 430 (cyclic portion),<br>431 (Tail) |
| 196 | c[D$_4$K]W$_5$C | Cyclic: DDDDK<br>Tail: WWWWWC | 432 (cyclic portion),<br>433 (Tail) |
| 197 | c[D$_5$K]W$_4$C | Cyclic: DDDDDK<br>Tail: WWWWC | 434 (cyclic portion),<br>435 (Tail) |
| 198 | c[D$_4$K]W$_4$C | Cyclic: DDDDK<br>Tail: WWWWC | 436 (cyclic portion),<br>437 (Tail) |
| 199 | c[D$_5$K]W$_5$ | Cyclic: DDDDDK<br>Tail: WWWWW | 438 (cyclic portion),<br>439 (Tail) |
| 200 | cW$_5$ | Cyclic: DDDDK<br>Tail: WWWWW | 440 (cyclic portion),<br>441 (Tail) |
| 201 | cW$_4$ | Cyclic: DDDDDK<br>Tail: WWWW | 442 (cyclic portion),<br>443 (Tail) |
| 202 | c[D$_4$K]W$_4$ | Cyclic: DDDDK<br>Tail: WWWW | 444 (cyclic portion),<br>445 (Tail) |
| 203 | c[Gla$_5$K]W$_5$C | Cyclic: GlaGlaGlaGlaGlaK<br>Tail: WWWWWC | 446 (cyclic portion),<br>447 (Tail) |
| 204 | c[Gla$_4$K]W$_5$C | Cyclic: GlaGlaGlaGlaK<br>Tail: WWWWWC | 448 (cyclic portion),<br>449 (Tail) |
| 205 | c[Gla$_5$K]W$_4$C | Cyclic: GlaGlaGlaGlaGlaK<br>Tail: WWWWC | 450 (cyclic portion),<br>451 (Tail) |
| 206 | c[Gla$_4$K]W$_4$C | Cyclic: GlaGlaGlaGlaK<br>Tail: WWWWC | 452 (cyclic portion),<br>453 (Tail) |
| 207 | c[Gla$_5$K]W$_5$ | Cyclic: GlaGlaGlaGlaGlaK<br>Tail: WWWWW | 454 (cyclic portion),<br>455 (Tail) |
| 208 | c[Gla$_4$K]W$_5$ | Cyclic: GlaGlaGlaGlaK<br>Tail: WWWWW | 456 (cyclic portion),<br>457 (Tail) |
| 209 | c[Gla$_5$K]W$_4$ | Cyclic: GlaGlaGlaGlaGlaK<br>Tail: WWWW | 458 (cyclic portion),<br>459 (Tail) |

TABLE 9-continued provides additional non-limiting examples of peptide sequences.

| Cyclic Peptide | Circular Sequence | Linear Sequence | SEQ ID NO |
|---|---|---|---|
| 210 | c[Gla$_4$K]W$_4$ | Cyclic: GlaGlaGlaGlaK<br>Tail: WWWW | 460 (cyclic portion),<br>461 (Tail) |
| 211 | c[E$_5$W$_5$C] | EEEEEWWWWWC | 462 |
| 212 | c[E$_4$W$_4$C] | EEEEWWWWC | 463 |
| 213 | c[(WE)$_4$CW] | WEWEWEWECW | 464 |
| 214 | c[(WR)$_4$WC] | WRWRWRWRWC | 465 |

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1 pHLIP® Peptide pHLIP® peptides are described here and in U.S. Pat. Nos. 9,814,781 and 9,289,508 (hereby incorporated by reference in their entireties) as well as U.S. Patent Publication 20180117183, 20180064648, 20180221500, 20180117183, 20180064648, 20160256560, 20150191508, 20150051153, and 20120142042, 20120039990, and 20080233107, each of which is hereby incorporated by reference in their entireties.

Linker

A linker could be relatively small, e.g., only a few atoms, to a rather large polar (or moderately hydrophobic) polymer or an N-terminal lengthening of the pHLIP® peptide by the addition of amino acids, e.g., glycine residues (poly-Gly). In some examples, a linker can be part of membrane non-inserting pHLIP® peptide sequence, such as those with a poly-Gly motif. In some examples, a linker could be PEG polymer. The purpose of a polymer or pHLIP® extension is to position epitopes at the surfaces of cells to enhance the access of antibodies or proteins for binding to the epitope. The size and hydrophobicity of the linker should ensure renal clearance of the construct and should not promote hepatic clearance. For example, a linker comprises a covalent bond or a chemical linker. Non-limiting example of linker is a PEG polymer in size ranging from 200 Da up to 20 kDa.

In some examples the following linkers and their derivatives could be used N-α-maleimidoacet-oxysuccinimide ester (AMAS); N-γ-maleimidobutyryl-oxysuccinimide ester (GMBS); N-β-maleimidopropyl-oxysuccinimide ester (BMPS); N-ε-malemidocaproyl-oxysuccinimide ester (EMCS); m-maleimidobenzoyl-n-hydroxysuccinimide ester (MBS); succinimidyl 3-(bromoacetamido)propionate (SBAP); succinimidyl (4-iodoacetyl)aminobenzoate (SIAB); N-ε-maleimidocaproic acid (EMCA); succinimidyl 4-(n-maleimidomethyl)cyclohexane-1-carboxy-(6-amido-caproate) (LC-SMCC); succinimidyl iodoacetate (SIA); succinimidyl (4-iodoacetyl)aminobenzoate (SIAB); succinimidyl 4-(p-maleimidophenyl)butyrate (SMPB); succinimidyl 6-((beta-maleimidopropionamido)hexanoate) (SMPH); 3-propargyloxypropanoic acid, succinimidyl ester (alkyne, succinimidyl ester); 1,4-bismaleimidobutane (BMB); bis-maleimidohexane (BMH); bismaleimidoethane (BMOE); tris(2-maleimidoethyl)amine (TMEA); N-β-maleimidopropionic acid hydrazide; (BMPH); N-ε-maleimidocaproic acid hydrazide (EMCH); N-κ-maleimidoundecanoic acid hydrazide (KMUH); 4-(4-n-maleimidophenyl)butyric acid hydrazide (MBPH); or p-maleimidophenyl isocyanate (PMPI).

Carbohydrate Epitope

As shown in FIGS. 5A and 5B, a carbohydrate epitope (or a plurality of epitopes) is conjugated to the membrane non-inserting part of the pHLIP® peptide (e.g., via a linker as described herein), to induce immune response by attracting of endogenous antibodies. The carbohydrate epitope is therefore situated distal from the surface of the cell. Non-limiting examples of carbohydrate epitopes are the following:

Alpha Gal Epitope (αGal)

In all mammals except man, apes and old world monkeys, specific carbohydrate linkages are present, such as Galactose-α-1,3-Galactose (αGal):

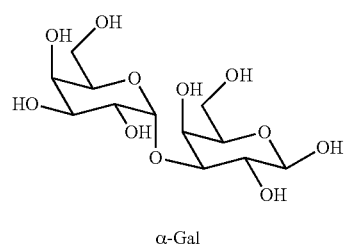 [SMILES: OCC1OC(OC2C(O)C(O)OC(CO)C2O)C(O)C(O)C1O]

α-Gal

In humans, the Gal-(alpha)-1,3-Gal link is recognized as foreign and a significant immune response against it is developed. αGal and its derivatives could be linked to pHLIP® to induce immune response predominantly within diseased tissues.

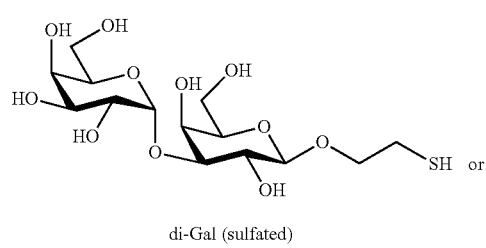

di-Gal (sulfated)

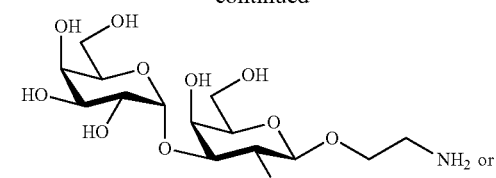

or diGal (aminated)

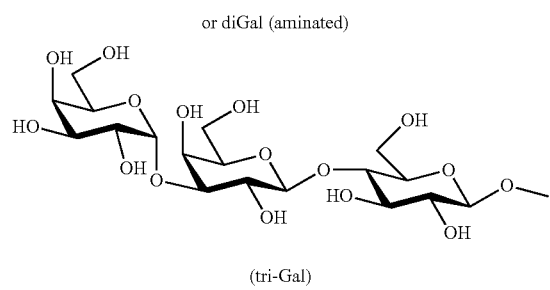

(tri-Gal)

Other carbohydrates include Gal-α-1,4-Gal; Gal-α-1,6-Gal; Gal-α-1,3-Glc; Fuc-α-1,2-Gal; Gal-β-1,2-Gal and their derivatives.

α-Rhamnose and its Derivatives Thereof

Shown below is an example of an unusual sugar occurring in L-form, α-rhamnose and its derivatives, which induces a significant immune response: Naturally occurring L-rhamnose does not appear in the body, and an antibody against it is available, as in case of Gal.

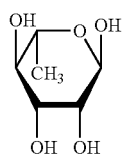

Blood Group Antigens and Derivatives Thereof

Blood group antigens and their derivatives are used for the compositions and methods described herein. An O (or H) antigen includes Fucose-Galactose-N-acetylglucosamine-Galactose-Glucose or its epitope is Fucα(1-2)Gal; an A antigen includes N-acetylgalactosamine (GalNAc) glycosidically bonded to the O antigen or its epitope is GalNAcα(1-3)[Fucα(1-2)]Gal; and a B antigen includes Galactose glycosidically bonded to the O antigen or its epitope is Galα(1-3)[Fucα(1-2)]Gal. The structures of epitopes are depicted below:

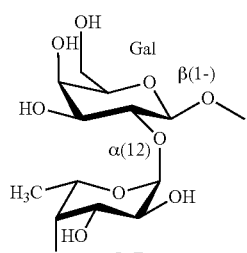

O (or H) antigen

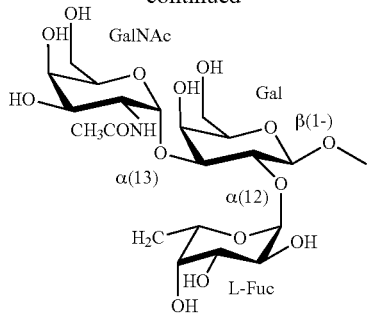

A antigen

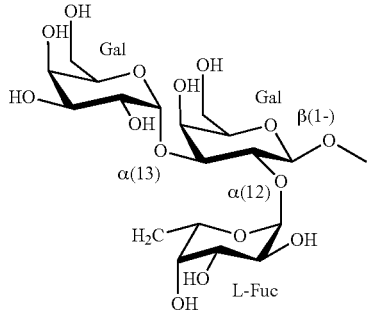

B antigen

These antigens can be further divided into six subtypes based on linkage arrangement The examples of A and B type 2 saccharides for conjugation with pHLIP® are shown below:

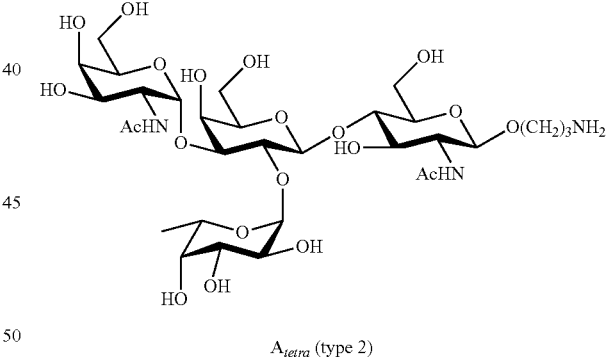

A$_{tetra}$ (type 2)

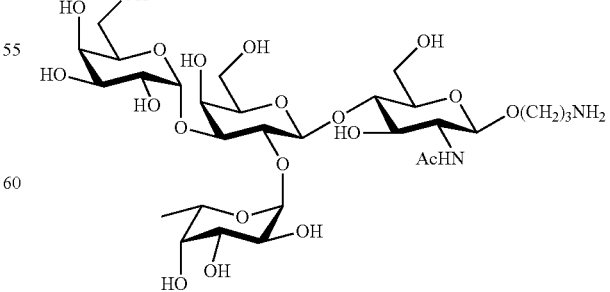

B$_{tetra}$ (type 2)

The epitope of A antigen conjugated with membrane non-inserting part of pHLIP® is used in patients with blood groups B and O; the epitope of B antigen conjugated with membrane non-inserting part of pHLIP® could be used in patients with blood groups A and O, and patients with blood group AB needs to get infusion of antibodies (isohemagglutinins). Structures below are examples of derivatives of synthetic epitopes of type 2 A antigen, B antigen and O antigen ready for conjugation with membrane non-inserting part of pHLIP®:

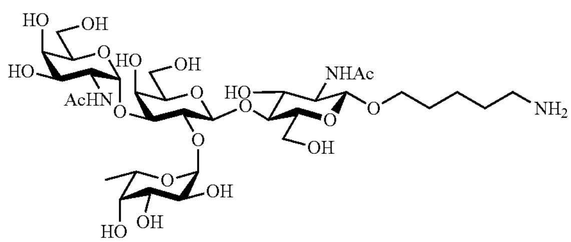

A antigen

-continued

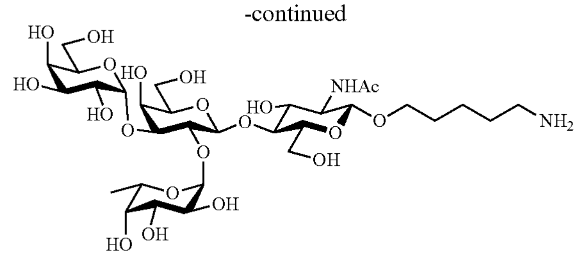

B antigen

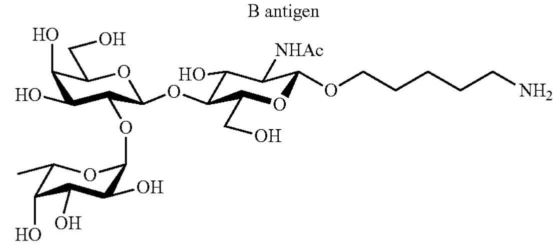

O antigen

N-Linked Carbohydrates:

Mannose-N-acetylgalactosamine [$(Man)_3(GlcNAc)_2$] attached to pHLIP®

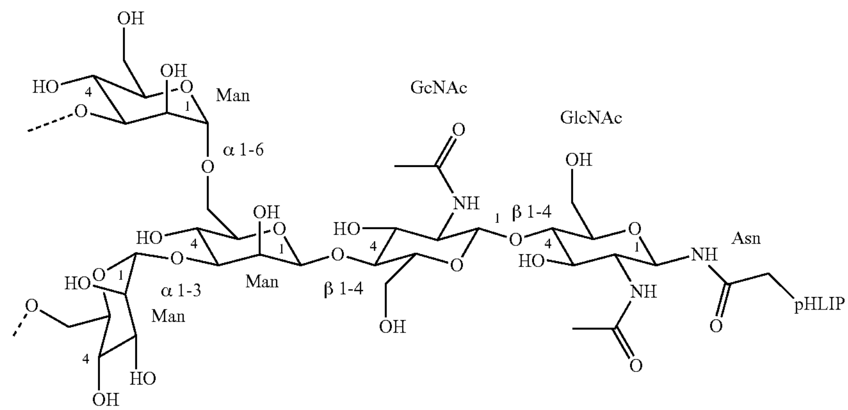

Specific examples might include three types: high mannose, complex, and hybrid (FIGS. 7A, 7B, and 7C, respectively).

Globo H Carbohydrate Epitope

Globo H is a hexasaccharide, which is expressed on the surface of some cancers cells, specifically lung cancer, breast cancer and prostate cancer, and in some tumors (depicted below):

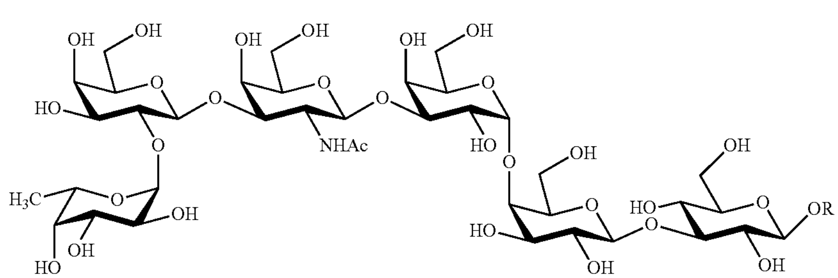

Sialic Acid Antigens/Epitopes

Sialic acid antigen (and its derivatives) for binding with hemagglutinin is also used as the carbohydrate epitope for the compositions and methods described herein:

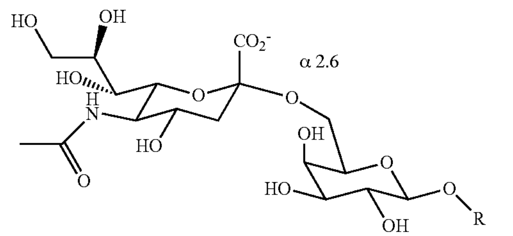

Gal

Sia a(2,6) Gal

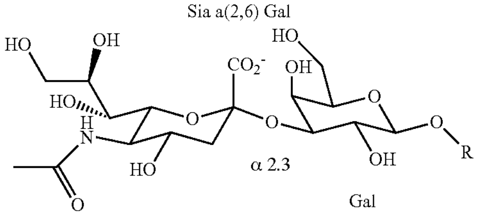

Gal

Sia a(2,3) Gal

The sialic acid family includes 43 derivatives of the nine-carbon sugar neuraminic acid, but these acids rarely appear free in nature. Normally they can be found as components of oligosaccharide chains of mucins, glycoproteins and glycolipids occupying terminal, non-reducing positions of complex carbohydrates on both external and internal membrane areas where they are very exposed and develop important functions. Exemplarily sialic acid derivatives include:

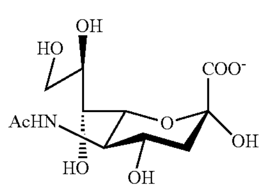

N-Acetylneuraminic acid
Neu5Ac

2-Keto-3-deoxynonic acid
Kdn

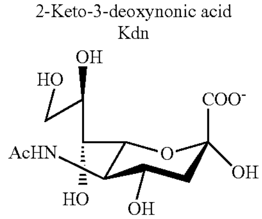

N-Acetylneuraminic acid
Neu5Ac

-continued

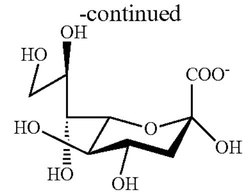

2-Keto-3-deoxynonic acid
Kdn

Example 2: Tethering Rhamnose to Cancer Cells by pHLIP®

Two different pHLIP® constructs were synthesized with L-rhamnose:

i) Ser residue coupled with rhamnose (Rha) was added to the pHLIP® sequence during the peptide synthesis to obtain:

Rha-pHLIP®: AS(Rha)DDQNPWRAYLDLLFPTDTLLLDLLWA (SEQ ID NO: 468) (construct was synthesized and purified by Iris Biotech, GmbH)

ii) Rhamnose-PEG12-malemide was synthesized and purified by Iris Biotech, GmbH (FIG. 15) and was coupled with a single Cys residue at the pHLIP® peptide's N-terminal end (ACDDQNPWRAYLDLLFPTDTLLLDLLWA SEQ ID NO: 469) to obtain Rha-PEG12-pHLIP®.

Progression of the reaction was monitored by (RP-HPLC) (the gradient: water and acetonitrile with 0.05% TFA). Purification of Rha-PEG12-pHLIP® was conducted using RP-HPLC followed by lyophilization. The construct purity and identity was established by analytical RP-HPLC and surface-enhanced laser desorption/ionization time of flight (SELDI-TOF) mass spectroscopy, respectively. Constructs concentration were calculated by absorbance at 280 nm using pHLIP® extinction coefficient.

Induction of an immunological response requires a proper positioning of carbohydrate epitope at the surface of tumor cells. This was verified on 3-D tumor cancer cell culture (tumor spheroids). Briefly, a 2% agarose solution was made by dissolving in pH 7.4 PBS. 150 μL of the solution is pipetted into each well of a 48-well flat bottom tissue culture plate. After the agarose gel sufficiently settled (~1 h), 150 μL of DMEM supplemented with 10% FBS and ciprofloxacin.HCl was added to each well. The covered plate was left in a humidified atmosphere at 37° C. and 5% $CO_2$ in cell culture incubator for 24 h. On the next day, the excess medium was removed from the agarose layer. HeLa cells (10,000 cells) in 200 μL of DMEM containing 2% matrigel were added into each well and incubated for 3-4 days to allow the formation of spheroids. Matrigel was dissolved on ice overnight and added in ice cold DMEM at a concentration of 2.5% (to obtain a final concentration of 2% once added to the wells). Then the mixture was heated to 37° C. before being combined with the cells. Tumor spheroids were incubated in 50 μL of PBS buffer, pH 6.3 containing 0-2 μM Rha-pHLIP® or Rha-PEG12-pHLIP® in a humidified atmosphere of 5% $CO_2$ at 37° C. for 30 min. After treatment, the spheroids were washed several times in 1 mL of PBS. Next, spheroids were treated at pH 7.4 with Lectin conjugated with Cy3, which recognizes rhamnose followed by washing. The spheroids were imaged using a fluorescent inverted confocal microscope. The representative images are shown in FIG. 16.

Some non-specific binding of lectin-Cy3 to cancer cells was observed; however when tumor spheroids were pre-treated with Rha-pHLIP® or Rha-PEG12-pHLIP®, a much stronger binding of lectin-Cy3 was observed, and thus, fluorescence, was observed. This data indicated that pHLIP® positioned carbohydrate epitope at the surface of cancer cells in 3-D cell culture, and epitope was recognized by the corresponding antibody.

Figure 17A:
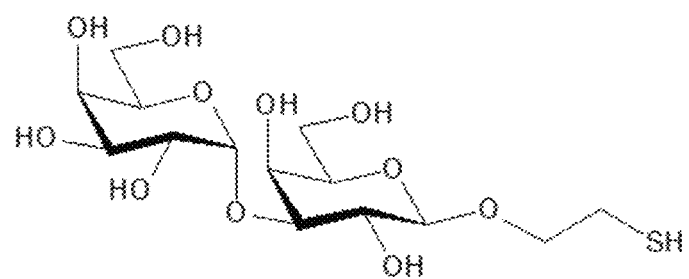
FIGS. 17A and 17B are schematics of chemical structures of di-Gal (2-Mercaptoethyl 3-O-(α-D-galactopyranosyl)-β-D-galactopyranoside) (FIG. 17A) and tri-Gal-PEG4 (Galα(1,3)Galβ(1,4)Glc-PEG4) (FIG. 17B).
Figure 17B:
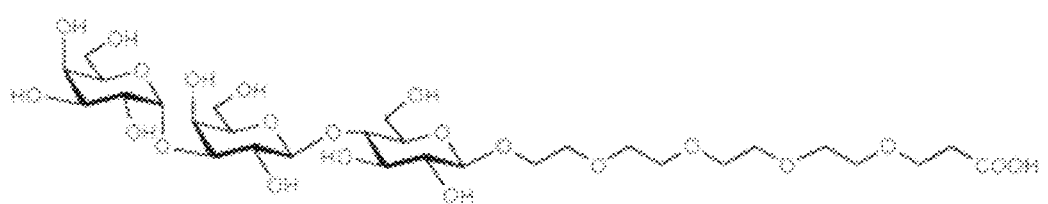

Example 3: Tethering α-Gal to Cancer Cells by pHLIP® and Activating Immune Response in Animals Several different pHLIP® constructs were synthesized with the α-Gal epitope:
i) di-Gal-SH was synthesized by Synthose, Inc. (FIG. 17A) is coupled with pHLIP® (AKDDQNPWRAYLD-LLFPTDTLLLDLLWA SEQ ID NO: 474) to obtain di-Gal-di-Gal-PEG4-pHLIP® and di-Gal-PEG12-pH-LIP®:
iii) tri-Gal (FIG. 17B) was coupled with pHLIP® ACDDQNPWRAYLDLLFPTDTLLLDLLWA (SEQ ID NO: 469) to obtain tri-Gal-PEG4-pHLIP® and is synthesized and purified by Iris Biotech, GmbH.

To obtain di-Gal-pHLIP®, di-Gal-PEG4-pHLIP® and di-Gal-PEG12-pHLIP®, first, N-α-maleimidoacet-oxysuc-cinimide ester (AMAS), NHS-PEG4-malemide, NHS-PEG12-malemide or cross-linkers were conjugated with single Lys residue at the N-terminal end of pHLIP® peptide to obtain AMAS-pHLIP® and malemide-PEGs-pHLIP®. The progression of the reactions and purification were carried out using the reverse phase HPLC (the gradient: water and acetonitrile with 0.05% TFA).

At the second step, di-Gal-malemide was coupled with AMAS-pHLIP® malemide-PEG4-pHLIP® or malemide-PEG12-pHLIP®. Progressions of the reactions and purification was conducted using RP-HPLC the gradient: water and acetonitrile with 0.05% TFA) followed by lyophilization. The constructs purity and identity were established by analytical RP-HPLC and surface-enhanced laser desorption/ionization time of flight (SELDI-TOF) mass spectroscopy, respectively. Constructs concentration were calculated by absorbance at 280 nm using pHLIP® extinction coefficient.

Effect on Length of Linker di-Gal epitopes conjugated to pHLIP® using different lengths of linkers (di-Gal-pHLIP®, di-Gal-PEG4-pHLIP® and di-Gal-PEG12-pHLIP®) were investigated on tumor spheroids. Briefly, a 2% agarose solution was made by dissolving in pH 7.4 PBS. 150 µL of the solution was pipetted into each well of a 48-well flat bottom tissue culture plate. After the agarose gel sufficiently settled (~1 h), 150 µL of DMEM supplemented with 10% FBS and ciprofloxacin.HCl was added to each well. The covered plate was left in a humidified atmosphere at 37° C. and 5% $CO_2$ in cell culture incubator for 24 h. On the next day, the excess medium was removed from the agarose layer. HeLa cells (10,000 cells) in 200 µL of DMEM containing 2% matrigel were added into each well and incubated for 3-4 days to allow the formation of spheroids. Matrigel was dissolved on ice overnight and added in ice cold DMEM at a concentration of 2.5% (to obtain a final concentration of 2% once added to the wells). Then the mixture was heated to 37° C. before being combined with the cells. Tumor spheroids were incubated in 50 µL of PBS buffer, pH 6.3 containing 0-2 µM di-Gal-pHLIP®, di-Gal-PEG4-pHLIP® or di-Gal-PEG12-pHLIP® in a humidified atmosphere of 5% CO2 at 37° C. for 30 min. After treatment, the spheroids were washed several times in 1 mL of PBS. Next, spheroids were treated with anti-alpha-Gal human IgG antibody (clone m86) conjugated with 647 nm fluorescent dye, at pH 7.4 followed by washing. The spheroids were imaged using a fluorescent inverted confocal microscope.

Figure 18:
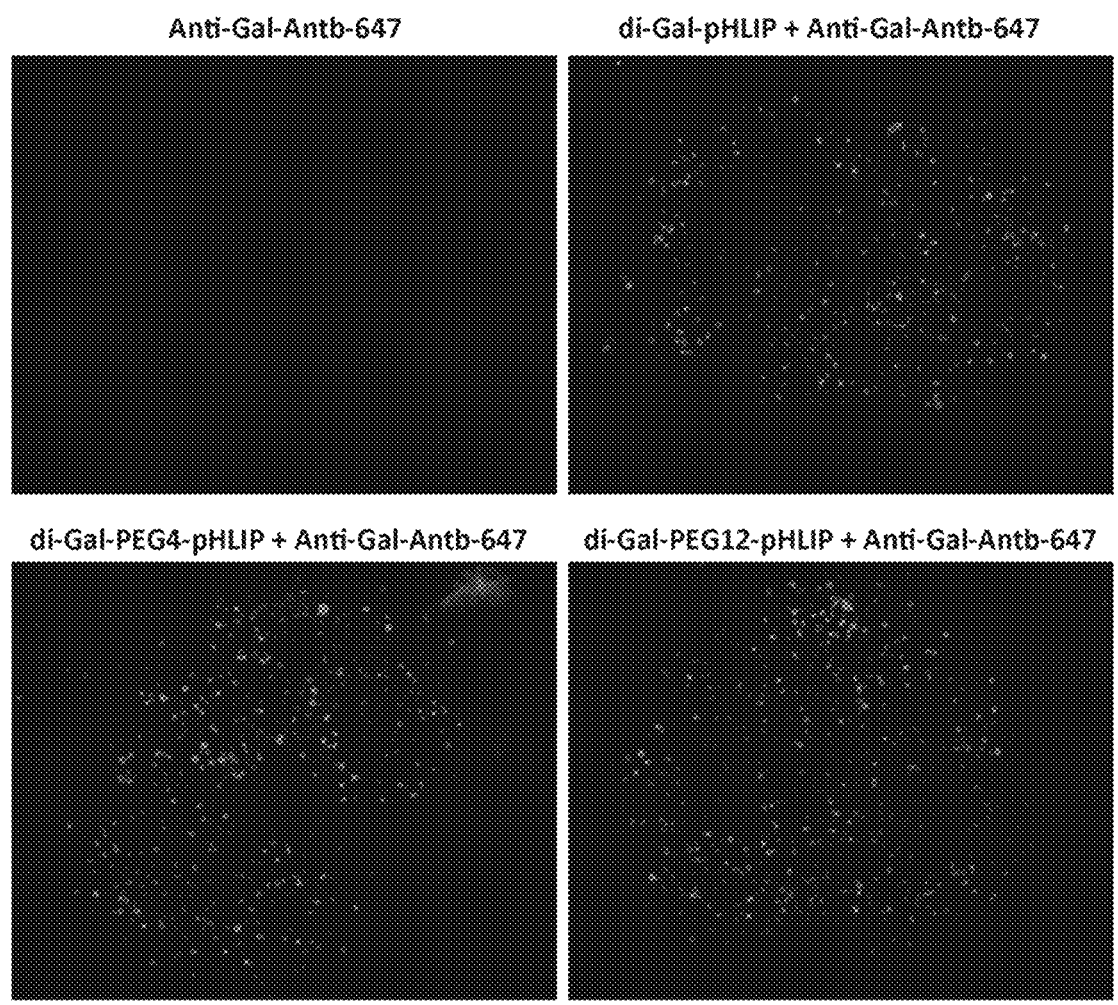
FIG. 18 depicts fluorescent images obtained from tumor spheroids treated with an anti-alpha-Gal Ig antibody (labeled with fluorescent-647 nm dye, clone m86 (from Absolute Antibody) antibody followed by washing or treated with di-Gal-pHLIP®, di-Gal-PEG4-pHLIP® or di-Gal-PEG12-pHLIP® followed by washing and treatment with an anti-Gal-647 Ig antibody followed again by washing.

The representative images are shown in FIG. 18. With all linkers (e.g., no linker, PEG4 or PEG12), the antibody recognized and bound the α-Gal epitope positioned at the surface of cancer cells by pHLIP® (FIG. 18).

In Vivo Experimental Data

Tri-Gal-PEG4-pHLIP® was used in animal studies described herein. The α-Gal epitope is absent only in humans, apes and Old World monkeys, however it is profusely generated in non-primate mammals, prosimians and New World monkeys. Glycosylation enzyme α1,3 galactosyltransferases (α1,3GT) allows transfer of galactose from uridine diphosphate (UDP)-gal to N-acetyllactosamine, producing the α-Gal epitope. Since humans and Old World primates lack the α-Gal epitope, they are not immunotolerant to it, and produce large quantities of anti-Gal antibodies. The presence of α-Gal epitope on the surface of animal cells (mouse cells) requires use of knockout animals, where the α1,3GT gene locus is disrupted and α1,3 galactosyltransferases is not produced and therefore synthesis of α-Gal epitope is not occurring.

Mice deficient in α1-3 gylactosyltransferase 2 (A3galt2) on 129/SvEv-057BL/6J background heterozygous breeding pairs was obtained from Taconic Biosciences. The knockout mouse model is described in the article entitled "Normal development and function of invariant natural killer T cells in mice with isoglobotrihexosylceramide (iGb3) deficiency" by Porubsky et al. *PNAS* 2007 Apr. 3; 104(14): 5977-5982, incorporated herein by reference in its entirety.

Mice were bred such that a male was housed with two females in harem. Breeding males were separated after the sperm plug was noted or before parturition day. To obtain DNA for mouse genotyping tail biopsies were done on days 10-21 of animal age. The genotyping assay was performed on samples by Taconic. The colony of homozygous mice was established.

All animal studies with the Gal-pHLIP® construct were conducted according to the animal protocol AN1920-003 approved by the Institutional Animal Care and Use Committee at the University of Rhode Island, in compliance with the principles and procedures outlined by the National Institutes of Health for the care and use of animals. Homo- and heterozygous A3galt2-knockout female and male mice on 129/SvEv-C57BL/6J background were used in the study.

First, immunization of mice was performed to develop antibodies against tri-Gal epitope. Briefly, at day 1 mice were immunized with Galα1-3Galβ1-4Glc-HSA (HSA: human serum albumin) from Dextra Laboratories, 20 µg/mouse emulsified in complete Freund's adjuvant. Booster injections of Galα1-3Galβ1-4Glc-HSA emulsified in incomplete Freund's adjuvant were administered at days 13, 20 and 27. The blood samples were collected at day 1 (prior immunization) and day 31 (after completion of immunization), serum was isolated and kept at −80 C before use in ELISA.

ELISA assay was performed to confirm presence of antibodies against tri-Gal epitope. Briefly, 25 µl of 4 µg/ml Galα1-3Galβ1-4Glc-BSA (BSA: bovine serum albumin) in 100 mM bicarbonate/carbonate buffer was plated to 96-well half-area plates and incubated overnight at 37° C. Solution was removed, and wells were treated with 1% BSA/PBS buffer for 1 h at 37° C. 25 µl of mouse serum in 2% BSA/PBS at different dilution ratios was added to wells and incubated for 24 h at +4° C. Wells were washed 5 times with wash solution, and incubated with peroxidase-conjugated donkey anti-mouse IgG in 1% BSA/PBS buffer for 2 hours at RT. Wells were washed 5 times with wash solution. TMB (3,3',5,5'-Tetramethylbenzidine) substrate solution was added to wells, and plates were incubated for 10-15 min. After sufficient color development, reaction was stopped by adding the equal volume of 10% sulfuric acid to the wells. Absorbance was measured at 450 nm using plate reader. The average absorbance reading in the serum samples of all animals with dilution of 1:500 as OD=1.2 (subtracting values of OD obtained on samples prior to immunization), and the average absorbance reading in the serum samples with dilutions of 1:5000 is OD=0.5, which indicated that antibodies against tri-Gal was developed in animals (a titer of 1:5000).

B16-F10 melanoma murine cancer cells were used in the study, since it is known that these murine cells are lacking expression of Gal epitope on their surface. At the same time, LLC (Lewis Lung Carcinoma) cells were used as a positive control, which have higher natural expression of Gal epitope. The control group of animals (negative control) developed B16-F10 tumor in the flank (1 million cells/mouse) and did not receive any treatment. The positive control was a group of mice with implanted LLC cancer cells (1 million cells/mouse). The treated group was a group of animals with B16-F10 tumors, which obtained tri-Gal-PEG4-pHLIP® construct for 10 consecutive days in a form of intraperitoneal (IP) injections (450 µl of 80 µM).

Figure 19:
FIG. 19 depicts an image of B16-F10 murine melanoma tumors: top row—non-treated (control) animals—bottom row—animals treated with tri-Gal-PEG4-pHLIP®.
Figure 20:
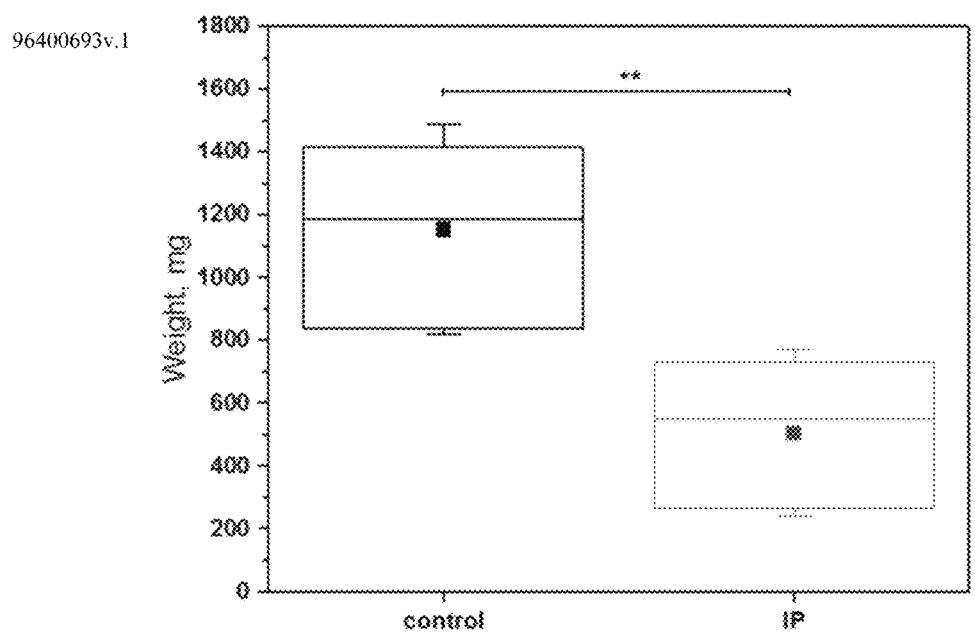
FIG. 20 depicts a box plot presenting mean (filled square), medial, 25 and 75 percentiles (the box itself) and standard deviation values of the tumor weights after IP treatment with tri-Gal-PEG4-pHLIP® compared to the tumors obtained from the control (non-treated) group. P-level was calculated using two-tailed test.

The overall total dose of tri-Gal received in the course of multiple IP injections was 60 mg/kg. When the tumor reached about 1 cm$^3$ (about 1 g) in the control (non-treated) group, the animals were sacrificed; tumors were collected (FIG. 19) and weighed (FIG. 20).

About 65% of tumor weight reduction was observed after IP administration of tri-Gal-PEG4-pHLIP®. In a positive control group, where animals were developing LLC tumor, the tumor development was suppressed and on day 12$^{th}$ after cancer cells implantation tumor was ~60% smaller compared to the LLC tumors developed in the wild-type animals.

Example 4: Tethering Two Carbohydrate Epitopes by pHLIP® to Cancer Cells to Bind Two Heads of an Ig Antibody To enhance performance of antibodies and enhance immune response, it is important to promote binding of both heads of IgG with 2 epitopes coupled to the same pHLIP® peptide. To achieve this goal a carbohydrate epitope (described above) is conjugated with PEG12 or PEG24 links, which then, is coupled with one of the following pHLIP® peptides:

```
                                           (SEQ ID NO: 470)
Ac-AKQNDDQNKPWRAYLDLLFPTDTLLLDLLWA (SEQ ID NO: 471)
ACQNDDQNCPWRAYLDLLFPTDTLLLDLLWA
```

PEG12 and PEG24 can be used to introduce a spacer for 5 nm and 10 nm, respectively. The six residues (QNDDQN (SEQ ID NO: 472) between points of PEG conjugation to pHLIP provides additional space of a few nanometers. Alternatively, QDNDQN (SEQ ID NO: 6) may be used. Thus, two epitopes at the single pHLIP construct binds two heads of Ig antibody, since the distance between heads is 5-25 nm, and thus achieves enhanced avidity, enhanced affinity and immune response. Alternatively, the distance may be about 10 nm, or 10-15 nm, which corresponds to a typical distance between the two antigen binding sites binding sites of an antibody.

Example 5

In aspects, provided herein is a composition comprising a purified carbohydrate epitope and a pHLIP® peptide. For example, the composition has the formula of Carb-Linker-Pept wherein "Carb" is a carbohydrate epitope; wherein "Linker" is a non-cleavable linker compound or a membrane non-inserting end of the pHLIP® peptide further comprises an amino acid extension; wherein "Pept" is a pHLIP® peptide comprising the sequence AXDDQNPWRAYLDLL-FPTDTLLLDLLWA (SEQ ID NO: 3) or AXDQDNP-WRAYLDLLFPTDTLLLDLLWA (SEQ ID NO: 4), where "X" is a functional group, selected from a lysine, a cysteine, a serine, a threonine, or an Azido-containing amino acid; wherein each "-" is a covalent bond.

In embodiments, the carbohydrate epitope and peptide are connected by a non-cleavable linker or by an extension of the pHLIP® peptide membrane non-inserting terminus.

In embodiments, the pHLIP® peptide extension is a poly-Glycine peptide.

In other embodiments, the linker has a polyethylene glycol (PEG) polymer, wherein the PEG polymer ranges from 4 to 24 PEG units. In embodiments, the linker has a polyethylene glycol polymer. For example, the polymer ranges in size from 200 Daltons to 20 kiloDaltons.

In embodiments, the carbohydrate epitope has a glycan comprising an N-linked glycan, an O-linked glycan, or any combination thereof. For example, the glycan includes Galactose-α-1,3-Galactose or derivatives thereof. In other examples, the glycan includes tri-Gal or derivatives thereof.

In embodiments, the N-linked glycan and the O-linked glycan have the core structure GlcNAc2Man3, Mannose-N-acetylgalactosamine [(Man)3(GlcNAc)2], α-rhamnose, Globo H, or sialic acid or derivatives thereof.

In other examples, the carbohydrate epitope has a blood antigen.

In embodiments, the composition described herein has 2 or more pHLIP® peptides. For example, the composition has 2 or more carbohydrate epitopes. In examples, the 2 carbohydrate epitopes are linked to a single pHLIP® peptide.

In embodiments, the composition has the formula of Carb-Linker-Pept-Linker-Carb wherein "Carb" is a carbohydrate epitope; wherein "Linker" is a polyethylene glycol linker; wherein "Pept" is a pHLIP® peptide comprising the sequence Ac-AKQNDDQNKPWRAYLDLLFPTDTLLLD-LLWA (SEQ ID NO: 470) or Ac-AKQNDNDNKPWRAY-LDLLFPTDTLLLDLLWA (SEQ ID NO: 479) or ACQNDDQNCPWRAYLDLLFPTDTLLLDLLWA (SEQ ID NO: 471) or ACQNDNDNCPWRAYLDLL-FPTDTLLLDLLWA (SEQ ID NO: 480) wherein each "-" is a covalent bond.

In aspects, provided herein is a method of inducing an immune response in a diseased tissue in a subject, including administering to a subject a composition comprising a carbohydrate epitope and a pHLIP® peptide. In embodiments, the subject has a solid tumor.

In embodiments, the composition is injected directly into a tumor mass. In other embodiments, the composition is systemically administered. In embodiments, a biological effect of the composition is at least 20% greater than that delivered in the absence of said composition.

In other embodiments, the composition targets preferentially to a diseased tissue compared to a healthy tissue, thereby minimizing damage to said healthy tissue.

In embodiments, provided herein is a method for promoting an immune response in a subject, including administering to a subject the composition described herein, wherein said method comprises placement of said carbohydrate epitope on tumor cell of said subject.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

As used herein, an "isolated" or "purified" carbohydrate molecule, nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) or polypeptide is free of the amino acid sequences, or nucleic acid sequences that flank it in its naturally-occurring state. Purified also defines a degree of sterility that is safe for administration to a human subject, e.g., lacking infectious or toxic agents. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

The terms "subject," "patient," "individual," and the like as used herein are not intended to be limiting and can be generally interchanged. That is, an individual described as a "patient" does not necessarily have a given disease, but may be merely seeking medical advice.

As used herein, the singular forms "a," "an," and "the" include the plural reference unless the context clearly dictates otherwise. Thus, for example, a reference to "a disease," "a disease state", or "a nucleic acid" is a reference to one or more such embodiments, and includes equivalents thereof known to those skilled in the art and so forth.

As used herein, "treating" encompasses, e.g., inhibition, regression, or stasis of the progression of a disorder. Treating also encompasses the prevention or amelioration of any symptom or symptoms of the disorder. As used herein, "inhibition" of disease progression or a disease complication in a subject means preventing or reducing the disease progression and/or disease complication in the subject.

As used herein, a "symptom" associated with a disorder includes any clinical or laboratory manifestation associated with the disorder, and is not limited to what the subject can feel or observe.

As used herein, "effective" when referring to an amount of a therapeutic compound refers to the quantity of the compound that is sufficient to yield a desired therapeutic response without undue adverse side effects (such as toxicity, irritation, or allergic response) commensurate with a reasonable benefit/risk ratio when used in the manner of this disclosure.

As used herein, "pharmaceutically acceptable" carrier or excipient refers to a carrier or excipient that is suitable for use with humans and/or animals without undue adverse side effects (such as toxicity, irritation, and allergic response) commensurate with a reasonable benefit/risk ratio. It can be, e.g., a pharmaceutically acceptable solvent, suspending agent or vehicle, for delivering the instant compounds to the subject.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. Such sequences that are at least about 80% identical are said to be "substantially identical." In some embodiments, two sequences are 100% identical. In certain embodiments, two sequences are 100% identical over the entire length of one of the sequences (e.g., the shorter of the two sequences where the sequences have different lengths). In various embodiments, identity may refer to the complement of a test sequence. In some embodiments, the identity exists over a region that is at least about 10 to about 100, about 20 to about 75, about 30 to about 50 amino acids or nucleotides in length. In certain embodiments, the identity exists over a region that is at least about 50 amino acids in length, or more preferably over a region that is 100 to 500, 100 to 200, 150 to 200, 175 to 200, 175 to 225, 175 to 250, 200 to 225, 200 to 250 or more amino acids in length.

For sequence comparison, typically one sequence acts as a reference sequence, to which test sequences are compared. In various embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In various embodiments, a comparison window is the entire length of one or both of two aligned sequences. In some embodiments, two sequences being compared comprise different lengths, and the comparison window is the entire length of the longer or the shorter of the two sequences. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

In various embodiments, an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information, as known in the art. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed:

1. A method of inducing an immune response in a diseased tissue in a subject, comprising administering to a subject a composition comprising a carbohydrate epitope and a pHLIP® peptide,
wherein said composition comprising the formula of Carb-Linker-Pept
wherein "Carb" is a carbohydrate epitope;
wherein "Linker" is a non-cleavable linker compound or a membrane non-inserting end of the pHLIP® peptide further comprises an amino acid extension;
wherein "Pept" is a pHLIP® peptide comprising the sequence
AXDDQNPWRAYLDLLFPTDTLLLDLLW (SEQ ID NO: 481) or
AXDQDNPWRAYLDLLFPTDTLLLDLLW (SEQ ID NO: 482), where "X" is a functional group, selected from a lysine, a cysteine, a serine, a threonine, or an Azido-containing amino acid;
wherein each "-" is a covalent bond.

2. The method of claim 1, wherein said carbohydrate epitope and said peptide are connected by a non-cleavable linker or by an extension of the pHLIP® peptide membrane non-inserting terminus.

3. The method of claim 2, wherein said pHLIP® peptide extension is a poly-Glycine peptide.

4. The method of claim 1, wherein said linker comprises a polyethylene glycol (PEG) polymer, wherein the PEG polymer ranges from 4 to 24 PEG units.

5. The method of claim 4, wherein said linker comprises a polyethylene glycol polymer.

6. The method of claim 4, wherein said polymer ranges in size from 200 Daltons to 20 kiloDaltons.

7. The method of claim 1, wherein said carbohydrate epitope comprises a blood antigen.

8. The method of claim 1, wherein said composition comprises 2 or more pHLIP® peptides.

9. The method of claim 1, wherein said composition comprises 2 or more carbohydrate epitopes.

10. The method of claim 9, wherein the 2 carbohydrate epitopes are linked to a single pHLIP® peptide.

11. The method of claim 1, wherein said composition comprising the formula of Carb-Linker-Pept-Linker-Carb
wherein "Carb" is a carbohydrate epitope;
wherein "Linker" is a polyethylene glycol linker;
wherein "Pept" is a pHLIP® peptide comprising the sequence Ac-AKQNDDQNKPWRAYLDLLFPTDTLLLDLLWA (SEQ ID NO: 470) or
Ac-AKQNDNDNKPWRAYLDLLFPTDTLLLDLLWA (SEQ ID NO: 479) or
ACQNDDQNCPWRAYLDLLFPTDTLLLDLLWA (SEQ ID NO: 471) or
ACQNDNDNCPWRAYLDLLFPTDTLLLDLLWA (SEQ ID NO: 480)
wherein each "-" is a covalent bond.

12. The method of claim 1, wherein said subject comprises a solid tumor.

13. The method of claim 1, wherein said composition is injected directly into a tumor mass.

14. The method of claim 1, wherein said composition is systemically administered.

15. The method of claim 1, wherein a biological effect of said composition is at least 20% greater than that delivered in the absence of said composition.

16. The method of claim 1, wherein said composition targets preferentially to a diseased tissue compared to a healthy tissue, thereby minimizing damage to said healthy tissue.

17. The method of claim 1, wherein the carbohydrate epitope is delivered to a cell surface of the diseased tissue.

18. The method of claim 1, wherein the carbohydrate epitope is preferentially inserted into a cell membrane of the diseased tissue.

19. The method of claim 1, wherein the carbohydrate epitope comprises a glycan comprising an N-linked glycan, an O-linked glycan, or any combination thereof.

20. The method of claim 19, wherein the glycan comprises Galactose-α-1,3-Galactose or derivatives thereof.

21. The method of claim 19, wherein the carbohydrate epitope comprises a plurality of glycans.

22. The method of claim 19, wherein the glycan comprises tri-Gal or derivatives thereof.

23. The method of claim 19, wherein the N-linked glycan and the O-linked glycan comprises the core structure GlcNAc2Man3, Mannose-N-acetylgalactosamine [(Man)3(GlcNAc)2], α-rhamnose, Globo H, or sialic acid or derivatives thereof.

24. The method of claim 1, wherein said method comprises placement of said carbohydrate epitope on tumor cell of said subject.

* * * * *

UNITED STATES PATENT AND TRADEMARK OFFICE
CERTIFICATE OF CORRECTION

| | |
|---|---|
| PATENT NO. | : 11,267,853 B2 |
| APPLICATION NO. | : 16/775046 |
| DATED | : March 8, 2022 |
| INVENTOR(S) | : Yana K. Reshetnyak et al. |

It is certified that error appears in the above-identified patent and that said Letters Patent is hereby corrected as shown below:

In the Specification

At Column 11, Line Number 15, please insert the following text as the first paragraph under the "DESCRIPTION OF THE DRAWINGS":
-- The patent or application file contains at least one drawing executed in color. Copies of this patent or patent application publication with color drawing(s) will be provided by the Office upon request and payment of the necessary fee. --

Signed and Sealed this
Fourteenth Day of June, 2022

*Katherine Kelly Vidal*

Katherine Kelly Vidal
*Director of the United States Patent and Trademark Office*

```
                          SEQUENCE LISTING

<160> NUMBER OF SEQ ID NOS: 482

<210> SEQ ID NO 1
    <211> LENGTH: 28
    <212> TYPE: PRT
    <213> ORGANISM: Artificial Sequence
    <220> FEATURE:
    <223> OTHER INFORMATION: Description of Artificial Sequence: Synthetic
          peptide
    <220> FEATURE:
    <221> NAME/KEY: MOD_RES
    <222> LOCATION: (1)..(2)
    <223> OTHER INFORMATION: Any amino acid
    <220> FEATURE:
    <223> OTHER INFORMATION: See specification as filed for detailed
          description of substitutions and preferred embodiments

<400> SEQUENCE: 1

Xaa Xaa Asp Asp Gln Asn Pro Trp Arg Ala Tyr Leu Asp Leu Leu Phe
    1               5                   10                  15

Pro Thr Asp Thr Leu Leu Leu Asp Leu Leu Trp Ala
                    20                  25

<210> SEQ ID NO 2
    <211> LENGTH: 28
    <212> TYPE: PRT
    <213> ORGANISM: Artificial Sequence
    <220> FEATURE:
    <223> OTHER INFORMATION: Description of Artificial Sequence: Synthetic
          peptide
    <220> FEATURE:
    <221> NAME/KEY: MOD_RES
    <222> LOCATION: (1)..(2)
    <223> OTHER INFORMATION: Any amino acid
    <220> FEATURE:
    <223> OTHER INFORMATION: See specification as filed for detailed
          description of substitutions and preferred embodiments

<400> SEQUENCE: 2

Xaa Xaa Asp Gln Asp Asn Pro Trp Arg Ala Tyr Leu Asp Leu Leu Phe
    1               5                   10                  15

Pro Thr Asp Thr Leu Leu Leu Asp Leu Leu Trp Ala
                    20                  25

<210> SEQ ID NO 3
    <211> LENGTH: 28
    <212> TYPE: PRT
    <213> ORGANISM: Artificial Sequence
    <220> FEATURE:
    <223> OTHER INFORMATION: Description of Artificial Sequence: Synthetic
          peptide
    <220> FEATURE:
    <221> NAME/KEY: MOD_RES
    <222> LOCATION: (2)..(2)
    <223> OTHER INFORMATION: Lys, Cys or an Azido-containing amino acid
    <220> FEATURE:
    <223> OTHER INFORMATION: See specification as filed for detailed
          description of substitutions and preferred embodiments
```

```
<400> SEQUENCE: 3

Ala Xaa Asp Asp Gln Asn Pro Trp Arg Ala Tyr Leu Asp Leu Leu Phe
1               5                   10                  15

Pro Thr Asp Thr Leu Leu Leu Asp Leu Leu Trp Ala
            20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Cys or an Azido-containing amino acid
<220> FEATURE:
<223> OTHER INFORMATION: See specification as filed for detailed
      description of substitutions and preferred embodiments

<400> SEQUENCE: 4

Ala Xaa Asp Gln Asp Asn Pro Trp Arg Ala Tyr Leu Asp Leu Leu Phe
1               5                   10                  15

Pro Thr Asp Thr Leu Leu Leu Asp Leu Leu Trp Ala
            20                  25

<210> SEQ ID NO 5
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Lys, Cys or an Azido-containing amino acid
<220> FEATURE:
<221> NAME/KEY: MOD_RES
<222> LOCATION: (3)..(12)
<223> OTHER INFORMATION: Any amino acid
<220> FEATURE:
<221> NAME/KEY: MISC_FEATURE
<222> LOCATION: (3)..(12)
<223> OTHER INFORMATION: This region may encompass 1-10 residues
<220> FEATURE:
<221> NAME/KEY: MOD_RES
<222> LOCATION: (13)..(13)
<223> OTHER INFORMATION: Lys, Cys or an Azido-containing amino acid
<220> FEATURE:
<223> OTHER INFORMATION: See specification as filed for detailed
      description of substitutions and preferred embodiments

<400> SEQUENCE: 5

Ala Xaa Xaa Xaa Xaa Xaa Xaa Xaa Xaa Xaa Xaa Xaa Xaa Pro Trp Arg
1               5                   10                  15

Ala Tyr Leu Asp Leu Leu Phe Pro Thr Asp Thr Leu Leu Leu Asp Leu
            20                  25                  30

Leu Trp Ala
        35

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 6

Gln Asp Asn Asp Gln Asn
1               5

<210> SEQ ID NO 7
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Glu Gln Asn Pro Ile Tyr
1               5

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Trp Ala Arg Tyr Ala Asp Trp Leu Phe Thr Thr Pro Leu Leu Leu Leu
1               5                   10                  15

Asp Leu Ala Leu Leu Val
            20

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Ala Asp Glu Gly Thr
1               5

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Cys Asp Gln Asp Asn Pro Trp Arg Ala Tyr Leu Asp Leu Leu Phe
1               5                   10                  15

Pro Thr Asp Thr Leu Leu Leu Asp Leu Leu Trp Ala
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Lys Asp Gln Asp Asn Pro Trp Arg Ala Tyr Leu Asp Leu Leu Phe
1               5                   10                  15

Pro Thr Asp Thr Leu Leu Leu Asp Leu Leu Trp Ala
            20                  25

<210> SEQ ID NO 13
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Cys Gln Asp Asn Asp Gln Asn Cys Pro Trp Arg Ala Tyr Leu Asp
1               5                   10                  15

Leu Leu Phe Pro Thr Asp Thr Leu Leu Leu Asp Leu Leu Trp Ala
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Lys Gln Asp Asn Asp Gln Asn Lys Pro Trp Arg Ala Tyr Leu Asp
1               5                   10                  15

Leu Leu Phe Pro Thr Asp Thr Leu Leu Leu Asp Leu Leu Trp Ala
            20                  25                  30

<210> SEQ ID NO 15
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 16
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 17
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Asp Ala Asp Glu Cys Gly
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp Asp Ala Asp Glu Gly
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Lys Asp Asp Gln Asn Pro Trp Arg Ala Tyr Leu Asp Leu Leu Phe
1               5                   10                  15

Pro Thr Asp Thr Leu Leu Leu Asp Leu Leu Trp Asp Ala Asp Glu Gly
            20                  25                  30

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 20

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 21
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Cys Thr
        35

<210> SEQ ID NO 22
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Cys Gly
        35

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 24
<211> LENGTH: 36
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 24

Ala Cys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 25
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Gly
        35

<210> SEQ ID NO 27
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr Lys Cys Gly
        35

<210> SEQ ID NO 28
<211> LENGTH: 36
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 28

Ala Lys Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Cys Thr
            35

<210> SEQ ID NO 29
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr Gly
            35

<210> SEQ ID NO 30
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Cys Glu Gln Asn Pro Ile Tyr Trp Ala Arg Tyr Ala Asn Trp Leu
1               5                   10                  15

Phe Thr Thr Pro Leu Leu Leu Leu Asn Leu Ala Leu Leu Val Asp Ala
            20                  25                  30

Asp Glu Gly Thr
            35

<210> SEQ ID NO 31
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Cys Glu Gln Asn Pro Ile Tyr Trp Ala Arg Tyr Ala Lys Trp Leu
1               5                   10                  15

Phe Thr Thr Pro Leu Leu Leu Leu Lys Leu Ala Leu Leu Val Asp Ala
            20                  25                  30

Asp Glu Gly Thr Gly
            35

<210> SEQ ID NO 32
<211> LENGTH: 36
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 32

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
                20                  25                  30

Asn Gln Gly Thr
            35

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
                20                  25                  30

Asp Glu Gly Thr
            35

<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
                20                  25                  30

Asp Glu Gly Thr Lys Cys Gly
            35

<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
                20                  25                  30

Asp Glu Gly Thr
            35

<210> SEQ ID NO 36
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Ala Ala Glu Gln Asn Pro Ile Tyr Trp Ala Arg Tyr Ala Asp Trp Leu
1               5                   10                  15

Phe Thr Thr Ala Leu Leu Leu Asp Leu Ala Leu Leu Val Asp Ala
            20                  25                  30

Asp Glu Gly Thr
        35

<210> SEQ ID NO 37
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Ala Glu Gln Asn Pro Ile Tyr Trp Ala Arg Tyr Ala Asp Trp Leu
1               5                   10                  15

Phe Thr Thr Pro Leu Leu Leu Glu Leu Ala Leu Leu Val Asp Ala
            20                  25                  30

Asp Glu Gly Thr
        35

<210> SEQ ID NO 38
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Ala Glu Gln Asn Pro Ile Tyr Trp Ala Arg Tyr Ala Glu Trp Leu
1               5                   10                  15

Phe Thr Thr Pro Leu Leu Leu Asp Leu Ala Leu Leu Val Asp Ala
            20                  25                  30

Asp Glu Gly Thr
        35

<210> SEQ ID NO 39
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
            20                  25                  30

Val Asp Ala Asp Glu Gly Thr
        35

<210> SEQ ID NO 40
```

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gly Glu Gln Asn Pro Ile Tyr Trp Ala Gln Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr Cys Gly
        35

<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 42
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly Thr Cys Gly
        35

<210> SEQ ID NO 43
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gly Gly Glu Gln Asn Pro Ile Tyr Trp Ala Arg Tyr Asp Ala Trp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35
```

```
<210> SEQ ID NO 44
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gly Gly Glu Gln Asn Pro Ile Tyr Trp Ala Arg Tyr Ala Trp Asp Leu
1               5                   10                  15

Phe Thr Thr Pro Leu Leu Leu Asp Leu Ala Leu Leu Val Asp Ala
            20                  25                  30

Asp Glu Gly Thr Cys Gly
        35

<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Ala Glu Gln Asn Pro Ile Tyr Trp Ala Arg Tyr Ala Asp Trp Leu
1               5                   10                  15

Phe Thr Thr Gly Leu Leu Leu Asp Leu Ala Leu Leu Val Asp Ala
            20                  25                  30

Asp Glu Gly Thr
        35

<210> SEQ ID NO 46
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Asp Asp Glu Asp Asn Pro Ile Tyr Trp Ala Arg Tyr Ala Asp Trp
1               5                   10                  15

Leu Phe Thr Thr Pro Leu Leu Leu His Gly Ala Leu Leu Val Asp
            20                  25                  30

Ala Asp Glu Cys Thr
        35

<210> SEQ ID NO 47
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Asp Asp Glu Asp Asn Pro Ile Tyr Trp Ala Arg Tyr Ala Asp Trp
1               5                   10                  15

Leu Phe Thr Thr Pro Leu Leu Leu His Gly Ala Leu Leu Val Asp
            20                  25                  30

Ala Asp Glu Thr
        35
```

```
<210> SEQ ID NO 48
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Cys Thr
        35

<210> SEQ ID NO 49
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Cys Asp Asp Asp Glu Asp Asn Pro Ile Tyr Trp Ala Arg Tyr Ala His
1               5                   10                  15

Trp Leu Phe Thr Thr Pro Leu Leu Leu Leu His Gly Ala Leu Leu Val
            20                  25                  30

Asp Ala Asp Glu Thr
        35

<210> SEQ ID NO 50
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu Gly Thr
        35

<210> SEQ ID NO 51
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Cys Thr
        35
```

<210> SEQ ID NO 52
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asp Glu Gly Thr
        35

<210> SEQ ID NO 53
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Cys Thr
        35

<210> SEQ ID NO 54
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asn
            20                  25                  30

Ala Asn Glu Gly Thr
        35

<210> SEQ ID NO 55
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 56
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Lys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ala Cys Glu Asp Gln Asn Pro Tyr Trp Ala Arg Tyr Ala Asp Trp Leu
1               5                   10                  15

Phe Thr Thr Pro Leu Leu Leu Leu Asp Leu Ala Leu Leu Val Asp Gly
            20                  25                  30

<210> SEQ ID NO 60
<211> LENGTH: 32
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 60

Ala Glu Asp Gln Asn Pro Tyr Trp Ala Arg Tyr Ala Asp Trp Leu Phe
1               5                  10                  15

Thr Thr Pro Leu Leu Leu Leu Asp Leu Ala Leu Leu Val Asp Cys Gly
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Glu Asp Gln Asn Pro Tyr Trp Ala Arg Tyr Ala Asp Trp Leu Phe
1               5                  10                  15

Thr Thr Pro Leu Leu Leu Leu Glu Leu Ala Leu Leu Val Glu Cys Gly
            20                  25                  30

<210> SEQ ID NO 62
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Lys Glu Asp Gln Asn Asp Pro Tyr Trp Ala Arg Tyr Ala Asp Trp
1               5                  10                  15

Leu Phe Thr Thr Pro Leu Leu Leu Leu Asp Leu Ala Leu Leu Val Gly
            20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Lys Glu Asp Gln Asn Pro Tyr Trp Arg Tyr Ala Asp Leu Phe
1               5                  10                  15

Thr Pro Leu Thr Leu Leu Asp Leu Leu Ala Leu Trp Asp Gly
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Glu Asp Gln Asn Pro Tyr Trp Ala Arg Tyr Ala Asp Trp Leu Phe
1               5                  10                  15

Thr Thr Pro Leu Leu Leu Leu Glu Leu Ala Leu Leu Val Cys Gly
            20                  25                  30
```

<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ala Cys Glu Asp Gln Asn Pro Tyr Trp Arg Ala Tyr Ala Asp Leu Phe
1               5                   10                  15

Thr Pro Leu Thr Leu Leu Asp Leu Leu Ala Leu Trp Asp Gly
            20                  25                  30

<210> SEQ ID NO 66
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Lys Asp Asp Gln Asn Pro Trp Arg Ala Tyr Leu Asp Leu Leu Phe
1               5                   10                  15

Pro Thr Asp Thr Leu Leu Leu Asp Leu Leu Trp Cys
            20                  25

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Cys Glu Glu Gln Asn Pro Trp Arg Ala Tyr Leu Glu Leu Leu Phe
1               5                   10                  15

Pro Thr Glu Thr Leu Leu Leu Glu Leu Leu Trp
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

```
Ala Cys Asp Asp Gln Asn Pro Trp Ala Arg Tyr Leu Asp Trp Leu Phe
1               5                   10                  15

Pro Thr Asp Thr Leu Leu Leu Asp Leu
            20                  25
```

<210> SEQ ID NO 70
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

```
Cys Asp Asn Asn Asn Pro Trp Arg Ala Tyr Leu Asp Leu Leu Phe Pro
1               5                   10                  15

Thr Asp Thr Leu Leu Leu Asp Trp
            20
```

<210> SEQ ID NO 71
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

```
Cys Glu Glu Gln Gln Pro Trp Ala Gln Tyr Leu Glu Leu Leu Phe Pro
1               5                   10                  15

Thr Glu Thr Leu Leu Leu Glu Trp
            20
```

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Cys Glu Glu Gln Gln Pro Trp Arg Ala Tyr Leu Glu Leu Leu Phe Pro
1               5                   10                  15

Thr Glu Thr Leu Leu Leu Glu Trp
            20
```

<210> SEQ ID NO 73
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Cys Asp Asp Asp Asp Asp Asn Pro Asn Tyr Trp Ala Arg Tyr Ala Asn
1               5                   10                  15

Trp Leu Phe Thr Thr Pro Leu Leu Leu Leu Asn Gly Ala Leu Leu Val
            20                  25                  30

Glu Ala Glu Glu Thr
            35
```

```
<210> SEQ ID NO 74
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Cys Asp Asp Asp Asp Asn Pro Asn Tyr Trp Ala Arg Tyr Ala Pro
1               5                   10                  15

Trp Leu Phe Thr Thr Pro Leu Leu Leu Pro Gly Ala Leu Leu Val
                20                  25                  30

Glu Ala Glu Glu
        35

<210> SEQ ID NO 75
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Thr Glu Asp Ala Asp Val Leu Leu Ala Leu Asp Leu Leu Leu Pro
1               5                   10                  15

Thr Thr Phe Leu Trp Asp Ala Tyr Arg Ala Trp Tyr Pro Asn Gln Glu
            20                  25                  30

Cys Ala

<210> SEQ ID NO 76
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 77
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Glu Gln Asn Pro Ile Tyr Trp Ala Arg Tyr Ala Asp Trp Leu Phe
1               5                   10                  15

Thr Thr Pro Cys Leu
            20

<210> SEQ ID NO 78
<211> LENGTH: 21
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 78

Ala Cys Glu Gln Asn Pro Ile Tyr Trp Ala Arg Tyr Ala Asp Trp Leu
1               5                   10                  15

Phe Thr Thr Pro Leu
            20

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ala Glu Gln Asn Pro Ile Tyr Phe Ala Arg Tyr Ala Asp Trp Leu Phe
1               5                   10                  15

Thr Thr Pro Leu
            20

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 81
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 82
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Glu Gln Asn Pro Ile Tyr Trp Ala Arg Tyr Ala Asp Leu Leu Phe
1               5                   10                  15

Pro Thr Thr Leu Ala Trp
            20

```
<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Glu Asp Gln Asn Pro Trp Ala Arg Tyr Ala Asp Leu Leu Phe Pro
1               5                   10                  15

Thr Thr Leu Ala Trp
            20

<210> SEQ ID NO 84
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Lys Glu Asp Gln Asn Pro Trp Ala Arg Tyr Ala Asp Leu Leu Phe Pro
1               5                   10                  15

Thr Thr Leu Trp
            20

<210> SEQ ID NO 85
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Cys Glu Asp Gln Asn Pro Trp Ala Arg Tyr Ala Asp Leu Leu Phe
1               5                   10                  15

Pro Thr Thr Leu Ala Trp
            20

<210> SEQ ID NO 86
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Cys Glu Asp Gln Asn Pro Trp Ala Arg Tyr Ala Asp Trp Leu Phe
1               5                   10                  15

Pro Thr Thr Leu Leu Leu Leu Asp
            20

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Cys Glu Glu Gln Asn Pro Trp Ala Arg Tyr Ala Glu Leu Leu Phe
```

```
1               5                   10                  15
Pro Thr Thr Leu Ala Trp
            20

<210> SEQ ID NO 88
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Cys Glu Glu Gln Asn Pro Trp Ala Arg Tyr Ala Glu Trp Leu Phe
1               5                   10                  15
Pro Thr Thr Leu Leu Leu Leu Glu
            20

<210> SEQ ID NO 89
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Cys Glu Glu Gln Asn Pro Trp Ala Arg Tyr Leu Glu Trp Leu Phe
1               5                   10                  15
Pro Thr Glu Thr Leu Leu Leu Glu Leu
            20                  25

<210> SEQ ID NO 90
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Cys Glu Glu Gln Asn Pro Gln Ala Glu Tyr Ala Glu Trp Leu Phe
1               5                   10                  15
Pro Thr Thr Leu Leu Leu Leu Glu
            20

<210> SEQ ID NO 91
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 91

Trp Ala Arg Tyr Ala Asp Trp Leu Phe Thr Thr Pro Leu Leu Leu Leu
1               5                   10                  15
Asp Leu Ala Leu Leu
            20

<210> SEQ ID NO 92
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 92

Tyr Ala Arg Tyr Ala Asp Trp Leu Phe Thr Thr Pro Leu Leu Leu Leu
1               5                   10                  15

Asp Leu Ala Leu Leu
            20

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 93

Trp Ala Arg Tyr Ser Asp Trp Leu Phe Thr Thr Pro Leu Leu Leu Tyr
1               5                   10                  15

Asp Leu Gly Leu Leu
            20

<210> SEQ ID NO 94
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 94

Trp Ala Arg Tyr Thr Asp Trp Phe Thr Thr Pro Leu Leu Leu Tyr Asp
1               5                   10                  15

Leu Ala Leu Leu Ala
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 95

Trp Ala Arg Tyr Thr Asp Trp Leu Phe Thr Thr Pro Leu Leu Leu Tyr
1               5                   10                  15

Asp Leu Gly Leu Leu
            20

<210> SEQ ID NO 96
```

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 96

Trp Ala Arg Tyr Ala Asp Trp Leu Phe Thr Thr Pro Leu Leu Leu Leu
1               5                   10                  15

Asp Leu Ser Leu Leu
            20

<210> SEQ ID NO 97
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 97

Leu Leu Ala Leu Asp Leu Leu Leu Pro Thr Thr Phe Leu Trp Asp
1               5                   10                  15

Ala Tyr Arg Ala Trp
            20

<210> SEQ ID NO 98
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 98

Leu Leu Ala Leu Asp Leu Leu Leu Pro Thr Thr Phe Leu Trp Asp
1               5                   10                  15

Ala Tyr Arg Ala Tyr
            20

<210> SEQ ID NO 99
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 99

Leu Leu Gly Leu Asp Tyr Leu Leu Leu Pro Thr Thr Phe Leu Trp Asp
1               5                   10                  15

Ser Tyr Arg Ala Trp
            20
```

```
<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 100

Ala Leu Leu Ala Leu Asp Tyr Leu Leu Pro Thr Thr Phe Trp Asp
1               5                   10                  15

Thr Tyr Arg Ala Trp
            20

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 101

Leu Leu Gly Leu Asp Tyr Leu Leu Leu Pro Thr Thr Phe Leu Trp Asp
1               5                   10                  15

Thr Tyr Arg Ala Trp
            20

<210> SEQ ID NO 102
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 102

Leu Leu Ser Leu Asp Leu Leu Leu Leu Pro Thr Thr Phe Leu Trp Asp
1               5                   10                  15

Ala Tyr Arg Ala Trp
            20

<210> SEQ ID NO 103
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 103

Gly Leu Ala Gly Leu Leu Gly Leu Glu Gly Leu Leu Gly Leu Pro Leu
1               5                   10                  15

Gly Leu Leu Glu Gly Leu Trp Leu Gly Leu
            20                  25
```

-continued

<210> SEQ ID NO 104
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 104

Leu Gly Leu Trp Leu Gly Glu Leu Leu Gly Leu Pro Leu Gly Leu Leu
1               5                   10                  15

Gly Glu Leu Gly Leu Leu Gly Ala Leu Gly
            20                  25

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 105

Trp Arg Ala Tyr Leu Asp Leu Leu Phe Pro Thr Asp Thr Leu Leu Leu
1               5                   10                  15

Asp Leu Leu Trp
            20

<210> SEQ ID NO 106
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 106

Trp Leu Leu Asp Leu Leu Leu Thr Asp Thr Pro Phe Leu Leu Asp Leu
1               5                   10                  15

Tyr Ala Arg Trp
            20

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 107

Trp Ala Arg Tyr Leu Glu Trp Leu Phe Pro Thr Glu Thr Leu Leu Leu
1               5                   10                  15

Glu Leu

<210> SEQ ID NO 108
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 108

Trp Ala Gln Tyr Leu Glu Leu Leu Phe Pro Thr Glu Thr Leu Leu Leu
1               5                   10                  15

Glu Trp

<210> SEQ ID NO 109
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 109

Leu Glu Leu Leu Leu Thr Glu Thr Pro Phe Leu Trp Glu Leu Tyr Arg
1               5                   10                  15

Ala Trp

<210> SEQ ID NO 110
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 110

Trp Glu Leu Leu Leu Thr Glu Thr Pro Phe Leu Leu Glu Leu Tyr Gln
1               5                   10                  15

Ala Trp

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 111

Trp Leu Phe Thr Thr Pro Leu Leu Leu Leu Asn Gly Ala Leu Leu Val
1               5                   10                  15

Glu

<210> SEQ ID NO 112
<211> LENGTH: 17

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 112

Trp Leu Phe Thr Thr Pro Leu Leu Leu Leu Pro Gly Ala Leu Leu Val
1               5                   10                  15

Glu

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 113

Trp Ala Arg Tyr Ala Asp Leu Leu Phe Pro Thr Thr Leu Ala Trp
1               5                   10                  15

<210> SEQ ID NO 114
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 114

Glu Val Leu Leu Ala Gly Asn Leu Leu Leu Leu Pro Thr Thr Phe Leu
1               5                   10                  15

Trp

<210> SEQ ID NO 115
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 115

Glu Val Leu Leu Ala Gly Pro Leu Leu Leu Leu Pro Thr Thr Phe Leu
1               5                   10                  15

Trp

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: See specification as filed for detailed
      description of substitutions and preferred embodiments

<400> SEQUENCE: 116

Trp Ala Leu Thr Thr Pro Phe Leu Leu Asp Ala Tyr Arg Ala Trp
1               5                   10                  15

<210> SEQ ID NO 117
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 117

Asn Leu Glu Gly Phe Phe Ala Thr Leu Gly Gly Glu Ile Ala Leu Trp
1               5                   10                  15

Ser Leu Val Val Leu Ala Ile Glu
            20

<210> SEQ ID NO 118
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 118

Glu Gly Phe Phe Ala Thr Leu Gly Gly Glu Ile Ala Leu Trp Ser Asp
1               5                   10                  15

Val Val Leu Ala Ile Glu
            20

<210> SEQ ID NO 119
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 119

Glu Gly Phe Phe Ala Thr Leu Gly Gly Glu Ile Pro Leu Trp Ser Asp
1               5                   10                  15

Val Val Leu Ala Ile Glu
            20

<210> SEQ ID NO 120
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
```

-continued description of substitutions and preferred embodiments

<400> SEQUENCE: 120

Glu Ile Ala Leu Val Val Leu Ser Trp Leu Ala Ile Glu Gly Gly Leu
1               5                   10                  15

Thr Ala Phe Phe Gly Glu Leu Asn
            20

<210> SEQ ID NO 121
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 121

Glu Ile Ala Leu Val Val Asp Ser Trp Leu Ala Ile Glu Gly Gly Leu
1               5                   10                  15

Thr Ala Phe Phe Gly Glu
            20

<210> SEQ ID NO 122
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 122

Glu Ile Ala Leu Val Val Asp Ser Trp Leu Pro Ile Glu Gly Gly Leu
1               5                   10                  15

Thr Ala Phe Phe Gly Glu
            20

<210> SEQ ID NO 123
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 123

Ile Leu Asp Leu Val Phe Gly Leu Leu Phe Ala Val Thr Ser Val Asp
1               5                   10                  15

Phe Leu Val Gln Trp
            20

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:

```
<223> OTHER INFORMATION: See specification as filed for detailed
      description of substitutions and preferred embodiments

<400> SEQUENCE: 124

Trp Gln Val Leu Phe Asp Val Ser Thr Val Ala Phe Leu Leu Gly Phe
1               5                   10                  15

Val Leu Asp Leu Ile
            20

<210> SEQ ID NO 125
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 126
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ala Glu Gln Asn Pro Ile Tyr Trp Ala Arg Tyr Ala Glu Trp Leu Phe
1               5                   10                  15

Thr Thr Pro Leu Leu Leu Leu Glu Leu Ala Leu Leu Val Glu Ala Glu
            20                  25                  30

Glu Thr

<210> SEQ ID NO 127
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ala Asp Asp Gln Asn Pro Trp Arg Ala Tyr Leu Asp Leu Leu Phe Pro
1               5                   10                  15

Asp Thr Thr Asp Leu Leu Leu Leu Asp Leu Leu Trp Asp Ala Asp Glu
            20                  25                  30

Thr

<210> SEQ ID NO 128
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128
```

Ala Glu Glu Gln Asn Pro Trp Arg Ala Tyr Leu Glu Leu Leu Phe Pro
1               5                   10                  15

Glu Thr Thr Glu Leu Leu Leu Leu Glu Leu Leu Trp Glu Ala Glu Glu
            20                  25                  30

Thr

<210> SEQ ID NO 129
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla

<400> SEQUENCE: 129

Ala Glu Gln Asn Pro Ile Tyr Trp Ala Arg Tyr Ala Xaa Trp Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 130
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Gla

<400> SEQUENCE: 130

Ala Glu Gln Asn Pro Ile Tyr Trp Ala Arg Tyr Ala Asp Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 131
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla
<220> FEATURE:
<221> NAME/KEY: MOD_RES
<222> LOCATION: (24)..(24)
<223> OTHER INFORMATION: Gla

<400> SEQUENCE: 131

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 132
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad

<400> SEQUENCE: 132

Ala Glu Gln Asn Pro Ile Tyr Trp Ala Arg Tyr Ala Xaa Trp Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 133
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Aad

<400> SEQUENCE: 133

Ala Glu Gln Asn Pro Ile Tyr Trp Ala Arg Tyr Ala Asp Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 134
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad
<220> FEATURE:
<221> NAME/KEY: MOD_RES
<222> LOCATION: (24)..(24)
<223> OTHER INFORMATION: Aad

<400> SEQUENCE: 134

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 135
<211> LENGTH: 34
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Gla
<220> FEATURE:
<221> NAME/KEY: MOD_RES
<222> LOCATION: (24)..(24)
<223> OTHER INFORMATION: Aad

<400> SEQUENCE: 135

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 136
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Aad
<220> FEATURE:
<221> NAME/KEY: MOD_RES
<222> LOCATION: (24)..(24)
<223> OTHER INFORMATION: Gla

<400> SEQUENCE: 136

Ala Glu Gln Asn Pro Ile Tyr Trp Ala Arg Tyr Ala Xaa Trp Leu Phe
1               5                   10                  15

Thr Thr Pro Leu Leu Leu Leu Xaa Leu Ala Leu Leu Val Asp Ala Asp
            20                  25                  30

Glu Thr

<210> SEQ ID NO 137
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 138
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 138

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 139
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ala Ala Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 140
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ala Glu Gln Asn Pro Ile Tyr Trp Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu Gly Thr
        35

<210> SEQ ID NO 141
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ala Glu Gln Asn Pro Ile Tyr Trp Ala Arg Tyr Ala Asn Trp Leu Phe
1               5                   10                  15

Thr Thr Pro Leu Leu Leu Leu Asn Leu Ala Leu Leu Val Asp Ala Asp
            20                  25                  30

Glu Gly Thr
        35

<210> SEQ ID NO 142
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 142

Ala Glu Gln Asn Pro Ile Tyr Trp Ala Arg Tyr Ala Lys Trp Leu Phe
1               5                   10                  15

Thr Thr Pro Leu Leu Leu Leu Lys Leu Ala Leu Leu Val Asp Ala Asp
            20                  25                  30

Glu Gly Thr
        35

<210> SEQ ID NO 143
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Leu Ala Leu Leu Val Asn Ala
            20                  25                  30

Asn Gln Gly Thr
        35

<210> SEQ ID NO 144
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ala Ala Glu Gln Asn Pro Ile Tyr Trp Ala Arg Tyr Ala Asp Trp Leu
1               5                   10                  15

Phe Thr Thr Pro Leu Leu Leu Leu Ala Leu Ala Leu Leu Val Asp Ala
            20                  25                  30

Asp Glu Gly Thr
        35

<210> SEQ ID NO 145
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Ala Ala Glu Gln Asn Pro Ile Tyr Trp Ala Arg Tyr Ala Ala Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 146
<211> LENGTH: 36
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 146

Ala Ala Glu Gln Asn Pro Ile Tyr Trp Ala Arg Tyr Ala Asp Trp Leu
1               5                   10                  15

Phe Thr Thr Ala Leu Leu Leu Leu Asp Leu Ala Leu Leu Val Asp Ala
            20                  25                  30

Asp Glu Gly Thr
            35

<210> SEQ ID NO 147
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Ala Ala Glu Gln Asn Pro Ile Tyr Trp Ala Arg Tyr Ala Asp Trp Leu
1               5                   10                  15

Phe Thr Thr Pro Leu Leu Leu Leu Glu Leu Ala Leu Leu Val Asp Ala
            20                  25                  30

Asp Glu Gly Thr
            35

<210> SEQ ID NO 148
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ala Ala Glu Gln Asn Pro Ile Tyr Trp Ala Arg Tyr Ala Glu Trp Leu
1               5                   10                  15

Phe Thr Thr Pro Leu Leu Leu Leu Asp Leu Ala Leu Leu Val Asp Ala
            20                  25                  30

Asp Glu Gly Thr
            35

<210> SEQ ID NO 149
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ala Ala Glu Gln Asn Pro Ile Ile Tyr Trp Ala Arg Tyr Ala Asp Trp
1               5                   10                  15

Leu Phe Thr Asp Leu Pro Leu Leu Leu Asp Leu Leu Ala Leu Leu
            20                  25                  30

Val Asp Ala Asp Glu Gly Thr
            35

<210> SEQ ID NO 150
<211> LENGTH: 34
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 150

Gly Glu Gln Asn Pro Ile Tyr Trp Ala Gln Tyr Ala Asp Trp Leu Phe
1               5                   10                  15

Thr Thr Pro Leu Leu Leu Asp Leu Ala Leu Leu Val Asp Ala Asp
            20                  25                  30

Glu Gly

<210> SEQ ID NO 151
<211> LENGTH: 35
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 151

Gly Gly Glu Gln Asn Pro Ile Tyr Trp Ala Arg Tyr Ala Asp Trp Leu
1               5                   10                  15

Phe Thr Thr Pro Leu Leu Leu Asp Leu Ala Leu Leu Val Asp Ala
            20                  25                  30

Asp Glu Gly
        35

<210> SEQ ID NO 152
<211> LENGTH: 35
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 152

Gly Gly Glu Gln Asn Pro Ile Tyr Trp Ala Arg Tyr Ala Asp Trp Leu
1               5                   10                  15

Phe Thr Thr Pro Leu Leu Leu Leu Asp Ala Leu Leu Val Asp Ala
            20                  25                  30

Asp Glu Gly
        35

<210> SEQ ID NO 153
<211> LENGTH: 36
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 153

Gly Gly Glu Gln Asn Pro Ile Tyr Trp Ala Arg Tyr Asp Ala Trp Leu
1               5                   10                  15

Phe Thr Thr Pro Leu Leu Leu Leu Asp Leu Ala Leu Leu Val Asp Ala
            20                  25                  30

Asp Glu Gly Thr
        35

<210> SEQ ID NO 154
<211> LENGTH: 35
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 154

Gly Gly Glu Gln Asn Pro Ile Tyr Trp Ala Arg Tyr Ala Trp Asp Leu
1               5                   10                  15

Phe Thr Thr Pro Leu Leu Leu Leu Asp Leu Ala Leu Leu Val Asp Ala
            20                  25                  30

Asp Glu Gly
        35

<210> SEQ ID NO 155
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 155

Ala Ala Glu Gln Asn Pro Ile Tyr Trp Ala Arg Tyr Ala Asp Trp Leu
1               5                   10                  15

Phe Thr Thr Gly Leu Leu Leu Leu Asp Leu Ala Leu Leu Val Asp Ala
            20                  25                  30

Asp Glu Gly Thr
        35

<210> SEQ ID NO 156
<211> LENGTH: 34
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 156

Asp Asp Asp Glu Asp Asn Pro Ile Tyr Trp Ala Arg Tyr Ala Asp Trp
1               5                   10                  15

Leu Phe Thr Thr Pro Leu Leu Leu Leu His Gly Ala Leu Leu Val Asp
            20                  25                  30

Ala Asp

<210> SEQ ID NO 157
<211> LENGTH: 33
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 157

Cys Glu Gln Asn Pro Ile Tyr Trp Ala Arg Tyr Ala Asp Trp His Phe
1               5                   10                  15

Thr Thr Pro Leu Leu Leu Leu Asp Leu Ala Leu Leu Val Asp Ala Asp
            20                  25                  30

Glu

<210> SEQ ID NO 158
<211> LENGTH: 34
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 158

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 159
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ala Glu Gln Asn Pro Ile Tyr Phe Ala Arg Tyr Ala Asp Trp Leu Phe
1               5                   10                  15

Thr Thr Pro Leu Leu Leu Leu Asp Leu Ala Leu Leu Val Asp Ala Asp
            20                  25                  30

Glu

<210> SEQ ID NO 160
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 161
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Ala Asp Asn Asn Pro Trp Ile Tyr Ala Arg Tyr Ala Asp Leu Thr Thr
1               5                   10                  15

Phe Pro Leu Leu Leu Leu Asp Leu Ala Leu Leu Val Asp Phe Asp Asp
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Ala Asp Asn Asn Pro Phe Ile Tyr Ala Arg Tyr Ala Asp Leu Thr Thr

Trp Pro Leu Leu Leu Leu Asp Leu Ala Leu Leu Val Asp Phe Asp Asp
            20                  25                  30

<210> SEQ ID NO 163
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Ala Asp Asn Asn Pro Phe Ile Tyr Ala Arg Tyr Ala Asp Leu Thr Thr
1               5                   10                  15

Phe Pro Leu Leu Leu Leu Asp Leu Ala Leu Leu Val Asp Trp Asp Asp
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ala Asp Asn Asn Pro Phe Pro Tyr Ala Arg Tyr Ala Asp Leu Thr Thr
1               5                   10                  15

Trp Ile Leu Leu Leu Leu Asp Leu Ala Leu Leu Val Asp Phe Asp Asp
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Ala Asp Asn Asn Pro Phe Ile Tyr Ala Tyr Arg Ala Asp Leu Thr Thr
1               5                   10                  15

Phe Pro Leu Leu Leu Leu Asp Leu Ala Leu Leu Val Asp Trp Asp Asp
            20                  25                  30

<210> SEQ ID NO 166
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Ala Asp Asn Asn Pro Phe Ile Tyr Ala Thr Tyr Ala Asp Leu Arg Thr
1               5                   10                  15

Phe Pro Leu Leu Leu Leu Asp Leu Ala Leu Leu Val Asp Trp Asp Asp
            20                  25                  30

<210> SEQ ID NO 167
<211> LENGTH: 33
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 167

Thr Glu Asp Ala Asp Val Leu Leu Ala Leu Asp Leu Leu Leu Pro
1               5                   10                  15

Thr Thr Phe Leu Trp Asp Ala Tyr Arg Ala Trp Tyr Pro Asn Gln Glu
            20                  25                  30

Ala

<210> SEQ ID NO 168
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Ala Glu Asp Gln Asn Pro Tyr Trp Ala Arg Tyr Ala Asp Trp Leu Phe
1               5                   10                  15

Thr Thr Pro Leu Leu Leu Leu Asp Leu Ala Leu Leu Val Asp
            20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Ala Glu Asp Gln Asn Pro Tyr Trp Ala Arg Tyr Ala Asp Trp Leu Phe
1               5                   10                  15

Thr Thr Pro Leu Leu Leu Leu Glu Leu Ala Leu Leu Val Glu
            20                  25                  30

<210> SEQ ID NO 170
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Glu Asp Gln Asn Pro Tyr Trp Arg Ala Tyr Ala Asp Leu Phe Thr
1               5                   10                  15

Pro Leu Thr Leu Leu Asp Leu Leu Ala Leu Trp Asp
            20                  25

<210> SEQ ID NO 171
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp

```
              20                  25

<210> SEQ ID NO 172
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Ala Asp Asp Gln Asn Pro Trp Arg Ala Tyr Leu Asp Leu Leu Phe Pro
1               5                   10                  15

Thr Asp Thr Leu Leu Leu Asp Leu Leu Trp Asp Ala Asp Glu
            20                  25                  30

<210> SEQ ID NO 173
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla

<400> SEQUENCE: 173

Ala Asp Asp Gln Asn Pro Trp Arg Ala Tyr Leu Xaa Leu Leu Phe Pro
1               5                   10                  15

Thr Asp Thr Leu Leu Leu Asp Leu Leu Trp
            20                  25

<210> SEQ ID NO 174
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Gla

<400> SEQUENCE: 174

Ala Asp Asp Gln Asn Pro Trp Arg Ala Tyr Leu Asp Leu Leu Phe Pro
1               5                   10                  15

Thr Xaa Thr Leu Leu Leu Asp Leu Leu Trp
            20                  25

<210> SEQ ID NO 175
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Gla

<400> SEQUENCE: 175

Ala Asp Asp Gln Asn Pro Trp Arg Ala Tyr Leu Asp Leu Leu Phe Pro
1               5                   10                  15
```

```
Thr Asp Thr Leu Leu Xaa Leu Leu Trp
            20              25
```

<210> SEQ ID NO 176
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla

<400> SEQUENCE: 176

```
Ala Asp Asp Gln Asn Pro Trp Arg Ala Tyr Leu Xaa Leu Leu Phe Pro
1               5                   10                  15

Thr Xaa Thr Leu Leu Asp Leu Leu Trp
            20              25
```

<210> SEQ ID NO 177
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 177

```
Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20              25
```

<210> SEQ ID NO 178
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 178

```
Ala Asp Asp Gln Asn Pro Trp Arg Ala Tyr Leu Asp Leu Leu Phe Pro
1               5                   10                  15

Thr Xaa Thr Leu Leu Leu Xaa Leu Leu Trp
            20              25
```

-continued

```
<210> SEQ ID NO 179
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)
<223> OTHER INFORMATION: Gla

<400> SEQUENCE: 179

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 180
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad

<400> SEQUENCE: 180

Ala Asp Asp Gln Asn Pro Trp Arg Ala Tyr Leu Xaa Leu Leu Phe Pro
1               5                   10                  15

Thr Asp Thr Leu Leu Leu Asp Leu Leu Trp
            20                  25

<210> SEQ ID NO 181
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aad

<400> SEQUENCE: 181

Ala Asp Asp Gln Asn Pro Trp Arg Ala Tyr Leu Asp Leu Leu Phe Pro
1               5                   10                  15

Thr Xaa Thr Leu Leu Leu Asp Leu Leu Trp
            20                  25

<210> SEQ ID NO 182
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (23)..(23)
<223> OTHER INFORMATION: Aad

<400> SEQUENCE: 182

Ala Asp Asp Gln Asn Pro Trp Arg Ala Tyr Leu Asp Leu Leu Phe Pro
1               5                   10                  15

Thr Asp Thr Leu Leu Leu Xaa Leu Leu Trp
            20                  25

<210> SEQ ID NO 183
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
<223> OTHER INFORMATION: Aad

<400> SEQUENCE: 183

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 184
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (23)..(23)
<223> OTHER INFORMATION: Aad

<400> SEQUENCE: 184

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 185
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)
<223> OTHER INFORMATION: Aad
```

<400> SEQUENCE: 185

Ala Asp Asp Gln Asn Pro Trp Arg Ala Tyr Leu Asp Leu Leu Phe Pro
1               5                   10                  15

Thr Xaa Thr Leu Leu Leu Xaa Leu Leu Trp
            20                  25

<210> SEQ ID NO 186
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)
<223> OTHER INFORMATION: Aad

<400> SEQUENCE: 186

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 187
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Aad

<400> SEQUENCE: 187

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 188
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (23)..(23)
<223> OTHER INFORMATION: Aad -continued

<400> SEQUENCE: 188

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 189
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Gla
<220> FEATURE:
<221> NAME/KEY: MOD_RES
<222> LOCATION: (23)..(23)
<223> OTHER INFORMATION: Aad

<400> SEQUENCE: 189

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 190
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (18)..(18)
<223> OTHER INFORMATION: Gla

<400> SEQUENCE: 190

Ala Asp Asp Gln Asn Pro Trp Arg Ala Tyr Leu Xaa Leu Leu Phe Pro
1               5                   10                  15

Thr Xaa Thr Leu Leu Leu Asp Leu Leu Trp
            20                  25

<210> SEQ ID NO 191
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Aad
<220> FEATURE:
<221> NAME/KEY: MOD_RES
<222> LOCATION: (23)..(23)
<223> OTHER INFORMATION: Gla

<400> SEQUENCE: 191

Ala Asp Asp Gln Asn Pro Trp Arg Ala Tyr Leu Xaa Leu Leu Phe Pro
1               5                   10                  15

Thr Asp Thr Leu Leu Leu Xaa Leu Leu Trp
            20                  25

<210> SEQ ID NO 192
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Gla
<220> FEATURE:
<221> NAME/KEY: MOD_RES
<222> LOCATION: (18)..(18)
<223> OTHER INFORMATION: Aad
<220> FEATURE:
<221> NAME/KEY: MOD_RES
<222> LOCATION: (23)..(23)
<223> OTHER INFORMATION: Gla

<400> SEQUENCE: 192

Ala Asp Asp Gln Asn Pro Trp Arg Ala Tyr Leu Xaa Leu Leu Phe Pro
1               5                   10                  15

Thr Xaa Thr Leu Leu Leu Xaa Leu Leu Trp
            20                  25

<210> SEQ ID NO 193
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Gly Glu Glu Gln Asn Pro Trp Leu Gly Ala Tyr Leu Asp Leu Leu Phe
1               5                   10                  15

Pro Leu Glu Leu Leu Gly Leu Leu Glu Leu Gly Leu Trp
            20                  25

<210> SEQ ID NO 194
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Asp Asp Asp Asp Asp Asp Pro Trp Gln Ala Tyr Leu Asp Leu Leu
1               5                   10                  15

Phe Pro Thr Asp Thr Leu Leu Leu Asp Leu Leu Trp
            20                  25

<210> SEQ ID NO 195
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide -continued

<400> SEQUENCE: 195

Ala Glu Glu Gln Asn Pro Trp Arg Ala Tyr Leu Glu Leu Leu Phe Pro
1               5                   10                  15

Thr Glu Thr Leu Leu Leu Glu Leu Leu Trp
            20                  25

<210> SEQ ID NO 196
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ala Asp Asp Gln Asn Pro Trp Ala Arg Tyr Leu Asp Trp Leu Phe Pro
1               5                   10                  15

Thr Asp Thr Leu Leu Leu Asp Leu
            20

<210> SEQ ID NO 197
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Asp Asn Asn Asn Pro Trp Arg Ala Tyr Leu Asp Leu Leu Phe Pro Thr
1               5                   10                  15

Asp Thr Leu Leu Leu Asp Trp
            20

<210> SEQ ID NO 198
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Glu Glu Gln Asn Pro Trp Ala Arg Tyr Leu Glu Trp Leu Phe Pro
1               5                   10                  15

Thr Glu Thr Leu Leu Leu Glu Leu
            20

<210> SEQ ID NO 199
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Asp Asp Asp Asp Asp Asp Pro Trp Gln Ala Tyr Leu Asp Leu Phe Pro
1               5                   10                  15

Thr Asp Thr Leu Ala Leu Asp Leu Trp
            20                  25

<210> SEQ ID NO 200

<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Glu Glu Gln Gln Pro Trp Ala Gln Tyr Leu Glu Leu Leu Phe Pro Thr
1               5                   10                  15

Glu Thr Leu Leu Leu Glu Trp
            20

<210> SEQ ID NO 201
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Glu Glu Gln Gln Pro Trp Arg Ala Tyr Leu Glu Leu Leu Phe Pro Thr
1               5                   10                  15

Glu Thr Leu Leu Leu Glu Trp
            20

<210> SEQ ID NO 202
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Glu Asp Gln Asn Pro Trp Ala Arg Tyr Ala Asp Trp Leu Phe Pro
1               5                   10                  15

Thr Thr Leu Leu Leu Asp
            20

<210> SEQ ID NO 203
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ala Glu Glu Gln Asn Pro Trp Ala Arg Tyr Ala Glu Trp Leu Phe Pro
1               5                   10                  15

Thr Thr Leu Leu Leu Glu
            20

<210> SEQ ID NO 204
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ala Glu Asp Gln Asn Pro Trp Ala Arg Tyr Ala Asp Leu Leu Phe Pro
1               5                   10                  15

Thr Thr Leu Ala Trp
            20

<210> SEQ ID NO 205
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Glu Glu Gln Asn Pro Trp Ala Arg Tyr Ala Glu Leu Leu Phe Pro
1               5                   10                  15

Thr Thr Leu Ala Trp
            20

<210> SEQ ID NO 206
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Asp Asp Asp Asp Asn Pro Asn Tyr Trp Ala Arg Tyr Ala Asn Trp
1               5                   10                  15

Leu Phe Thr Thr Pro Leu Leu Leu Leu Asn Gly Ala Leu Leu Val Glu
            20                  25                  30

Ala Glu Glu Thr
        35

<210> SEQ ID NO 207
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Asp Asp Asp Asp Asp Asn Pro Asn Tyr Trp Ala Arg Tyr Ala Pro Trp
1               5                   10                  15

Leu Phe Thr Thr Pro Leu Leu Leu Leu Pro Gly Ala Leu Leu Val Glu
            20                  25                  30

Ala Glu Glu Thr
        35

<210> SEQ ID NO 208
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Ala Glu Gln Asn Pro Ile Tyr Phe Ala Arg Tyr Ala Asp Phe Leu Phe
1               5                   10                  15

Thr Thr Pro Leu Leu Leu Leu Asp Leu Ala Leu Leu Trp Asp Ala Asp
            20                  25                  30

Glu Thr

<210> SEQ ID NO 209
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Ala Glu Gln Asn Pro Ile Tyr Trp Ala Arg Tyr Ala Asp Phe Leu Phe
1               5                   10                  15

Thr Thr Pro Leu Leu Leu Leu Asp Leu Ala Leu Leu Val Asp Ala Asp
            20                  25                  30

Glu Thr

<210> SEQ ID NO 210
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ala Glu Gln Asn Pro Ile Tyr Trp Ala Arg Tyr Ala Asp Trp Leu Phe
1               5                   10                  15

Thr Thr Pro Leu
            20

<210> SEQ ID NO 211
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ala Glu Gln Asn Pro Ile Tyr Phe Ala Arg Tyr Ala Asp Leu Leu Phe
1               5                   10                  15

Pro Thr Thr Leu Ala Trp
            20

<210> SEQ ID NO 212
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ala Glu Gln Asn Pro Ile Tyr Trp Ala Arg Tyr Ala Asp Leu Leu Phe
1               5                   10                  15

Pro Thr Thr Leu Ala Phe
            20

<210> SEQ ID NO 213
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Glu Gln Asn Pro Ile Tyr Trp Ala Arg Tyr Ala Asp Leu Leu Phe
1               5                   10                  15

Pro Thr Thr Leu Ala Trp
            20

<210> SEQ ID NO 214
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ala Glu Gln Asn Pro Ile Tyr Phe Ala Arg Tyr Ala Asp Trp Leu Phe
1               5                   10                  15

Thr Thr Pro Leu
            20

<210> SEQ ID NO 215
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Glu Asp Gln Asn Pro Trp Ala Arg Tyr Ala Asp Leu Leu Phe Pro Thr
1               5                   10                  15

Thr Leu Ala Trp
            20

<210> SEQ ID NO 216
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gly Leu Ala Gly Leu Ala Gly Leu Leu Gly Leu Glu Gly Leu Leu Gly
1               5                   10                  15

Leu Pro Leu Gly Leu Leu Glu Gly Leu Trp Leu Gly Leu Glu Leu Glu
            20                  25                  30

Gly Asn

<210> SEQ ID NO 217
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Gln Asn Pro Ile Tyr Ile Leu Asp Leu Val Phe Gly Leu Leu Phe
1               5                   10                  15

Ala Val Thr Ser Val Asp Phe Leu Val Gln Trp Asp Asp Ala Gly Asp
            20                  25                  30

<210> SEQ ID NO 218
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Asn Leu Glu Gly Phe Phe Ala Thr Leu Gly Gly Glu Ile Ala Leu Trp
1               5                   10                  15

Ser Leu Val Val Leu Ala Ile Glu
            20

<210> SEQ ID NO 219
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Asn Asn Glu Gly Phe Phe Ala Thr Leu Gly Gly Glu Ile Ala Leu Trp
1               5                   10                  15

Ser Asp Val Val Leu Ala Ile Glu
            20

<210> SEQ ID NO 220
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asp Asn Asn Glu Gly Phe Phe Ala Thr Leu Gly Gly Glu Ile Pro Leu
1               5                   10                  15

Trp Ser Asp Val Val Leu Ala Ile Glu
            20                  25

<210> SEQ ID NO 221
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Trp Glu Trp Glu Trp Glu Trp Cys
1               5

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Trp Glu Trp Glu Trp Glu Trp Glu Trp Cys
1               5                   10

<210> SEQ ID NO 223
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Trp Glu Trp Glu Trp Glu Trp Glu Trp Glu Trp Cys
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Leu Glu Leu Glu Leu Glu Leu Glu Trp Cys
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Glu Glu Glu Glu Trp Trp Trp Trp Trp Cys
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Cys Trp Glu Trp Glu Trp Glu Trp Glu Trp
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Arg Arg Arg Arg Trp Trp Trp Trp Trp Cys
1               5                   10

<210> SEQ ID NO 228
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 228

Glu Glu Glu Trp Trp Trp Trp Trp Cys
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Glu Trp Glu Trp Trp Trp Trp Glu Cys
1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Glu Trp Trp Glu Trp Trp Trp Glu Cys
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Glu Trp Trp Trp Glu Trp Trp Glu Cys
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Glu Trp Trp Trp Trp Glu Trp Glu Cys
1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Glu Trp Trp Trp Trp Trp Glu Glu Cys
1               5

<210> SEQ ID NO 234
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 234

Glu Trp Glu Glu Trp Trp Trp Trp Cys
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Glu Trp Trp Glu Glu Trp Trp Trp Cys
1               5

<210> SEQ ID NO 236
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Glu Trp Trp Trp Glu Glu Trp Trp Cys
1               5

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Glu Trp Trp Trp Trp Glu Glu Trp Cys
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Trp Glu Glu Glu Trp Trp Trp Trp Cys
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Trp Trp Glu Glu Glu Trp Trp Trp Cys
1               5
```

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Trp Trp Trp Glu Glu Glu Trp Trp Cys
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Trp Trp Trp Trp Glu Glu Glu Trp Cys
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Trp Glu Trp Glu Glu Trp Trp Trp Cys
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Trp Glu Trp Trp Glu Glu Trp Trp Cys
1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Trp Glu Trp Trp Trp Glu Glu Trp Cys
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 245

Trp Glu Trp Trp Trp Trp Glu Glu Cys
1               5

<210> SEQ ID NO 246
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Glu Glu Glu Trp Trp Trp Trp Trp
1               5

<210> SEQ ID NO 247
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Glu Trp Glu Trp Trp Trp Trp Glu
1               5

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Glu Trp Trp Glu Trp Trp Trp Glu
1               5

<210> SEQ ID NO 249
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Glu Trp Trp Trp Glu Trp Trp Glu
1               5

<210> SEQ ID NO 250
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Trp Trp Trp Trp Glu Trp Glu
1               5

<210> SEQ ID NO 251
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Glu Trp Trp Trp Trp Trp Glu Glu
1               5

<210> SEQ ID NO 252
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Glu Trp Glu Glu Trp Trp Trp Trp
1               5

<210> SEQ ID NO 253
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Glu Trp Trp Glu Glu Trp Trp Trp
1               5

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Glu Trp Trp Trp Glu Glu Trp Trp
1               5

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Glu Trp Trp Trp Trp Glu Glu Trp
1               5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Trp Glu Glu Glu Trp Trp Trp Trp
```

```
1               5
```

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

```
Trp Trp Glu Glu Glu Trp Trp Trp
1               5
```

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

```
Trp Trp Trp Glu Glu Glu Trp Trp
1               5
```

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

```
Trp Trp Trp Trp Glu Glu Glu Trp
1               5
```

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

```
Trp Glu Trp Glu Glu Trp Trp Trp
1               5
```

<210> SEQ ID NO 261
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

```
Trp Glu Trp Trp Glu Glu Trp Trp
1               5
```

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic

```
peptide

<400> SEQUENCE: 262

Trp Glu Trp Trp Trp Glu Glu Trp
1               5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Trp Glu Trp Trp Trp Trp Glu Glu
1               5

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Asp Asp Asp Trp Trp Trp Trp Trp Cys
1               5

<210> SEQ ID NO 265
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Asp Trp Asp Trp Trp Trp Trp Asp Cys
1               5

<210> SEQ ID NO 266
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Asp Trp Trp Asp Trp Trp Trp Asp Cys
1               5

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Asp Trp Trp Trp Asp Trp Trp Asp Cys
1               5

<210> SEQ ID NO 268
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Asp Trp Trp Trp Trp Asp Trp Asp Cys
1               5

<210> SEQ ID NO 269
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Asp Trp Trp Trp Trp Trp Asp Asp Cys
1               5

<210> SEQ ID NO 270
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Asp Trp Asp Asp Trp Trp Trp Trp Cys
1               5

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Asp Trp Trp Asp Asp Trp Trp Trp Cys
1               5

<210> SEQ ID NO 272
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Asp Trp Trp Trp Asp Asp Trp Trp Cys
1               5

<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273
```

Asp Trp Trp Trp Trp Asp Asp Trp Cys
1               5

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Trp Asp Asp Asp Trp Trp Trp Trp Cys
1               5

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Trp Trp Asp Asp Asp Trp Trp Trp Cys
1               5

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Trp Trp Trp Asp Asp Asp Trp Trp Cys
1               5

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Trp Trp Trp Trp Asp Asp Asp Trp Cys
1               5

<210> SEQ ID NO 278
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Trp Asp Trp Asp Asp Trp Trp Trp Cys
1               5

<210> SEQ ID NO 279
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 279

Trp Asp Trp Trp Asp Asp Trp Cys
1               5

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Trp Asp Trp Trp Trp Asp Asp Trp Cys
1               5

<210> SEQ ID NO 281
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Trp Asp Trp Trp Trp Trp Asp Asp Cys
1               5

<210> SEQ ID NO 282
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Asp Asp Asp Trp Trp Trp Trp Trp
1               5

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Asp Trp Asp Trp Trp Trp Trp Asp
1               5

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Asp Trp Trp Asp Trp Trp Trp Asp
1               5

```
<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Asp Trp Trp Trp Asp Trp Trp Asp
1               5

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Asp Trp Trp Trp Trp Asp Trp Asp
1               5

<210> SEQ ID NO 287
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Asp Trp Trp Trp Trp Trp Asp Asp
1               5

<210> SEQ ID NO 288
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Asp Trp Asp Asp Trp Trp Trp Trp
1               5

<210> SEQ ID NO 289
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Asp Trp Trp Asp Asp Trp Trp Trp
1               5

<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290
```

```
Asp Trp Trp Trp Asp Asp Trp Trp
1               5

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Asp Trp Trp Trp Trp Asp Asp Trp
1               5

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Trp Asp Asp Asp Trp Trp Trp Trp
1               5

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Trp Trp Asp Asp Asp Trp Trp Trp
1               5

<210> SEQ ID NO 294
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Trp Trp Trp Asp Asp Asp Trp Trp
1               5

<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Trp Trp Trp Trp Asp Asp Asp Trp
1               5

<210> SEQ ID NO 296
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 296

Trp Asp Trp Asp Asp Trp Trp Trp
1               5

<210> SEQ ID NO 297
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Trp Asp Trp Trp Asp Asp Trp Trp
1               5

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Trp Asp Trp Trp Trp Asp Asp Trp
1               5

<210> SEQ ID NO 299
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Trp Asp Trp Trp Trp Trp Asp Asp
1               5

<210> SEQ ID NO 300
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Gla

<400> SEQUENCE: 300

Xaa Xaa Xaa Trp Trp Trp Trp Trp
1               5

<210> SEQ ID NO 301
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Gla
<220> FEATURE:
<221> NAME/KEY: MOD_RES
<222> LOCATION: (3)..(3)
<223> OTHER INFORMATION: Gla
<220> FEATURE:
<221> NAME/KEY: MOD_RES
<222> LOCATION: (8)..(8)
<223> OTHER INFORMATION: Gla

<400> SEQUENCE: 301

Xaa Trp Xaa Trp Trp Trp Trp Xaa
1               5

<210> SEQ ID NO 302
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (4)..(4)
<223> OTHER INFORMATION: Gla
<220> FEATURE:
<221> NAME/KEY: MOD_RES
<222> LOCATION: (8)..(8)
<223> OTHER INFORMATION: Gla

<400> SEQUENCE: 302

Xaa Trp Trp Xaa Trp Trp Trp Xaa
1               5

<210> SEQ ID NO 303
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (5)..(5)
<223> OTHER INFORMATION: Gla
<220> FEATURE:
<221> NAME/KEY: MOD_RES
<222> LOCATION: (8)..(8)
<223> OTHER INFORMATION: Gla

<400> SEQUENCE: 303

Xaa Trp Trp Trp Xaa Trp Trp Xaa
1               5

<210> SEQ ID NO 304
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Gla
<220> FEATURE:
<221> NAME/KEY: MOD_RES
<222> LOCATION: (6)..(6)
<223> OTHER INFORMATION: Gla
<220> FEATURE:
<221> NAME/KEY: MOD_RES
<222> LOCATION: (8)..(8)
<223> OTHER INFORMATION: Gla

<400> SEQUENCE: 304

Xaa Trp Trp Trp Trp Xaa Trp Xaa
1               5

<210

<210> SEQ ID NO 308
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (5)..(6)
<223> OTHER INFORMATION: Gla

<400> SEQUENCE: 308

Xaa Trp Trp Trp Xaa Xaa Trp Trp
1               5

<210> SEQ ID NO 309
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (6)..(7)
<223> OTHER INFORMATION: Gla

<400> SEQUENCE: 309

Xaa Trp Trp Trp Trp Xaa Xaa Trp
1               5

<210> SEQ ID NO 310
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Gla

<400> SEQUENCE: 310

Trp Xaa Xaa Xaa Trp Trp Trp Trp
1               5

<210> SEQ ID NO 311
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Gla

<400> SEQUENCE: 311

```
Trp Trp Xaa Xaa Xaa Trp Trp Trp
1               5

<210> SEQ ID NO 312
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Gla

<400> SEQUENCE: 312

Trp Trp Trp Xaa Xaa Xaa Trp Trp
1               5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Gla

<400> SEQUENCE: 313

Trp Trp Trp Trp Xaa Xaa Xaa Trp
1               5

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (4)..(5)
<223> OTHER INFORMATION: Gla

<400> SEQUENCE: 314

Trp Xaa Trp Xaa Xaa Trp Trp Trp
1               5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (5)..(6)
<223> OTHER INFORMATION: Gla

<400> SEQUENCE: 315
```

```
Trp Xaa Trp Trp Xaa Xaa Trp Trp
1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (6)..(7)
<223> OTHER INFORMATION: Gla

<400> SEQUENCE: 316

Trp Xaa Trp Trp Trp Xaa Xaa Trp
1               5

<210> SEQ ID NO 317
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (7)..(8)
<223> OTHER INFORMATION: Gla

<400> SEQUENCE: 317

Trp Xaa Trp Trp Trp Trp Xaa Xaa
1               5

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Glu Glu Glu Trp Trp Trp Trp Cys
1               5

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Glu Trp Glu Trp Trp Trp Glu Cys
1               5

<210> SEQ ID NO 320
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Glu Trp Trp Glu Trp Trp Glu Cys
1               5

<210> SEQ ID NO 321
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Glu Trp Trp Trp Glu Trp Glu Cys
1               5

<210> SEQ ID NO 322
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Glu Trp Trp Trp Trp Glu Glu Cys
1               5

<210> SEQ ID NO 323
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Glu Trp Glu Glu Trp Trp Trp Cys
1               5

<210> SEQ ID NO 324
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Glu Trp Trp Glu Glu Trp Trp Cys
1               5

<210> SEQ ID NO 325
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Glu Trp Trp Trp Glu Glu Trp Cys
```

1               5

<210> SEQ ID NO 326
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Glu Trp Trp Trp Trp Glu Glu Cys
1               5

<210> SEQ ID NO 327
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Trp Glu Glu Glu Trp Trp Trp Cys
1               5

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Trp Trp Glu Glu Glu Trp Trp Cys
1               5

<210> SEQ ID NO 329
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Trp Trp Trp Glu Glu Glu Trp Cys
1               5

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Trp Trp Trp Trp Glu Glu Glu Cys
1               5

<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 331

Trp Glu Trp Glu Glu Trp Trp Cys
1               5

<210> SEQ ID NO 332
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Trp Glu Trp Trp Glu Glu Trp Cys
1               5

<210> SEQ ID NO 333
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Trp Glu Trp Trp Trp Glu Glu Cys
1               5

<210> SEQ ID NO 334
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Glu Glu Glu Trp Trp Trp Trp
1               5

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Glu Trp Glu Trp Trp Trp Glu
1               5

<210> SEQ ID NO 336
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Glu Trp Trp Glu Trp Trp Glu
1               5

<210> SEQ ID NO 337

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Glu Trp Trp Trp Glu Trp Glu
1               5

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Glu Trp Trp Trp Trp Glu Glu
1               5

<210> SEQ ID NO 339
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Glu Trp Glu Glu Trp Trp Trp
1               5

<210> SEQ ID NO 340
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Glu Trp Trp Glu Glu Trp Trp
1               5

<210> SEQ ID NO 341
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Glu Trp Trp Trp Glu Glu Trp
1               5

<210> SEQ ID NO 342
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342
```

```
Glu Trp Trp Trp Trp Glu Glu
1               5
```

<210> SEQ ID NO 343
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

```
Trp Glu Glu Glu Trp Trp Trp
1               5
```

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

```
Trp Trp Glu Glu Glu Trp Trp
1               5
```

<210> SEQ ID NO 345
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

```
Trp Trp Trp Glu Glu Glu Trp
1               5
```

<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

```
Trp Trp Trp Trp Glu Glu Glu
1               5
```

<210> SEQ ID NO 347
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

```
Trp Glu Trp Glu Glu Trp Trp
1               5
```

<210> SEQ ID NO 348
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 348

Trp Glu Trp Trp Glu Glu Trp
1               5

<210> SEQ ID NO 349
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Trp Glu Trp Trp Trp Glu Glu
1               5

<210> SEQ ID NO 350
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Asp Asp Asp Trp Trp Trp Trp Cys
1               5

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Asp Trp Asp Trp Trp Trp Asp Cys
1               5

<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Asp Trp Trp Asp Trp Trp Asp Cys
1               5

<210> SEQ ID NO 353
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Asp Trp Trp Trp Asp Trp Asp Cys
1               5

```
<210> SEQ ID NO 354
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asp Trp Trp Trp Trp Asp Asp Cys
1               5

<210> SEQ ID NO 355
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Asp Trp Asp Asp Trp Trp Trp Cys
1               5

<210> SEQ ID NO 356
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Asp Trp Trp Asp Asp Trp Trp Cys
1               5

<210> SEQ ID NO 357
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Asp Trp Trp Trp Asp Asp Trp Cys
1               5

<210> SEQ ID NO 358
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Asp Trp Trp Trp Trp Asp Asp Cys
1               5

<210> SEQ ID NO 359
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359
```

Trp Asp Asp Asp Trp Trp Trp Cys
1               5

<210> SEQ ID NO 360
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Trp Trp Asp Asp Asp Trp Trp Cys
1               5

<210> SEQ ID NO 361
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Trp Trp Trp Asp Asp Asp Trp Cys
1               5

<210> SEQ ID NO 362
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Trp Trp Trp Trp Asp Asp Asp Cys
1               5

<210> SEQ ID NO 363
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Trp Asp Trp Asp Asp Trp Trp Cys
1               5

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Trp Asp Trp Trp Asp Asp Trp Cys
1               5

<210> SEQ ID NO 365
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 365

Trp Asp Trp Trp Trp Asp Asp Cys
1               5

<210> SEQ ID NO 366
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Asp Asp Asp Trp Trp Trp Trp
1               5

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Asp Trp Asp Trp Trp Trp Asp
1               5

<210> SEQ ID NO 368
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Asp Trp Trp Asp Trp Trp Asp
1               5

<210> SEQ ID NO 369
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Asp Trp Trp Trp Asp Trp Asp
1               5

<210> SEQ ID NO 370
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Asp Trp Trp Trp Trp Asp Asp
1               5
```

<210> SEQ ID NO 371
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Asp Trp Asp Asp Trp Trp Trp
1               5

<210> SEQ ID NO 372
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Asp Trp Trp Asp Asp Trp Trp
1               5

<210> SEQ ID NO 373
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Asp Trp Trp Trp Asp Asp Trp
1               5

<210> SEQ ID NO 374
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Asp Trp Trp Trp Trp Asp Asp
1               5

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Trp Asp Asp Asp Trp Trp Trp
1               5

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 376

Trp Trp Asp Asp Trp Trp
1               5

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Trp Trp Trp Asp Asp Asp Trp
1               5

<210> SEQ ID NO 378
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Trp Trp Trp Trp Asp Asp Asp
1               5

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Trp Asp Trp Asp Asp Trp Trp
1               5

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Trp Asp Trp Trp Asp Asp Trp
1               5

<210> SEQ ID NO 381
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Trp Asp Trp Trp Trp Asp Asp
1               5

<210> SEQ ID NO 382
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: Gla

<400> SEQUENCE: 382

Xaa Xaa Xaa Trp Trp Trp Trp
1               5

<210> SEQ ID NO 383
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (3)..(3)
<223> OTHER INFORMATION: Gla
<220> FEATURE:
<221> NAME/KEY: MOD_RES
<222> LOCATION: (7)..(7)
<223> OTHER INFORMATION: Gla

<400> SEQUENCE: 383

Xaa Trp Xaa Trp Trp Trp Xaa
1               5

<210> SEQ ID NO 384
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (4)..(4)
<223> OTHER INFORMATION: Gla
<220> FEATURE:
<221> NAME/KEY: MOD_RES
<222> LOCATION: (7)..(7)
<223> OTHER INFORMATION: Gla

<400> SEQUENCE: 384

Xaa Trp Trp Xaa Trp Trp Xaa
1               5

<210> SEQ ID NO 385
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
```

```
<221> NAME/KEY: MOD_RES
<222> LOCATION: (5)..(5)
<223> OTHER INFORMATION: Gla
<220> FEATURE:
<221> NAME/KEY: MOD_RES
<222> LOCATION: (7)..(7)
<223> OTHER INFORMATION: Gla

<400> SEQUENCE: 385

Xaa Trp Trp Trp Xaa Trp Xaa
1               5

<210> SEQ ID NO 386
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (6)..(7)
<223> OTHER INFORMATION: Gla

<400> SEQUENCE: 386

Xaa Trp Trp Trp Trp Xaa Xaa
1               5

<210> SEQ ID NO 387
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (3)..(4)
<223> OTHER INFORMATION: Gla

<400> SEQUENCE: 387

Xaa Trp Xaa Xaa Trp Trp Trp
1               5

<210> SEQ ID NO 388
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (4)..(5)
<223> OTHER INFORMATION: Gla

<400> SEQUENCE: 388

Xaa Trp Trp Xaa Xaa Trp Trp
1               5
```

```
<210> SEQ ID NO 389
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (5)..(6)
<223> OTHER INFORMATION: Gla

<400> SEQUENCE: 389

Xaa Trp Trp Trp Xaa Xaa Trp
1               5

<210> SEQ ID NO 390
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (6)..(7)
<223> OTHER INFORMATION: Gla

<400> SEQUENCE: 390

Xaa Trp Trp Trp Trp Xaa Xaa
1               5

<210> SEQ ID NO 391
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Gla

<400> SEQUENCE: 391

Trp Xaa Xaa Xaa Trp Trp Trp
1               5

<210> SEQ ID NO 392
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Gla

<400> SEQUENCE: 392

Trp Trp Xaa Xaa Xaa Trp Trp
1               5
```

```
<210> SEQ ID NO 393
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Gla

<400> SEQUENCE: 393

Trp Trp Trp Xaa Xaa Xaa Trp
1               5

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(7)
<223> OTHER INFORMATION: Gla

<400> SEQUENCE: 394

Trp Trp Trp Trp Xaa Xaa Xaa
1               5

<210> SEQ ID NO 395
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (4)..(5)
<223> OTHER INFORMATION: Gla

<400> SEQUENCE: 395

Trp Xaa Trp Xaa Xaa Trp Trp
1               5

<210> SEQ ID NO 396
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (5)..(6)
<223> OTHER INFORMATION: Gla

<400> SEQUENCE: 396

Trp Xaa Trp Trp Xaa Xaa Trp
```

```
<210> SEQ ID NO 397
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (6)..(7)
<223> OTHER INFORMATION: Gla

<400> SEQUENCE: 397

Trp Xaa Trp Trp Trp Xaa Xaa
1               5

<210> SEQ ID NO 398
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Trp Glu Trp Glu Trp Glu Trp Cys
1               5

<210> SEQ ID NO 399
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Glu Trp Glu Trp Glu Trp Trp Cys
1               5

<210> SEQ ID NO 400
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Trp Asp Trp Asp Trp Asp Trp Cys
1               5

<210> SEQ ID NO 401
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Asp Trp Asp Trp Asp Trp Trp Cys
1               5
```

```
<210> SEQ ID NO 402
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (4)..(4)
<223> OTHER INFORMATION: Gla

<400> SEQUENCE: 402

Trp Xaa Trp Xaa Trp Asp Trp Cys
1               5

<210> SEQ ID NO 403
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Asp Trp Asp Trp Asp Trp Asp Cys
1               5

<210> SEQ ID NO 404
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Trp Glu Trp Glu Trp Glu Trp Glu
1               5

<210> SEQ ID NO 405
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Glu Trp Glu Trp Glu Trp Glu Trp
1               5

<210> SEQ ID NO 406
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Trp Asp Trp Asp Trp Asp Trp Asp
1               5
```

<210> SEQ ID NO 407
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Asp Trp Asp Trp Asp Trp Asp Trp
1               5

<210> SEQ ID NO 408
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (4)..(4)
<223> OTHER INFORMATION: Gla
<220> FEATURE:
<221> NAME/KEY: MOD_RES
<222> LOCATION: (6)..(6)
<223> OTHER INFORMATION: Gla
<220> FEATURE:
<221> NAME/KEY: MOD_RES
<222> LOCATION: (8)..(8)
<223> OTHER INFORMATION: Gla

<400> SEQUENCE: 408

Trp Xaa Trp Xaa Trp Xaa Trp Xaa
1               5

<210> SEQ ID NO 409
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gla
<220> FEATURE:
<221> NAME/KEY: MOD_RES
<222> LOCATION: (3)..(3)
<223> OTHER INFORMATION: Gla
<220> FEATURE:
<221> NAME/KEY: MOD_RES
<222> LOCATION: (5)..(5)
<223> OTHER INFORMATION: Gla
<220> FEATURE:
<221> NAME/KEY: MOD_RES
<222> LOCATION: (7)..(7)
<223> OTHER INFORMATION: Gla

<400> SEQUENCE: 409

Xaa Trp Xaa Trp Xaa Trp Xaa Trp
1               5

<210> SEQ ID NO 410
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 410

Cys Trp Glu Trp Glu Trp Glu Trp Glu Trp
1               5                   10

<210> SEQ ID NO 411
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gla
<220> FEATURE:
<221> NAME/KEY: MOD_RES
<222> LOCATION: (4)..(4)
<223> OTHER INFORMATION: Gla

<400> SEQUENCE: 411

Trp Xaa Trp Xaa Trp Asp Trp Cys
1               5

<210> SEQ ID NO 412
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

Glu Trp Glu Trp Glu Trp Glu Cys
1               5

<210> SEQ ID NO 413
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Asp Trp Asp Trp Asp Trp Asp Cys
1               5

<210> SEQ ID NO 414
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Glu Glu Glu Glu Glu Lys
1               5

<210> SEQ ID NO 415
<211> LENGTH: 6
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 415

Trp Trp Trp Trp Trp Cys
1               5

<210> SEQ ID NO 416
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Glu Glu Glu Glu Lys
1               5

<210> SEQ ID NO 417
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Trp Trp Trp Trp Trp Cys
1               5

<210> SEQ ID NO 418
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Glu Glu Glu Glu Glu Lys
1               5

<210> SEQ ID NO 419
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Trp Trp Trp Trp Cys
1               5

<210> SEQ ID NO 420
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Glu Glu Glu Glu Lys
1               5

```
<210> SEQ ID NO 421
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Trp Trp Trp Trp Cys
1               5

<210> SEQ ID NO 422
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

Glu Glu Glu Glu Glu Lys
1               5

<210> SEQ ID NO 423
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 423

Trp Trp Trp Trp Trp
1               5

<210> SEQ ID NO 424
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Glu Glu Glu Glu Lys
1               5

<210> SEQ ID NO 425
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Trp Trp Trp Trp Trp
1               5

<210> SEQ ID NO 426
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426
```

```
Glu Glu Glu Glu Glu Lys
1               5

<210> SEQ ID NO 427
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Trp Trp Trp Trp
1

<210> SEQ ID NO 428
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Glu Glu Glu Glu Lys
1               5

<210> SEQ ID NO 429
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Trp Trp Trp Trp
1

<210> SEQ ID NO 430
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Asp Asp Asp Asp Asp Lys
1               5

<210> SEQ ID NO 431
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Trp Trp Trp Trp Trp Cys
1               5

<210> SEQ ID NO 432
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 432

Asp Asp Asp Asp Lys
1               5

<210> SEQ ID NO 433
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 433

Trp Trp Trp Trp Trp Cys
1               5

<210> SEQ ID NO 434
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Asp Asp Asp Asp Asp Lys
1               5

<210> SEQ ID NO 435
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Trp Trp Trp Trp Cys
1               5

<210> SEQ ID NO 436
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Asp Asp Asp Asp Lys
1               5

<210> SEQ ID NO 437
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 437

Trp Trp Trp Trp Cys
1               5
```

<210> SEQ ID NO 438
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Asp Asp Asp Asp Asp Lys
1               5

<210> SEQ ID NO 439
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Trp Trp Trp Trp Trp
1               5

<210> SEQ ID NO 440
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Asp Asp Asp Asp Lys
1               5

<210> SEQ ID NO 441
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

Trp Trp Trp Trp Trp
1               5

<210> SEQ ID NO 442
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

Asp Asp Asp Asp Asp Lys
1               5

<210> SEQ ID NO 443
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 443

Trp Trp Trp Trp
1

<210> SEQ ID NO 444
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 444

Asp Asp Asp Asp Lys
1               5

<210> SEQ ID NO 445
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Trp Trp Trp Trp
1

<210> SEQ ID NO 446
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Gla

<400> SEQUENCE: 446

Xaa Xaa Xaa Xaa Xaa Lys
1               5

<210> SEQ ID NO 447
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Trp Trp Trp Trp Trp Cys
1               5

<210> SEQ ID NO 448
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Gla

<400> SEQUENCE: 448
```

```
Xaa Xaa Xaa Xaa Lys
1               5

<210> SEQ ID NO 449
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Trp Trp Trp Trp Trp Cys
1               5

<210> SEQ ID NO 450
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Gla

<400> SEQUENCE: 450

Xaa Xaa Xaa Xaa Xaa Lys
1               5

<210> SEQ ID NO 451
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Trp Trp Trp Trp Cys
1               5

<210> SEQ ID NO 452
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Gla

<400> SEQUENCE: 452

Xaa Xaa Xaa Xaa Lys
1               5

<210> SEQ ID NO 453
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453
```

```
Trp Trp Trp Trp Cys
1               5

<210> SEQ ID NO 454
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Gla

<400> SEQUENCE: 454

Xaa Xaa Xaa Xaa Xaa Lys
1               5

<210> SEQ ID NO 455
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

Trp Trp Trp Trp Trp
1               5

<210> SEQ ID NO 456
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Gla

<400> SEQUENCE: 456

Xaa Xaa Xaa Xaa Lys
1               5

<210> SEQ ID NO 457
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

Trp Trp Trp Trp Trp
1               5

<210> SEQ ID NO 458
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Gla
```

```
<400> SEQUENCE: 458

Xaa Xaa Xaa Xaa Xaa Lys
1               5

<210> SEQ ID NO 459
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Trp Trp Trp Trp
1

<210> SEQ ID NO 460
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Gla

<400> SEQUENCE: 460

Xaa Xaa Xaa Xaa Lys
1               5

<210> SEQ ID NO 461
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Trp Trp Trp Trp
1

<210> SEQ ID NO 462
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 462

Glu Glu Glu Glu Glu Trp Trp Trp Trp Trp Cys
1               5                   10

<210> SEQ ID NO 463
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

Glu Glu Glu Glu Trp Trp Trp Trp Cys
1               5
```

```
<210> SEQ ID NO 464
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

Trp Glu Trp Glu Trp Glu Trp Glu Cys Trp
1               5                   10

<210> SEQ ID NO 465
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 465

Trp Arg Trp Arg Trp Arg Trp Arg Trp Cys
1               5                   10

<210> SEQ ID NO 466

<400> SEQUENCE: 466

000

<210> SEQ ID NO 467

<400> SEQUENCE: 467

000

<210> SEQ ID NO 468
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser(Rha)

<400> SEQUENCE: 468

Ala Ser Asp Asp Gln Asn Pro Trp Arg Ala Tyr Leu Asp Leu Leu Phe
1               5                   10                  15

Pro Thr Asp Thr Leu Leu Leu Asp Leu Leu Trp Ala
            20                  25

<210> SEQ ID NO 469
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Ala Cys Asp Asp Gln Asn Pro Trp Arg Ala Tyr Leu Asp Leu Leu Phe
1               5                   10                  15

Pro Thr Asp Thr Leu Leu Leu Asp Leu Leu Trp Ala
            20                  25
```

```
<210> SEQ ID NO 470
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

Ala Lys Gln Asn Asp Asp Gln Asn Lys Pro Trp Arg Ala Tyr Leu Asp
1               5                   10                  15

Leu Leu Phe Pro Thr Asp Thr Leu Leu Asp Leu Leu Trp Ala
            20                  25                  30

<210> SEQ ID NO 471
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Ala Cys Gln Asn Asp Asp Gln Asn Cys Pro Trp Arg Ala Tyr Leu Asp
1               5                   10                  15

Leu Leu Phe Pro Thr Asp Thr Leu Leu Asp Leu Leu Trp Ala
            20                  25                  30

<210> SEQ ID NO 472
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Gln Asn Asp Asp Gln Asn
1               5

<210> SEQ ID NO 473
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(13)
<223> OTHER INFORMATION: Any amino acid
<220> FEATURE:
<221> NAME/KEY: MISC_FEATURE
<222> LOCATION: (3)..(12)
<223> OTHER INFORMATION: This region may encompass 1-10 residues
<220> FEATURE:
<223> OTHER INFORMATION: See specification as filed for detailed
      description of substitutions and preferred embodiments

<400> SEQUENCE: 473

Ala Xaa Xaa Xaa Xaa Xaa Xaa Xaa Xaa Xaa Xaa Xaa Xaa Pro Trp Arg
1               5                   10                  15

Ala Tyr Leu Asp Leu Leu Phe Pro Thr Asp Thr Leu Leu Asp Leu
            20                  25                  30

Leu Trp Ala
        35
```

```
<210> SEQ ID NO 474
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Ala Lys Asp Asp Gln Asn Pro Trp Arg Ala Tyr Leu Asp Leu Leu Phe
1               5                   10                  15

Pro Thr Asp Thr Leu Leu Leu Asp Leu Leu Trp Ala
            20                  25

<210> SEQ ID NO 475
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Cys or an Azido-containing amino acid
<220> FEATURE:
<223> OTHER INFORMATION: See specification as filed for detailed
      description of substitutions and preferred embodiments

<400> SEQUENCE: 475

Ala Xaa Asp Gln Asp Asn Pro Trp Arg Ala Tyr Leu Asp Leu Leu Phe
1               5                   10                  15

Pro Thr Asp Thr Leu Leu Leu Asp Leu Leu Trp Ala Ala
            20                  25

<210> SEQ ID NO 476
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Asp Asp Asp Glu Asp Asn Pro Ile Tyr Trp Ala Arg Tyr Ala His Trp
1               5                   10                  15

Leu Phe Thr Thr Pro Leu Leu Leu Leu His Gly Ala Leu Leu Val Asp
            20                  25                  30

Ala Asp Glu
        35

<210> SEQ ID NO 477
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 477

Trp Trp Trp Trp Trp Cys
1               5

<210> SEQ ID NO 478
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 478

Trp Trp Trp Trp Cys
1               5

<210> SEQ ID NO 479
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 479

Ala Lys Gln Asn Asp Asn Asp Asn Lys Pro Trp Arg Ala Tyr Leu Asp
1               5                   10                  15

Leu Leu Phe Pro Thr Asp Thr Leu Leu Leu Asp Leu Leu Trp Ala
            20                  25                  30

<210> SEQ ID NO 480
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Ala Cys Gln Asn Asp Asn Asp Asn Cys Pro Trp Arg Ala Tyr Leu Asp
1               5                   10                  15

Leu Leu Phe Pro Thr Asp Thr Leu Leu Leu Asp Leu Leu Trp Ala
            20                  25                  30

<210> SEQ ID NO 481
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Cys, Ser, Thr or an Azido-containing amino
      acid

<400> SEQUENCE: 481

Ala Xaa Asp Asp Gln Asn Pro Trp Arg Ala Tyr Leu Asp Leu Leu Phe
1               5                   10                  15

Pro Thr Asp Thr Leu Leu Leu Asp Leu Leu Trp
            20                  25

<210> SEQ ID NO 482
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Lys, Cys, Ser, Thr or an Azido-containing amino
      acid
```

```
<400> SEQUENCE: 482

Ala Xaa Asp Gln Asp Asn Pro Trp Arg Ala Tyr Leu Asp Leu Leu Phe
1               5                   10                  15

Pro Thr Asp Thr Leu Leu Leu Asp Leu Leu Trp
                20                  25
```